(12) United States Patent
Chiu et al.

(10) Patent No.: US 9,273,038 B2
(45) Date of Patent: Mar. 1, 2016

(54) SOLID FORMS OF AN ION CHANNEL MODULATOR

(71) Applicant: Gilead Sciences, Inc., Foster City, CA (US)

(72) Inventors: Anna Chiu, Mountain View, CA (US); Olga V. Lapina, Newark, CA (US); Petinka I. Vlahova, West Lafayette, IN (US)

(73) Assignee: Gilead Sciences, Inc., Foster City, CA (US)

( * ) Notice: Subject to any disclaimer, the term of this patent is extended or adjusted under 35 U.S.C. 154(b) by 0 days.

(21) Appl. No.: 14/620,970

(22) Filed: Feb. 12, 2015

(65) Prior Publication Data

US 2015/0225383 A1 Aug. 13, 2015

Related U.S. Application Data

(60) Provisional application No. 61/939,640, filed on Feb. 13, 2014.

(51) Int. Cl.
*C07D 413/06* (2006.01)
*A61K 31/506* (2006.01)
*A61K 31/513* (2006.01)

(52) U.S. Cl.
CPC ............ *C07D 413/06* (2013.01); *A61K 31/506* (2013.01); *A61K 31/513* (2013.01)

(58) Field of Classification Search
CPC ... C07D 413/06; A61K 31/506; A61K 31/513
USPC ................. 544/490; 514/211.05; 540/490
See application file for complete search history.

(56) References Cited

FOREIGN PATENT DOCUMENTS

WO WO-2013/006485 A1 1/2013

OTHER PUBLICATIONS

Belardinelli et al., A Novel, Potent, and Selective Inhibitor of Cardiac Late Sodium Current Suppresses Experimental Arrhythmias, The Journal of Pharmacology and Experimental Therapeutics, 344, pp. 23-32, Jan. 2013.*
Caira (1998) "Crystalline Polymorphism of Organic Compounds" *Topics in Current Chemistry*, Springer, Berlin, DE 198:163-208.
International Search Report—Written Opinion dated Feb. 13, 2014 for PCT/US2015/015652.

* cited by examiner

*Primary Examiner* — Deepak Rao
(74) *Attorney, Agent, or Firm* — Francis O. Ginah

(57) ABSTRACT

Crystalline solid forms of the selective late sodium current inhibitor 4-(pyrimidin-2-ylmethyl)-7-(4-(trifluoromethoxy)phenyl)-3,4-dihydrobenzo[f][1,4]oxazepin-5(2H)-one (Compound I) were prepared and characterized in the solid state:

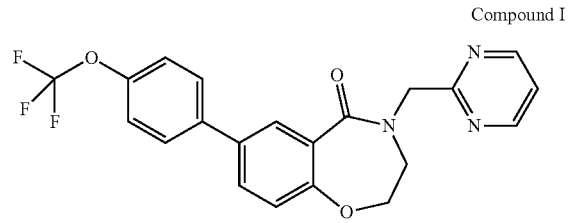

Compound I

Also provided are processes of manufacture and methods of using the crystalline forms.

31 Claims, 59 Drawing Sheets a)

b)

US 9,273,038 B2

SOLID FORMS OF AN ION CHANNEL MODULATOR

CROSS-REFERENCE TO RELATED APPLICATIONS

This application claims benefit under 35 U.S.C. §119(e) to U.S. Provisional Application Ser. No. 61/939,640, filed on Feb. 13, 2014, the entirety of which is incorporated herein by reference.

BACKGROUND

The present disclosure relates generally to crystalline solid forms of the compound 4-(pyrimidin-2-ylmethyl)-7-(4-(trifluoromethoxy)phenyl)-3,4-dihydrobenzo[f][1,4]oxazepin-5 (2H)-one, processes for making the forms, and their therapeutic methods of use.

The late sodium current (INaL) is a sustained component of the fast Na+ current of cardiac myocytes and neurons. Many common neurological and cardiac conditions are associated with abnormal INaL enhancement, which contributes to the pathogenesis of both electrical and contactile dysfunction in mammals. See, for example, Pathophysiology and Pharmacology of the Cardiac "Late Sodium Current", Pharmacology and Therapeutics 119 (2008) 326-339. Accordingly, compounds that selectively inhibit INaL in mammals may therefore be useful in treating such disease states. Such conditions include, but are not limited to, atrial fibrillation, diabetes, long QT syndrome, and hypertrophic cardiomyopathy.

The compound 4-(pyrimidin-2-ylmethyl)-7-(4-(trifluoromethoxy)phenyl)-3,4-dihydrobenzo[f][1,4]oxazepin-5 (2H)-one, designated herein as Compound I, is known to be a selective late sodium current inhibitor, as described for example in WO 2013/006485.

SUMMARY

The present disclosure provides crystalline forms of 4-(pyrimidin-2-ylmethyl)-7-(4-(trifluoromethoxy)phenyl)-3,4-dihydrobenzo[f][1,4]oxazepin-5(2H)-one (Compound I, below), including hydrates and solvates thereof. The disclosure also provides processes for making the crystalline forms and methods for using them in the treatment of neurological and cardiac conditions associated with abnormal INaL enhancement.

Compound I

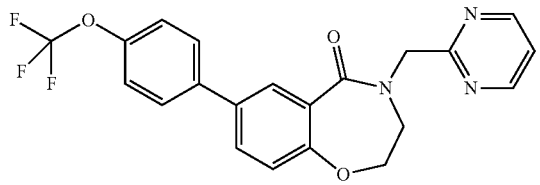

Thus, one embodiment is crystalline 4-(pyrimidin-2-ylmethyl)-7-(4-(trifluoromethoxy)phenyl)-3,4-dihydrobenzo[f][1,4]oxazepin-5(2H)-one (Compound I Form I), characterized by an X-ray powder diffractogram comprising the following peaks: 12.3, 23.8, and 27.2°2θ±0.2°2θ, as determined on a diffractometer using Cu-Kα radiation at a wavelength of 1.5406 Å.

Another embodiment is crystalline 4-(pyrimidin-2-ylmethyl)-7-(4-(trifluoromethoxy)phenyl)-3,4-dihydrobenzo[f][1,4]oxazepin-5(2H)-one (Compound I Form II), characterized by an X-ray powder diffractogram comprising the following peaks: 15.7, 17.5, and 20.3°2θ±0.2°2θ, as determined on a diffractometer using Cu-Kα radiation at a wavelength of 1.5406 Å.

Another embodiment is crystalline 4-(pyrimidin-2-ylmethyl)-7-(4-(trifluoromethoxy)phenyl)-3,4-dihydrobenzo[f][1,4]oxazepin-5(2H)-one (Compound I Form III), characterized by an X-ray powder diffractogram comprising the following peaks: 13.6, 20.6, and 24.1°2θ±0.2°2θ, as determined on a diffractometer using Cu-Kα radiation at a wavelength of 1.5406 Å.

Another embodiment is crystalline 4-(pyrimidin-2-ylmethyl)-7-(4-(trifluoromethoxy)phenyl)-3,4-dihydrobenzo[f][1,4]oxazepin-5(2H)-one methanesulfonic acid (Compound I Form IV or Compound I MSA Form I) characterized by an X-ray powder diffractogram comprising the following peaks: 16.5, 18.9, and 20.6°2θ±0.2°2θ, as determined on a diffractometer using Cu-Kα radiation at a wavelength of 1.5406 Å.

Another embodiment is crystalline 4-(pyrimidin-2-ylmethyl)-7-(4-(trifluoromethoxy)phenyl)-3,4-dihydrobenzo[f][1,4]oxazepin-5(2H)-one benzene sulfonic acid (Compound I Form V or Compound I BSA Form I) characterized by an X-ray powder diffractogram comprising the following peaks: 8.0, 8.6, and 13.9°2θ±0.2°2θ, as determined on a diffractometer using Cu-Kα radiation at a wavelength of 1.5406 Å.

An additional embodiment is crystalline 4-(pyrimidin-2-ylmethyl)-7-(4-(trifluoromethoxy)phenyl)-3,4-dihydrobenzo[f][1,4]oxazepin-5 (2H)-one benzene sulfonic acid (Compound I Form VI or Compound I BSA Form II) characterized by an X-ray powder diffractogram comprising the following peaks: 4.0, 14.7, and 17.9°2θ±0.2°2θ, as determined on a diffractometer using Cu-Kα radiation at a wavelength of 1.5406 Å.

Another embodiment is crystalline 4-(pyrimidin-2-ylmethyl)-7-(4-(trifluoromethoxy)phenyl)-3,4-dihydrobenzo[f][1,4]oxazepin-5(2H)-one p-toluenesulfonic acid (Compound I Form VII or Compound I p-TSA Form I), characterized by an X-ray powder diffractogram comprising the following peaks: 5.4, 18.2, and 18.8°2θ±0.2°2θ, as determined on a diffractometer using Cu-Kα radiation at a wavelength of 1.5406 Å.

Yet another embodiment is crystalline 4-(pyrimidin-2-ylmethyl)-7-(4-(trifluoromethoxy)phenyl)-3,4-dihydrobenzo[f][1,4]oxazepin-5(2H)-one p-toluenesulfonic acid (Compound I Form VIII or Compound I p-TSA Form II), characterized by an X-ray powder diffractogram comprising the following peaks: 6.2, 15.3, and 18.4°2θ±0.2°2θ, as determined on a diffractometer using Cu-Kα radiation at a wavelength of 1.5406 Å.

Yet another embodiment is crystalline 4-(pyrimidin-2-ylmethyl)-7-(4-(trifluoromethoxy)phenyl)-3,4-dihydrobenzo[f][1,4]oxazepin-5(2H)-one p-toluenesulfonic acid (Compound I Form IX or Compound I p-TSA Form III), characterized by an X-ray powder diffractogram comprising the following peaks: 5.9, 8.9, and 17.7°2θ±0.2°2θ, as determined on a diffractometer using Cu-Kα radiation at a wavelength of 1.5406 Å.

Sill a further embodiment is crystalline 4-(pyrimidin-2-ylmethyl)-7-(4-(trifluoromethoxy)phenyl)-3,4-dihydrobenzo[f][1,4]oxazepin-5(2H)-one p-toluenesulfonic acid (Compound I Form X or Compound I p-TSA Form IV), characterized by an X-ray powder diffractogram comprising the following peaks: 5.2, 15.5, and 18.1°2θ±0.2°2θ, as determined on a diffractometer using Cu-Kα radiation at a wavelength of 1.5406 Å.

Yet another embodiment is crystalline 4-(pyrimidin-2-ylmethyl)-7-(4-(trifluoromethoxy)phenyl)-3,4-dihydrobenzo[f][1,4]oxazepin-5(2H)-one HCl (Compound I Form XI or Compound I HCl Form I), characterized by an X-ray powder diffractogram comprising the following peaks: 14.1, 16.7, and 19.0°2θ±0.2°2θ, as determined on a diffractometer using Cu-Kα radiation at a wavelength of 1.5406 Å.

Another embodiment is crystalline 4-(pyrimidin-2-ylmethyl)-7-(4-(trifluoromethoxy)phenyl)-3,4-dihydrobenzo[f][1,4]oxazepin-5(2H)-one HCl (Compound I Form XII or Compound I HCl Form II), characterized by an X-ray powder diffractogram comprising the following peaks: 16.5, 18.4, and 20.7°2θ±0.2°2θ, as determined on a diffractometer using Cu-Kα radiation at a wavelength of 1.5406 Å.

Another embodiment is crystalline 4-(pyrimidin-2-ylmethyl)-7-(4-(trifluoromethoxy)phenyl)-3,4-dihydrobenzo[f][1,4]oxazepin-5(2H)-one HCl (Compound I Form XIII or Compound I HCl Form III), characterized by an X-ray powder diffractogram comprising the following peaks: 18.8, 20.9, and 22.6°2θ±0.2°2θ, as determined on a diffractometer using Cu-Kα radiation at a wavelength of 1.5406 Å.

Another embodiment is crystalline 4-(pyrimidin-2-ylmethyl)-7-(4-(trifluoromethoxy)phenyl)-3,4-dihydrobenzo[f][1,4]oxazepin-5(2H)-one mono sulfate (Compound I Form XIV or Compound I Sulfate Form I), characterized by an X-ray powder diffractogram comprising the following peaks: 3.7, 16.2, 18.9, 20.0, 20.3, and 23.8°±0.2°2θ, as determined on a diffractometer using Cu-Kα radiation at a wavelength of 1.5406 Å.

Another embodiment is crystalline 4-(pyrimidin-2-ylmethyl)-7-(4-(trifluoromethoxy)phenyl)-3,4-dihydrobenzo[f][1,4]oxazepin-5(2H)-one mono sulfate (Compound I Form XV or Compound I Sulfate Form II), characterized by an X-ray powder diffractogram comprising the following peaks: 4.3, 19.1, 19.3, 20.4, 21.4, 21.7, 22.1, and 22.6°±0.2 2θ, as determined on a diffractometer using Cu-Kα radiation at a wavelength of 1.5406 Å.

Another embodiment is crystalline 4-(pyrimidin-2-ylmethyl)-7-(4-(trifluoromethoxy)phenyl)-3,4-dihydrobenzo[f][1,4]oxazepin-5(2H)-one esylate (Compound I Form XVI or Compound I Esylate Form I), characterized by an X-ray powder diffractogram comprising the following peaks: 14.9, 16.4, 18.9, and 27.0°±0.2°2θ, as determined on a diffractometer using Cu-Kα radiation at a wavelength of 1.5406 Å.

Another embodiment is crystalline 4-(pyrimidin-2-ylmethyl)-7-(4-(trifluoromethoxy)phenyl)-3,4-dihydrobenzo[f][1,4]oxazepin-5(2H)-one edisylate (Compound I Form XVII or Compound I Edisylate Form I), characterized by an X-ray powder diffractogram comprising the following peaks: 4.3, 10.2, 19.0, 22.2, and 22.7°±0.2°2θ, as determined on a diffractometer using Cu-Kα radiation at a wavelength of 1.5406 Å.

Another embodiment is crystalline 4-(pyrimidin-2-ylmethyl)-7-(4-(trifluoromethoxy)phenyl)-3,4-dihydrobenzo[f][1,4]oxazepin-5(2H)-one oxalate (Compound I Form XVIII or Compound I Oxalate Form I), characterized by an X-ray powder diffractogram comprising the following peaks: 15.5, 19.5, and 25.7°±0.2°2θ, as determined on a diffractometer using Cu-Kα radiation at a wavelength of 1.5406 Å.

In another aspect, is a composition comprising any one of Compound I Forms I to XVIII.

In one embodiment, the composition comprises a Compound Form I, Form II or Form III.

In another embodiment, the composition is a formulation as defined herein.

Additionally, the disclosure provides in one embodiment a method for treating a subject suffering from a neurological and/or cardiac condition associated with abnormal INaL enhancement. Such conditions include, but are not limited to, atrial fibrillation, diabetes, long QT syndrome, and hypertrophic cardiomyopathy. The method comprises administering to the subject a therapeutically effective amount of any one of Compound I Forms I to XVIII, as described generally above.

Another embodiment is the use of any one of Compound I Forms I to XVIII for treating a neurological and/or cardiac condition associated with abnormal INaL enhancement.

Still an additional embodiment is the use of any one of Compound I Forms I to XVIII in the manufacture of a medicament for a neurological and/or cardiac condition associated with abnormal INaL enhancement (including, but not limited to, atrial fibrillation, diabetes, long QT syndrome, and hypertrophic cardiomyopathy).

DETAILED DESCRIPTION

Figure 1:
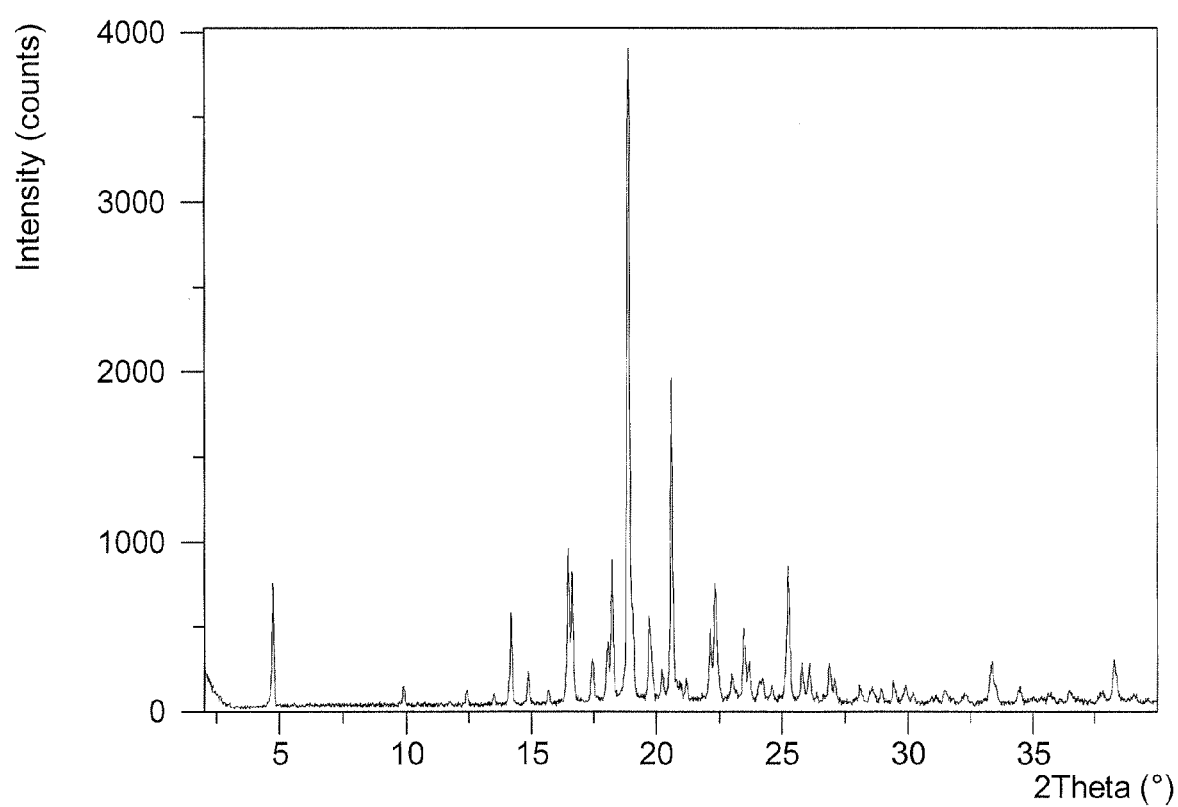
FIG. 1 shows an X-ray powder diffraction (XRPD) of Compound I Form IV.

The compound 4-(pyrimidin-2-ylmethyl)-7-(4-(trifluoromethoxy)phenyl)-3,4-dihydrobenzo[f][1,4]oxazepin-5 (2H)-one (Compound I) is a selective and potent late sodium current inhibitor.

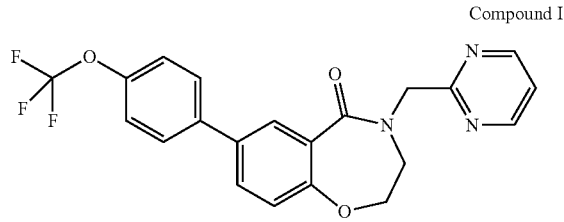 [SMILES: O=C1c2cc(-c3ccc(OC(F)(F)F)cc3)ccc2OCCN1Cc1ncccn1]

Compound I

The present invention results from the surprising discoveries of crystalline forms of Compound I, advantages attributed to the forms as described herein, such as physical and chemical properties which may enable development of a robust and scalable process, and processes for making the crystalline forms.

DEFINITIONS

As used in the present specification, the following words and phrases are generally intended to have the meanings as set forth below, except to the extent that the context in which they are used indicates otherwise.

The term "solvate" refers to a complex formed by the combining of Compound I and a solvent.

The term "co-crystal" refers to a crystalline material formed by combining a compound of Formula I, or any Formula disclosed herein and one or more co-crystal formers (i.e., a molecule, ion or atom). In certain instances, co-crystals may have improved properties as compared to the parent form (i.e., the free molecule, zwitterion, etc.) or a salt of the parent compound. Improved properties may be increased solubility, increased dissolution, increased bioavailability, increased dose response, decreased hygroscopicity, a crystalline form of a normally amorphous compound, a crystalline form of a difficult to salt or unsaltable compound, decreased form diversity, more desired morphology, and the like. Methods for making and characterizing co-crystals are known to those of skill in the art.

The term hydrate refers to a crystalline material that includes certain whole or fractional mole equivalents of water in the crystal lattice. Conversely, the term anhydrous as used herein means a crystalline material as described herein wherein there is none or essentially no amount of water (i.e. less than 5%) in the crystal lattice.

The term "therapeutically effective amount" refers to an amount that is sufficient to effect treatment, as defined below, when administered to a mammal in need of such treatment. The therapeutically effective amount will vary depending upon the subject being treated, the weight and age of the subject, the severity of the disease condition, the manner of administration and the like, which may readily be determined by one of ordinary skill in the art.

In addition, abbreviations as used herein have respective meanings as follows:

| | |
|---|---|
| μL | Microliter |
| Å | Angstrom |
| Ac | Acetate |
| ACN | Acetonitrile |
| AN | Area normalized |
| AUC | Area under the curve |
| Aw | Water activity |
| BSA | Benzene sulfonic acid |
| CF | Co-former |
| DCM | dichloromethane |
| DI | Deionized |
| DSC | Differential Scanning Calorimetry |
| DVS | Dynamic vapor sorption |
| eq. | Equivalents |
| Et | Ethyl |
| g | Gram |
| h | Hour |
| HPLC | High Performance Liquid Chromatography |
| INaL | Late Na+ Current |
| IPA | Isopropyl alcohol |
| IPAc | Isopropyl acetate |
| IPE | Diisopropyl ether |
| iPr | Isopropyl |
| KF | Karl Fischer |
| kV | Kilovolts |
| M | Molar |
| m.p. | Melting point |
| mA | Milliamps |
| Me | Methyl |
| MEK | methyl ethyl ketone |
| mg | Milligram |
| MIBK | methyl iso-butyl ketone |
| min | Minute |
| mL | Milliliter |
| MSA | Methanesulfonic acid |
| MTBE | methyl tert-butyl ether |
| n/a | Not analyzed |
| NA | Data not available |
| NDSA | 1,5-Naphthalene-di-sulfonic acid |
| NMR | Nuclear magnetic resonance |
| o/n | Overnight |
| p-TSA | para-Toluenesulfonic acid |
| RH | Relative humidity |
| RT | Room temperature |
| s | Second |
| sat'd | Saturated |
| t | Time |
| TGA | Thermogravimetric analysis |
| THF | Tetrahydrofuran |
| v | Volume |
| w | Weight |
| wt % | Weight percent |
| XRPD/pXRD | X-ray powder diffraction |

Solid Forms of Compound I

As described generally above, the present disclosure provides solid crystalline forms of Compound I and Compound I salts/co-crystals, which are designated as Forms I to XVIII.

Crystalline 4-(pyrimidin-2-ylmethyl)-7-(4-(trifluoromethoxy)phenyl)-3,4-dihydrobenzo[f][1,4]oxazepin-5(2H)-one methanesulfonic acid (Compound I Form IV) is characterized by its X-ray powder diffractogram that comprises peaks at 16.5, 18.9, and 20.6°2θ±0.2°2θ, as determined on a diffractometer using Cu-Kα radiation at a wavelength of 1.5406 Å. The diffractogram comprises additional peaks at 4.8, 14.2, and 19.7°2θ±0.2°2θ. Compound I Form IV is also characterized by its full X-ray powder diffractogram as substantially shown in FIG. 1.

Figure 2:
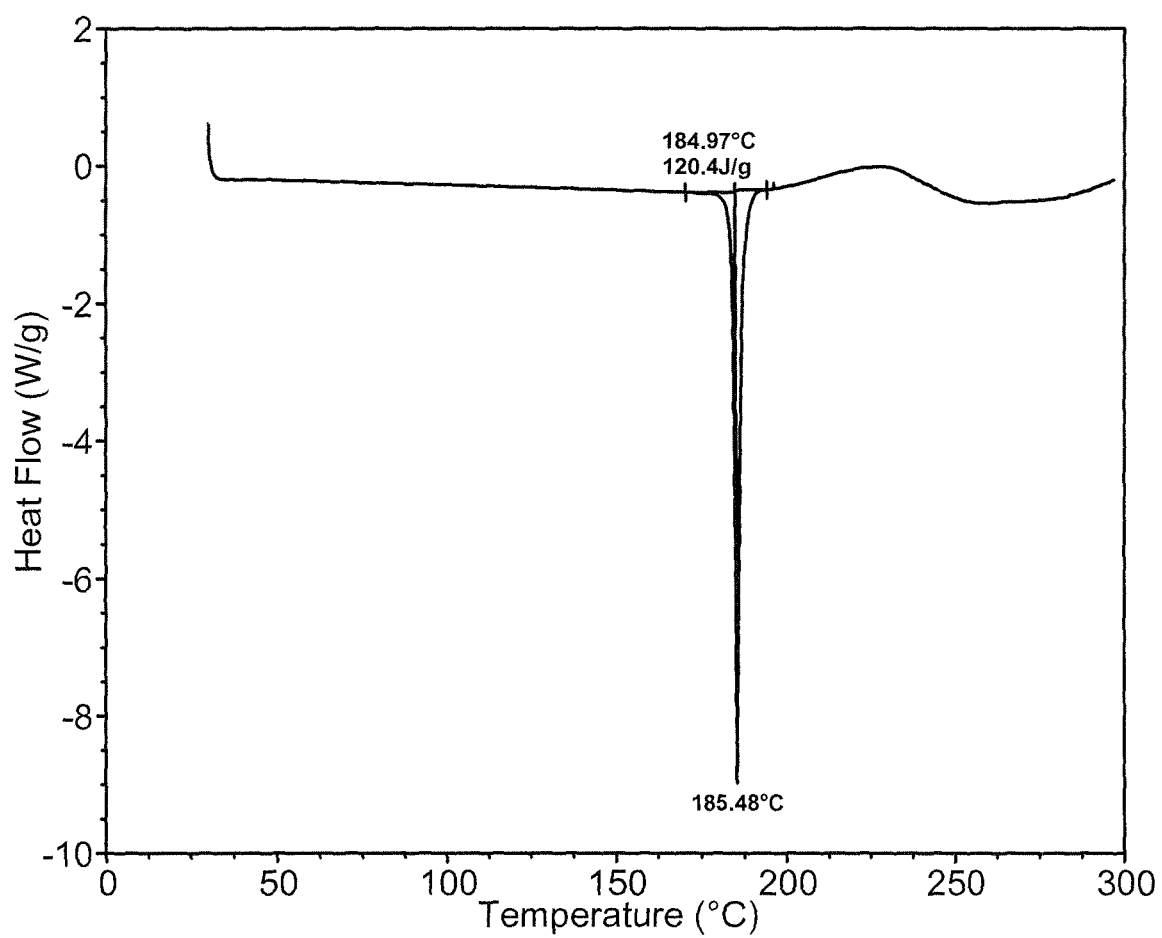
FIG. 2 shows a differential scanning calorimeter (DSC) curve of Compound I Form IV.

In some embodiments, Compound I Form IV is characterized by its differential scanning calorimetry (DSC) curve that comprises an endotherm at about 185° C. Compound I Form IV also is characterized by its full DSC curve as substantially as shown in FIG. 2.

In one embodiment, Compound I Form IV is the methanesulfonic acid salt. In another embodiment, Compound I Form IV is the methanesulfonic acid co-crystal.

Crystalline 4-(pyrimidin-2-ylmethyl)-7-(4-(trifluoromethoxy)phenyl)-3,4-dihydrobenzo[f][1,4]oxazepin-5(2H)-one benzene sulfonic acid (Compound I Form V) is characterized by its X-ray powder diffractogram that comprises peaks at 8.0, 8.6, and 13.9°2θ±0.2°2θ, as determined on a diffractometer using Cu-Kα radiation at a wavelength of 1.5406 Å. The diffractogram comprises additional peaks at 17.1, 18.9, and 20.1°2θ±0.2°2θ. Compound I Form V is also characterized by its full X-ray powder diffractogram as substantially shown in FIG. 5.

Figure 6:
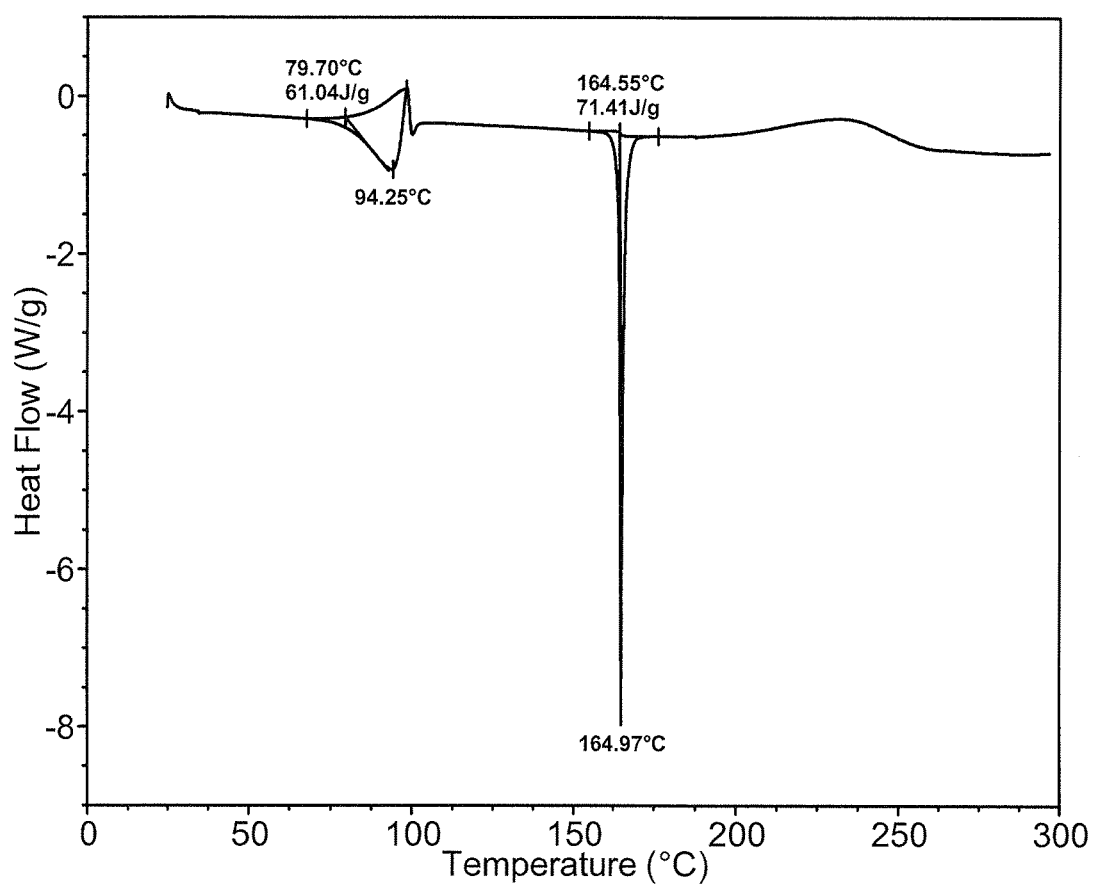
FIG. 6 shows a differential scanning calorimeter (DSC) curve of Compound I Form V.

In some embodiments, Compound I Form V is characterized by its differential scanning calorimetry (DSC) curve that comprises an endotherm at about 80° C. and an endotherm at about 165° C. Compound I Form V also is characterized by its full DSC curve as substantially as shown in FIG. 6.

In one embodiment, Compound I Form V is the benzene sulfonic acid salt. In another embodiment, Compound I Form V is the benzene sulfonic acid co-crystal.

Crystalline 4-(pyrimidin-2-ylmethyl)-7-(4-(trifluoromethoxy)phenyl)-3,4-dihydrobenzo[f][1,4]oxazepin-5(2H)-one benzene sulfonic acid (Compound I Form VI) is characterized by its X-ray powder diffractogram that comprises peaks at 4.0, 14.7, and 17.9°2θ±0.2°2θ, as determined on a diffractometer using Cu-Kα radiation at a wavelength of 1.5406 Å. The diffractogram comprises additional peaks at 7.9, 9.3, and 9.9°2θ±0.2°2θ. Compound I Form VI is also characterized by its full X-ray powder diffractogram as substantially shown in FIG. 8.

Figure 9:
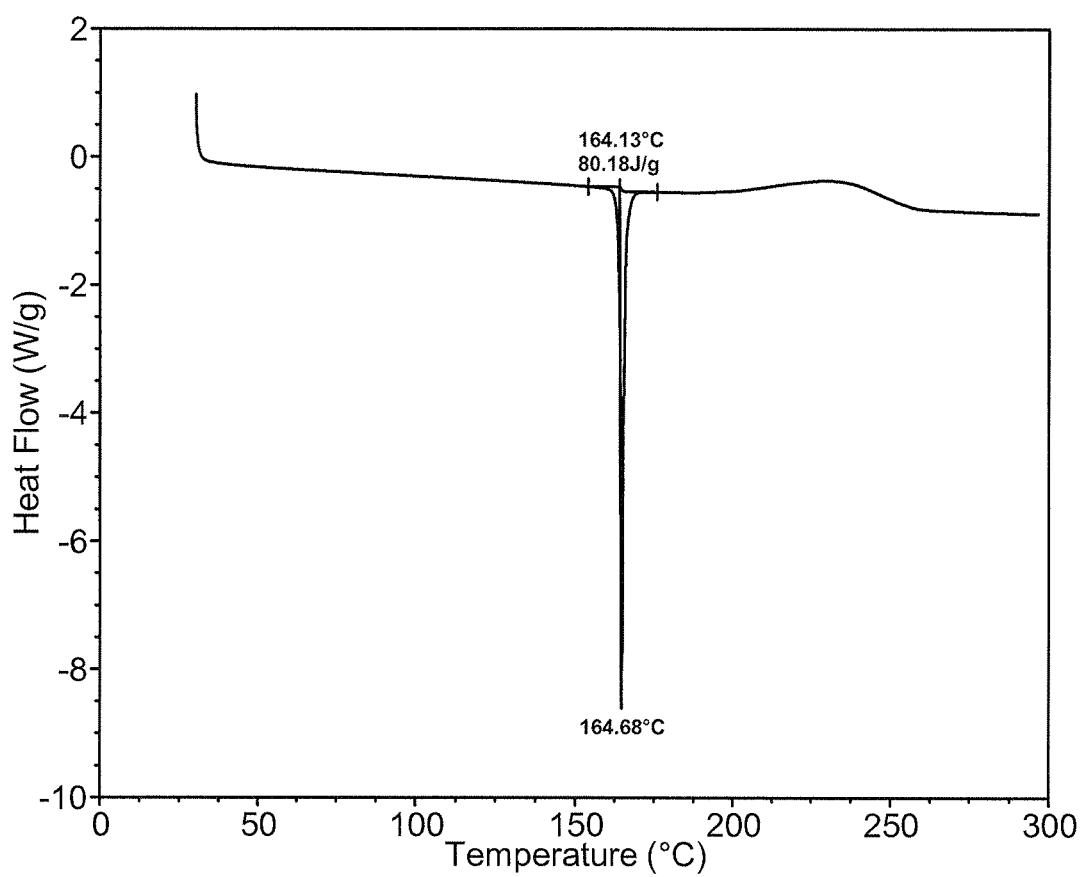
FIG. 9 shows a differential scanning calorimeter (DSC) curve of Compound I Form VI.

In some embodiments, Compound I Form VI is characterized by its differential scanning calorimetry (DSC) curve that comprises an endothelial at about 164° C. Compound I Form VI also is characterized by its full DSC curve as substantially as shown in FIG. 9.

In one embodiment, Compound I Form VI is the benzene sulfonic acid salt. In another embodiment, Compound I Form VI is the benzene sulfonic acid co-crystal.

Crystalline 4-(pyrimidin-2-ylmethyl)-7-(4-(trifluoromethoxy)phenyl)-3,4-dihydrobenzo[f][1,4]oxazepin-5 (2H)-one p-toluenesulfonic acid (Compound I Form VII) is characterized by its X-ray powder diffractogram that comprises peaks at 5.4, 18.2, and 18.8°2θ±0.2°2θ, as determined on a diffractometer using Cu-Kα radiation at a wavelength of 1.5406 Å. The diffractogram comprises additional peaks at 8.1 and 15.5°2θ±0.2°2θ. Compound I Form VII is also characterized by its full X-ray powder diffractogram as substantially shown in FIG. 12.

Figure 13:
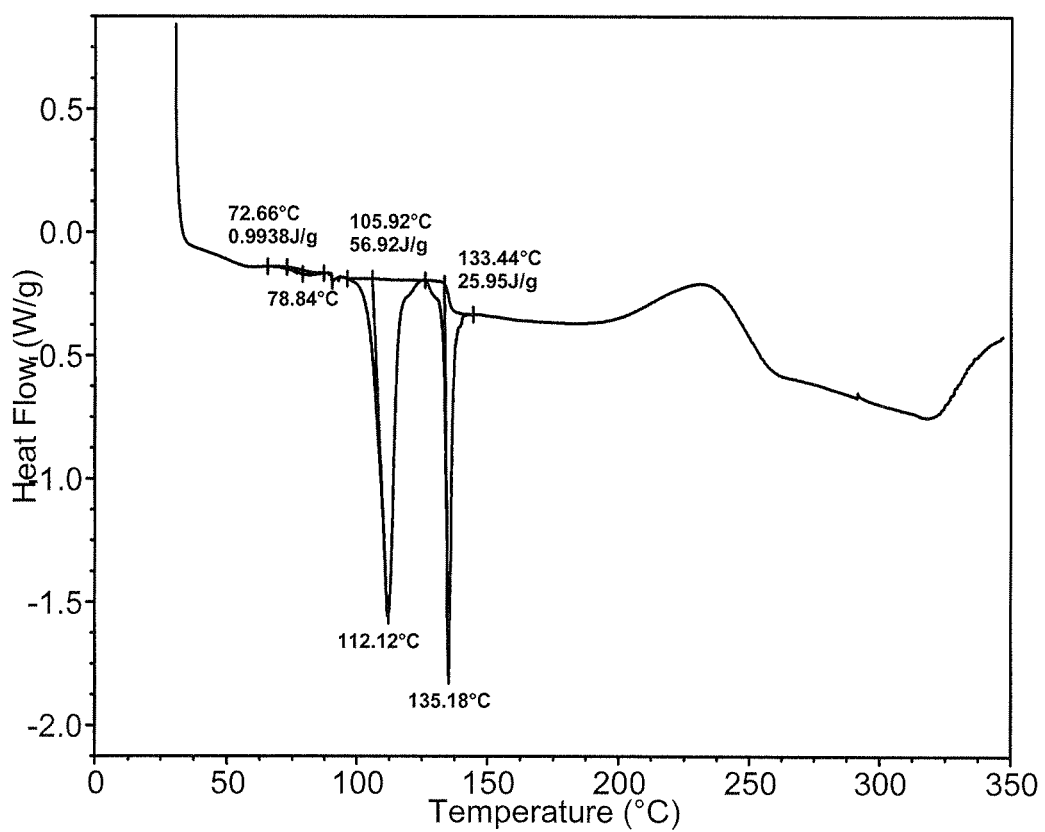
FIG. 13 shows a differential scanning calorimeter (DSC) curve of Compound I Form VII.

In some embodiments, Compound I Form VII is characterized by its differential scanning calorimetry (DSC) curve that comprises an endotherm at about 106° C. and an endotherm at about 133° C. Compound I Form VII also is characterized by its full DSC curve as substantially as shown in FIG. 13.

In one embodiment, Compound I Form VII is the p-toluenesulfonic acid salt. In another embodiment, Compound I Form VII is the p-toluenesulfonic acid co-crystal.

Crystalline 4-(pyrimidin-2-ylmethyl)-7-(4-(trifluoromethoxy)phenyl)-3,4-dihydrobenzo[f][1,4]oxazepin-5 (2H)-one p-toluenesulfonic acid (Compound I Form VIII) is characterized by its X-ray powder diffractogram that comprises peaks at 6.2, 15.3, and 18.4°2θ±0.2°2θ, as determined on a diffractometer using Cu-Kα radiation at a wavelength of 1.5406 Å. The diffractogram comprises additional peaks at 3.1, 5.3, and 9.2°2θ±0.2°2θ. Compound I Form VIII is also characterized by its full X-ray powder diffractogram as substantially shown in FIG. 16.

Figure 17:
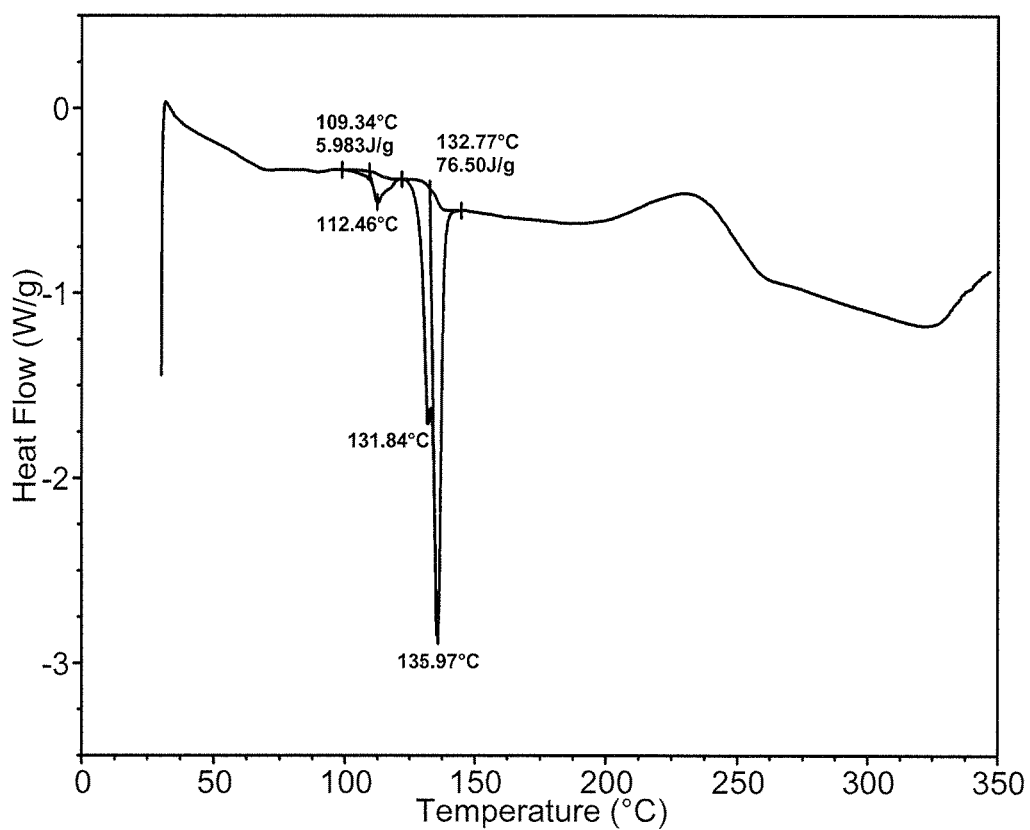
FIG. 17 shows a differential scanning calorimeter (DSC) curve of Compound I Form VIII.

In some embodiments, Compound I Form VIII is characterized by its differential scanning calorimetry (DSC) curve that comprises an endotherm at about 109° C. and an endotherm at about 132° C. Compound I Form VIII also is characterized by its full DSC curve as substantially as shown in FIG. 17.

In one embodiment, Compound I Form VIII is the p-toluenesulfonic acid salt. In another embodiment, Compound I Form VIII is the p-toluenesulfonic acid co-crystal.

Crystalline 4-(pyrimidin-2-ylmethyl)-7-(4-(trifluoromethoxy)phenyl)-3,4-dihydrobenzo[f][1,4]oxazepin-5 (2H)-one p-toluenesulfonic acid (Compound I Form IX) is characterized by its X-ray powder diffractogram that comprises peaks at 5.9, 8.9, and 17.7°2θ±0.2°2θ, as determined on a diffractometer using Cu-Kα radiation at a wavelength of 1.5406 Å. The diffractogram comprises additional peaks at 3.0, 11.8, and 14.8°2θ±0.2°2θ. Compound I Form IX is also characterized by its full X-ray powder diffractogram as substantially shown in FIG. 18.

Figure 19:
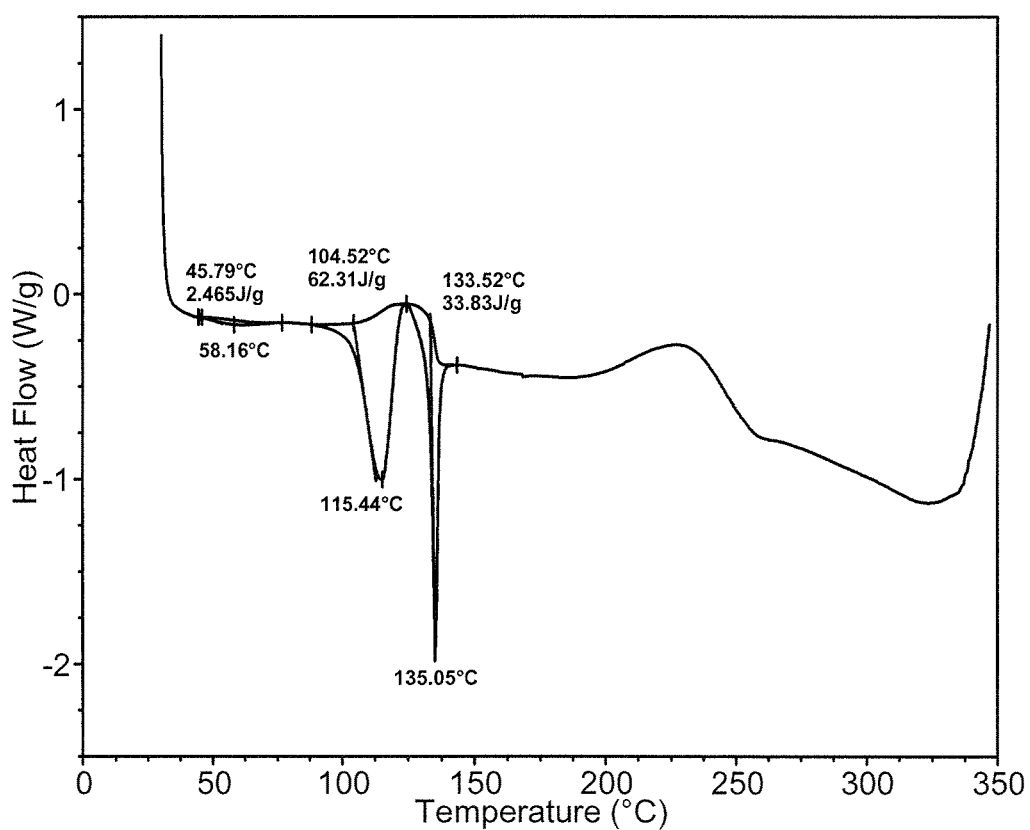
FIG. 19 shows a differential scanning calorimeter (DSC) curve of Compound I Form IX.

In some embodiments, Compound I Form IX is characterized by its differential scanning calorimetry (DSC) curve that comprises an endotherm at about 105° C. and an endotherm at about 134° C. Compound I Form IX also is characterized by its full DSC curve as substantially as shown in FIG. 19.

In one embodiment, Compound I Form IX is the p-toluenesulfonic acid salt. In another embodiment, Compound I Form IX is the p-toluenesulfonic acid co-crystal.

Crystalline 4-(pyrimidin-2-ylmethyl)-7-(4-(trifluoromethoxy)phenyl)-3,4-dihydrobenzo[f][1,4]oxazepin-5 (2H)-one p-toluenesulfonic acid (Compound I Form X) is characterized by its X-ray powder diffractogram that comprises peaks at 5.2, 15.5, and 18.1°2θ±2θ, as determined on a diffractometer using Cu-Kα radiation at a wavelength of 1.5406 Å. The diffractogram comprises additional peaks at 7.8 and 10.5°2θ±0.2°2θ. Compound I Form X is also characterized by its full X-ray powder diffractogram as substantially shown in FIG. 21.

Figure 22:
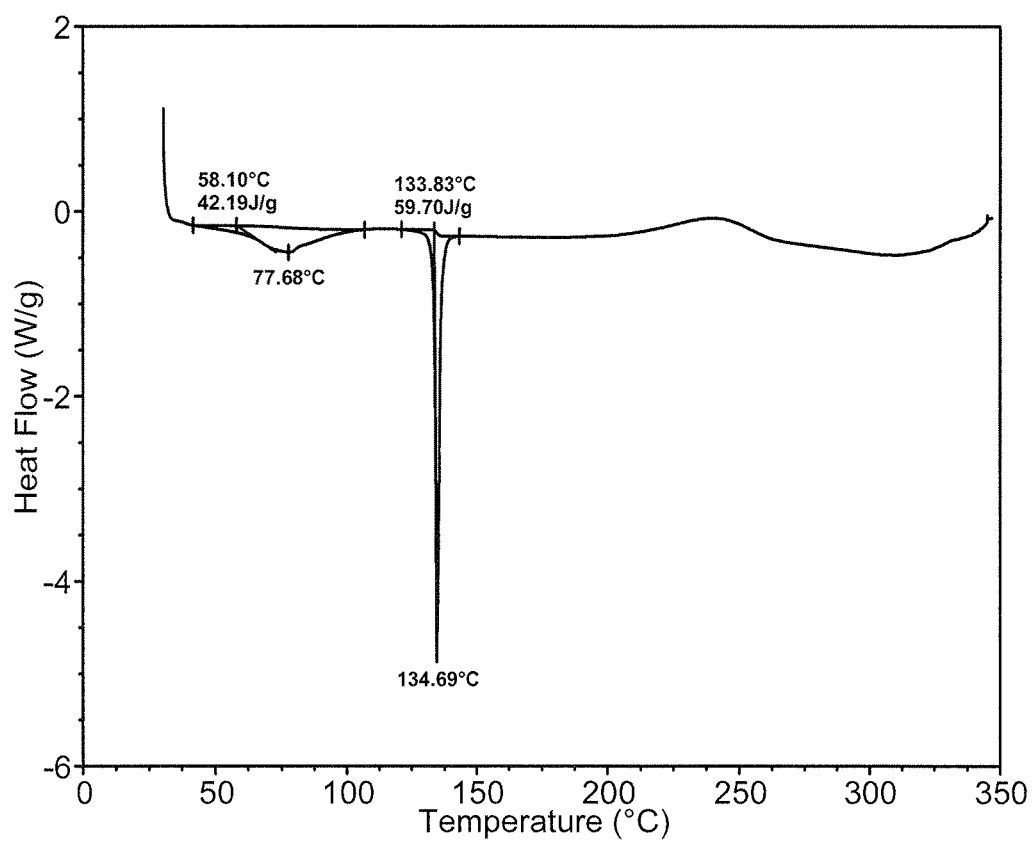
FIG. 22 shows a differential scanning calorimeter (DSC) curve of Compound I Form X.

In some embodiments, Compound I Form X is characterized by its differential scanning calorimetry (DSC) curve that comprises an endotherm at about 58° C. and an endotherm at about 134° C. Compound I Form X also is characterized by its full DSC curve as substantially as shown in FIG. 22.

In one embodiment, Compound I Form X is the p-toluenesulfonic acid salt. In another embodiment, Compound I Form X is the p-toluenesulfonic acid co-crystal.

Crystalline 4-(pyrimidin-2-ylmethyl)-7-(4-(trifluoromethoxy)phenyl)-3,4-dihydrobenzo[f][1,4]oxazepin-5 (2H)-one HCl (Compound I Form XI) is characterized by its X-ray powder diffractogram that comprises peaks at 14.1, 16.7, and 19.0°2θ±0.2°2θ, as determined on a diffractometer using Cu-Kα radiation at a wavelength of 1.5406 Å. The diffractogram comprises additional peaks at 8.2, 18.3, and 20.2°2θ±0.2°2θ. Compound I Form XI is also characterized by its full X-ray powder diffractogram as substantially shown in FIG. 24.

Figure 25:
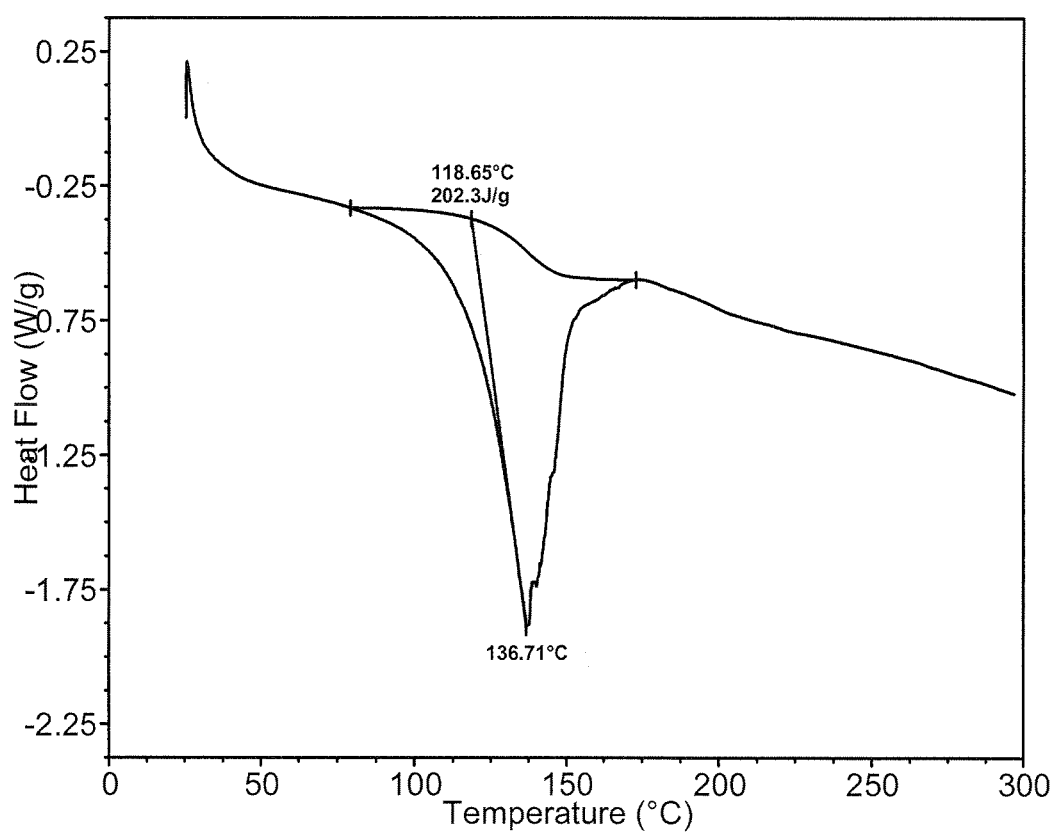
FIG. 25 shows a differential scanning calorimeter (DSC) curve of Compound I Form XI.

In some embodiments, Compound I Form. XI is characterized by its differential scanning calorimetry (DSC) curve that comprises an endotherm at about 119° C. Compound I Form XI also is characterized by its full DSC curve as substantially as shown in FIG. 25.

In one embodiment, Compound I Form XI is the HCl salt. In another embodiment, Compound I Form XI is the HCl co-crystal.

Crystalline 4-(pyrimidin-2-ylmethyl)-7-(4-(trifluoromethoxy)phenyl)-3,4-dihydrobenzo[f][1,4]oxazepin-5 (2H)-one HCl (Compound I Form XII) is characterized by its X-ray powder diffractogram that comprises peaks at 16.5, 18.4, and 20.7°2θ±0.2°2θ, as determined on a diffractometer using Cu-Kα radiation at a wavelength of 1.5406 Å. The diffractogram comprises additional peaks at 8.2, 13.7, and 15.0°2θ±0.2°2θ. Compound I Form XII is also characterized by its full X-ray powder diffractogram as substantially shown in FIG. 27.

Figure 28:
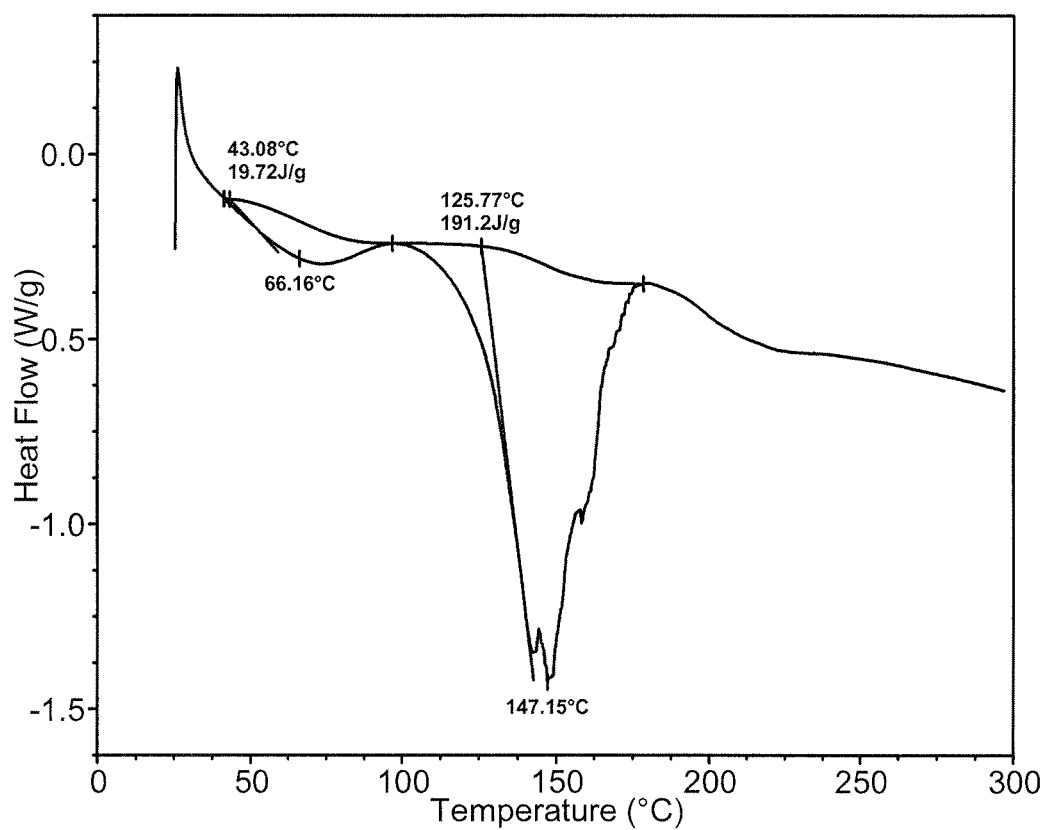
FIG. 28 shows a differential scanning calorimeter (DSC) curve of Compound I Form XII.

In some embodiments, Compound I Form XII is characterized by its differential scanning calorimetry (DSC) curve that comprises an endotherm at about 29° C. and an endotherm at about 126° C. Compound I Form XII also is characterized by its full DSC curve as substantially as shown in FIG. 28.

In one embodiment, Compound I Form XII is the HCl salt. In another embodiment, Compound I Form XII is the HCl co-crystal.

Crystalline 4-(pyrimidin-2-ylmethyl)-7-(4-(trifluoromethoxy)phenyl)-3,4-dihydrobenzo[f][1,4]oxazepin-5 (2H)-one HCl (Compound I Form XIII) is characterized by its X-ray powder diffractogram that comprises peaks at 18.8, 20.9, and 22.6°2θ±0.2°2θ, as determined on a diffractometer using Cu-Kα radiation at a wavelength of 1.5406 Å. The diffractogram comprises additional peaks at 12.5 and 16.7°2θ±0.2°2θ. Compound I Form XIII is also characterized by its full X-ray powder diffractogram as substantially shown in FIG. 30.

Figure 31:
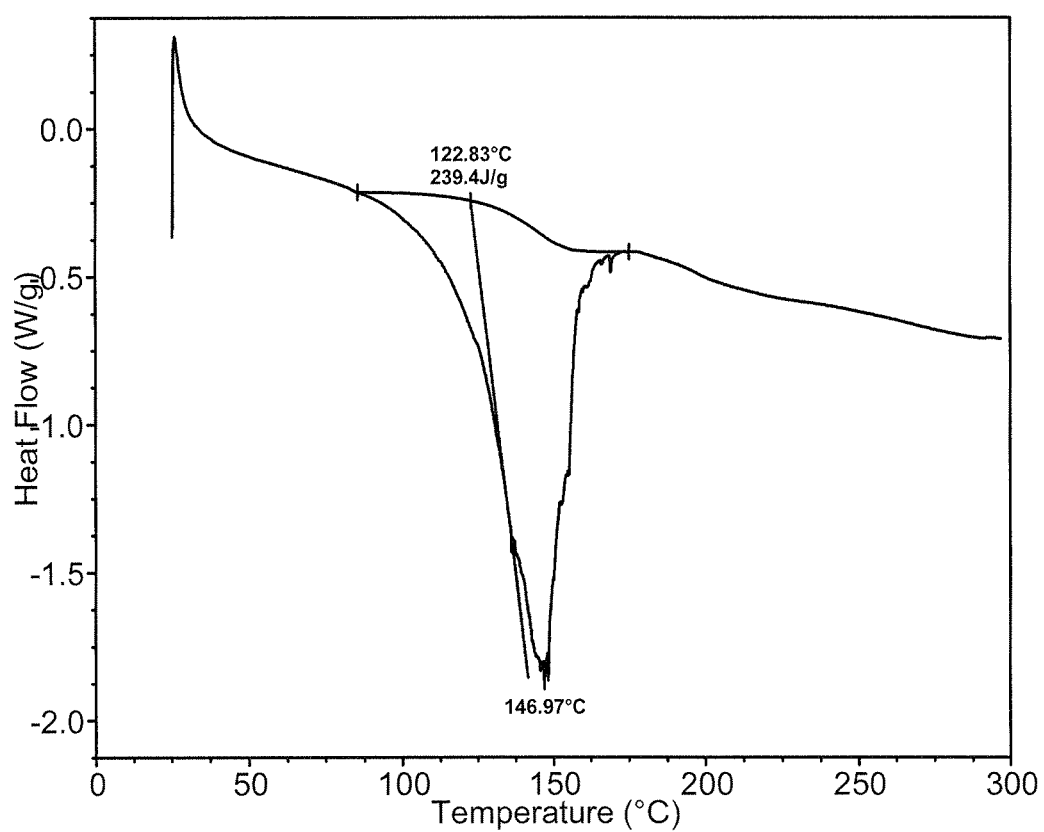
FIG. 31 shows a differential scanning calorimeter (DSC) curve of Compound I Form XIII.

In some embodiments, Compound I Form XIII is characterized by its differential scanning calorimetry (DSC) curve that comprises an endotherm at about 123 to 126° C. Compound I Form XIII also is characterized by its full DSC curve as substantially as shown in FIG. 31.

In one embodiment, Compound I Form XIII is the HCl salt. In another embodiment, Compound I Form XIII is the HCl co-crystal.

Crystalline 4-(pyrimidin-2-ylmethyl)-7-(4-(trifluoromethoxy)phenyl)-3,4-dihydrobenzo[f][1,4]oxazepin-5(2H)-one (Compound I Form I) is characterized by its X-ray powder diffractogram that comprises peaks at 12.3, 23.8, and 27.2°2θ±0.2°2θ, as determined on a diffractometer using Cu-Kα radiation at a wavelength of 1.5406 Å. In some embodiments, the diffractogram comprises an additional peak at 20.5°2θ±0.2°2θ. In other embodiments, the diffractogram comprises additional peaks at 20.5 and 20.7°2θ±0.2°2θ. Compound I Form I is also characterized by its full X-ray powder diffractogram as substantially shown in FIG. 33.

Figure 34:
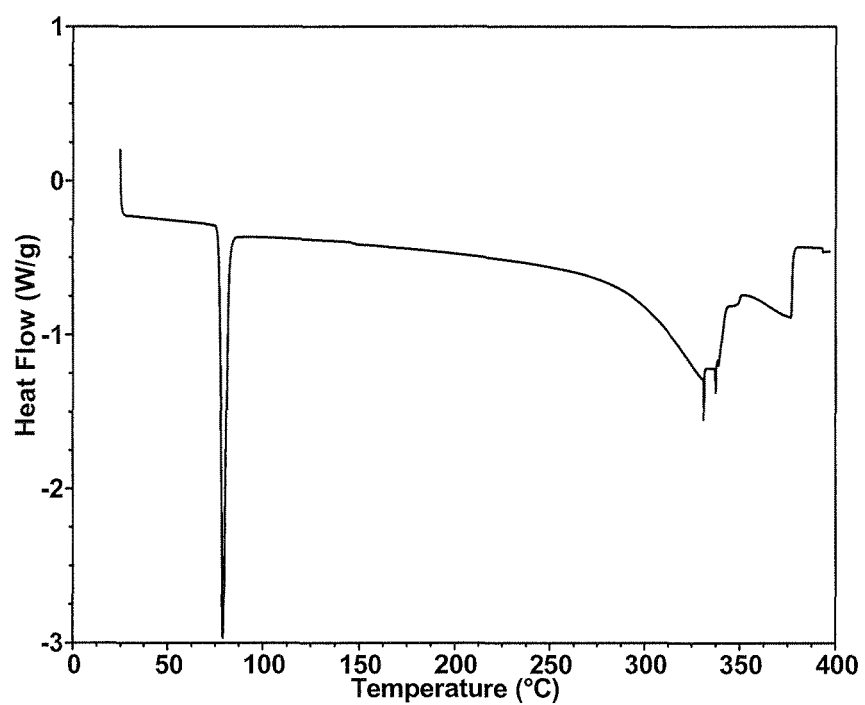
FIG. 34 shows a differential scanning calorimeter (DSC) curve of Compound I Form I.

In some embodiments, Compound I Form I is characterized by its differential scanning calorimetry (DSC) curve that comprises an endotherm at about 74 to 79° C. Compound I Form I also is characterized by its full DSC curve as substantially as shown in FIG. 34.

Crystalline 4-(pyrimidin-2-ylmethyl)-7-(4-(trifluoromethoxy)phenyl)-3,4-dihydrobenzo[f][1,4]oxazepin-5(2H)-one (Compound I Form II) is characterized by its X-ray powder diffractogram that comprises peaks at 15.7, 17.5, and 20.3°2θ±0.2°2θ, as determined on a diffractometer using Cu-Kα radiation at a wavelength of 1.5406 Å. The diffractogram comprises additional peaks at 11.7, 19.7, and 23.2°2θ±0.2°2θ. Compound I Form II is also characterized by its full X-ray powder diffractogram as substantially shown in FIG. 36.

Figure 37:
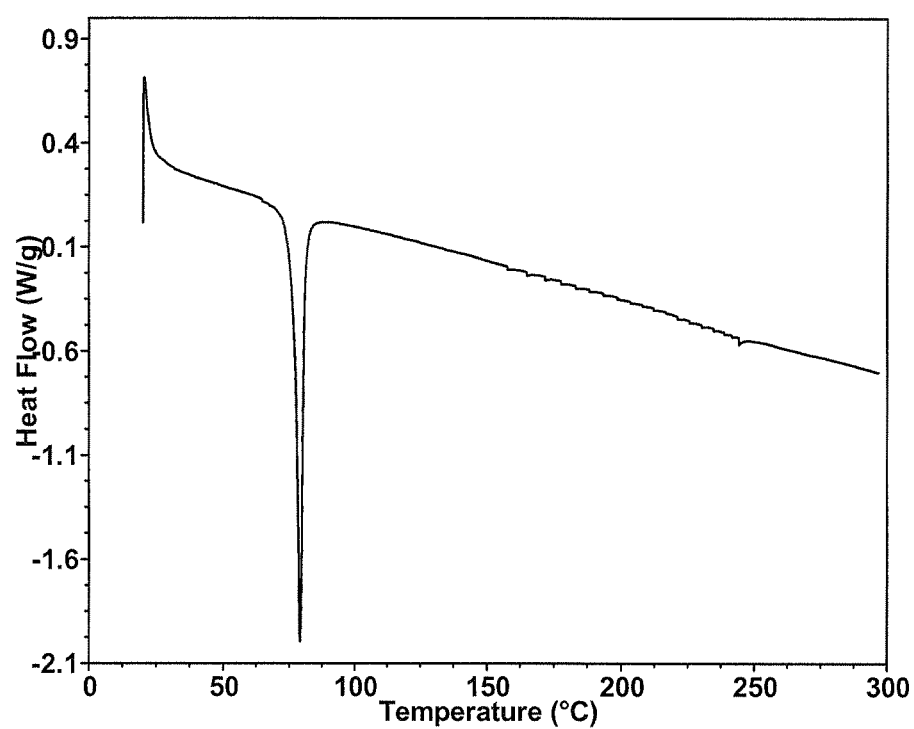
FIG. 37 shows a differential scanning calorimeter (DSC) curve of Compound I Form II.

In some embodiments, Compound I Form II is characterized by its differential scanning calorimetry (DSC) curve that comprises an endotherm at about 77° C. Compound I Form II also is characterized by its full DSC curve as substantially as shown in FIG. 37.

Crystalline 4-(pyrimidin-2-ylmethyl)-7-(4-(trifluoromethoxy)phenyl)-3,4-dihydrobenzo[f][1,4]oxazepin-5(2H)-one (Compound I Form III) is characterized by its X-ray powder diffractogram that comprises peaks at 13.6, 20.6, and 24.1°2θ±0.2°2θ, as determined on a diffractometer using Cu-Kα radiation at a wavelength of 1.5406 Å. The diffractogram comprises additional peaks at 17.2, 19.1, and 21.7°2θ±0.2°2θ. Compound I Form III is also characterized by its full X-ray powder diffractogram as substantially shown in FIG. 39.

Figure 40:
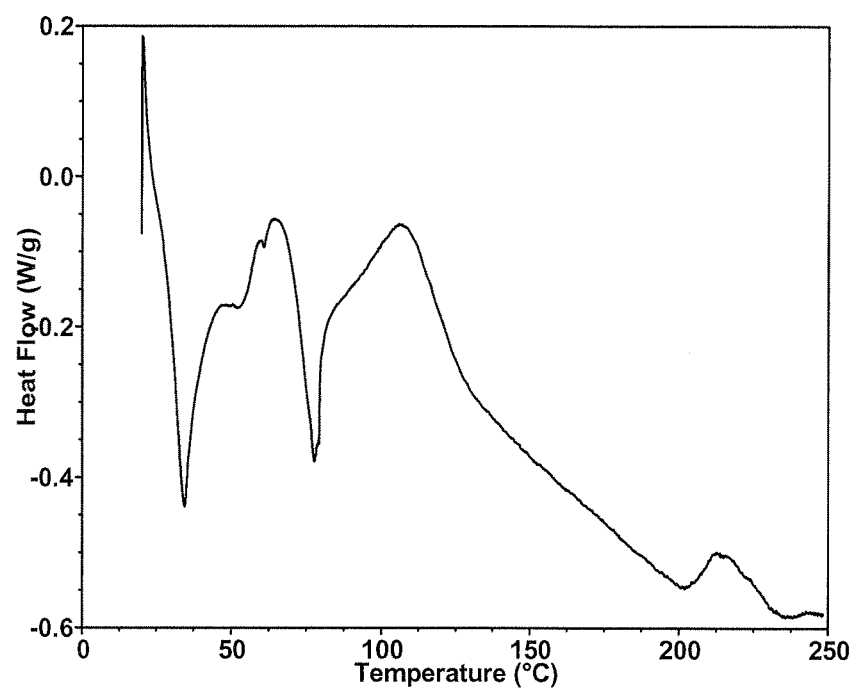
FIG. 40 shows a differential scanning calorimeter (DSC) curve of Compound I Form III.

In some embodiments, Compound I Form III is characterized by its differential scanning calorimetry (DSC) curve that comprises an endotherm at about 45° C. and an endotherm at about 78° C. Compound I Form III also is characterized by its full DSC curve as substantially as shown in FIG. 40.

In some embodiments, Compound I Form XIV is characterized by an X-ray powder diffractogram comprising the peaks at: 3.7, 16.2, 18.9, 20.0, 20.3, and 23.8°±0.2°2θ, as determined on a diffractometer using Cu-Kα radiation at a wavelength of 1.5406 Å.

In another embodiment Compound I Form XIV is characterized by a differential scanning calorimeter (DSC) thermogram with onset at about 179° C.

In another embodiment, the crystalline Compound I Form XIV is characterized a DVS analysis showing deliquescence at about 70% RH. In another embodiment, TGA analysis of crystalline Compound I Form XIV showed insignificant weight loss of about 0.26% from 25 to 179° C.

In one embodiment, crystalline Compound I Form XV is characterized by an X-ray powder diffractogram comprising the peaks at: 4.3, 19.3, 20.4, 22.1, and 22.6°±0.2°2θ, as determined on a diffractometer using Cu-Kα radiation at a wavelength of 1.5406 Å.

In another embodiment, the TGA of crystalline Compound I Form XV is characterized by insignificant weight loss of 0.2% between 25 and 150° C. In another embodiment, the DSC of crystalline Compound I Form XV is characterized by an endotherm with onset at about 110° C. and followed by an exotherm at about 122° C. and a second melting endotherm with onset at about 175° C.

In one embodiment, the Compound I Form XVI is characterized by an X-ray powder diffractogram comprising following peaks: 14.9, 16.4, 18.9, and 27.0°±0.2°2θ, as determined on a diffractometer using Cu-Kα radiation at a wavelength of 1.5406 Å. In another embodiment, integration values and peak position in the $^1$H NMR spectrum of the material are consistent with the chemical structure of Compound I Form XVI containing ethanesulfonic acid in approximate 1:1 stoichiometry. In another embodiment, the TGA thermogram of Compound I Form XVI showed insignificant weight loss of about 0.16% between 25 and 130.5° C. In another embodiment, the DSC thermogram of Compound I Form XVI showed a potential melting onset at about 130.5° C. In yet another embodiment, the DVS analysis of Compound I Form XVI showed it deliquesced at around 90% RH.

In one embodiment crystalline Compound I Form XVII is characterized by an X-ray powder diffractogram comprising peaks at: 4.3, 10.2, 18.6, 19.0, 19.3, 20.4, 21.6, 22.2 and 22.7°±0.2°2θ, as determined on a diffractometer using Cu-Kα radiation at a wavelength of 1.5406 Å. In another embodiment, the integration values and peak positions in the $^1$H NMR spectrum are consistent with the chemical structure of for Compound I Form XVII with the singlet at about 2.73 ppm signifying the presence of 1,2-ethanedisulfonic acid in a 2:1 stoichiometry. In another embodiment, the thermal data for Compound I Form XVII including DSC and TGA thermograms are consistent with an anhydrous/non-solvated form with melting onset at about 213° C. In yet another embodiment, the DVS analysis of Compound I Form XVII showed it is slightly hygroscopic with about 1% moisture uptake at 90% RH.

In one embodiment, crystalline Compound I Form XVIII is characterized by an X-ray powder diffractogram comprising the following peaks: 15.5, 19.5, and 25.7°±0.2°2θ, as determined on a diffractometer using Cu-Kα radiation at a wavelength of 1.5406 Å. In one embodiment, the thermal data including DSC and TGA thermograms are consistent with an anhydrous/non-solvated form of Compound I Form XVIII with melting onset at about 132°. In yet another embodiment, the DVS analysis of Compound I Form XVIII showed it is non-hygroscopic with about 0.075% moisture uptake at 90% RH.

One skilled in the art is aware that it is typical to observe variations in DSC curves depending on solvent (e.g., water) content, sample size, heating rate, etc.

Pharmaceutical Formulations

The Compound I forms of this disclosure may be formulated with conventional acceptable carriers and excipients, which may be selected in accord with ordinary practice. "Acceptable" is used in the sense of the carrier or excipient being compatible with other ingredients of the formulation and physiologically innocuous.

Tablets will contain excipients, glidants, fillers, binders and the like. Aqueous formulations are prepared in sterile form, and when intended for delivery by other than oral administration generally will be isotonic. Formulations may optionally contain excipients such as, for example, those set forth in the Handbook of Pharmaceutical Excipients (1986). Excipients may include ascorbic acid and other antioxidants, chelating agents such as, for example, EDTA, carbohydrates such as, for example, dextrin, hydroxyalkylcellulose, hydroxyalkylmethylcellulose, stearic acid and the like. The pH of the formulations ranges from about 3 to 11, but is ordinarily about 7 to 10. Typically, the Compound I form(s) disclosed herein will be administered in a dose from 0.01 milligrams to 2 grams. In one embodiment, the dose will be from about 10 milligrams to 450 milligrams. It is contemplated that the Compound I form(s) disclosed herein may be administered once, twice or three times a day.

While it is possible for the active ingredients to be administered alone it may be preferable to present them as pharmaceutical formulations. The formulations, both for veterinary and for human use, of the disclosure comprise at least one active ingredient, as above defined, together with one or more acceptable carriers therefore and optionally other therapeutic ingredients. The carrier(s) must be "acceptable" in the sense of being compatible with the other ingredients of the formulation and physiologically innocuous to the recipient thereof.

The formulations include those suitable for the foregoing administration routes. The formulations may conveniently be presented in unit dosage form and may be prepared by any of the methods well known in the art of pharmacy. Techniques and formulations generally may be found in Remington's Pharmaceutical Sciences (Mack Publishing Co., Easton, Pa.). Such methods include the step of bringing into association the active ingredient with the carrier which constitutes one or more accessory ingredients. Formulations may be prepared by uniformly and intimately bringing into association the active ingredient with liquid carriers or finely divided solid carriers or both, and then, if necessary, shaping the product.

Formulations of the present disclosure suitable for oral administration may be presented as discrete units such as, for example, capsules, cachets or tablets each containing a predetermined amount of the active ingredient; as a powder or granules; as a solution or a suspension in an aqueous or non-aqueous liquid; or as an oil-in-water liquid emulsion or a water-in-oil liquid emulsion. The active ingredient may also be administered as a bolus, electuary or paste.

A tablet is made by compression or molding, optionally with one or more accessory ingredients. Compressed tablets may be prepared by compressing in a suitable machine the active ingredient in a free-flowing form such as, for example, a powder or granules, optionally mixed with a binder, lubricant, inert diluent, or preservative. Molded tablets may be made by molding in a suitable machine a mixture of the powdered active ingredient moistened with an inert liquid diluent. The tablets may optionally be coated or scored and optionally are formulated so as to provide slow or controlled release of the active ingredient therefrom.

For administration to the eye or other external tissues e.g., mouth and skin, the formulations are preferably applied as a topical ointment or cream containing the active ingredient(s) in an amount of, for example, 0.075 to 20% w/w (including active ingredient(s) in a range between 0.1% and 20% in increments of 0.1% w/w such as, for example, 0.6% w/w, 0.7% w/w, etc.), preferably 0.2 to 15% w/w and most preferably 0.5 to 10% w/w. When formulated in an ointment, the active ingredients may be employed with either a paraffinic or a water-miscible ointment base. Alternatively, the active ingredients may be formulated in a cream with an oil-in-water cream base.

If desired, the aqueous phase of the cream base may include, for example, at least 30% w/w of a polyhydric alcohol, i.e. an alcohol having two or more hydroxyl groups such as, for example, propylene glycol, butane 1,3-diol, mannitol, sorbitol, glycerol and polyethylene glycol (including PEG 400) and mixtures thereof. The topical formulations may desirably include a Compound I form which enhances absorption or penetration of the active ingredient through the skin or other affected areas. Examples of such dermal penetration enhancers include dimethyl sulphoxide and related analogs.

The oily phase of the emulsions of this disclosure may be constituted from known ingredients in a known manner. While the phase may comprise merely an emulsifier (otherwise known as an emulgent), it desirably comprises a mixture of at least one emulsifier with a fat or an oil or with both a fat and an oil. Preferably, a hydrophilic emulsifier is included together with a lipophilic emulsifier which acts as a stabilizer. It is also preferred to include both an oil and a fat. Together, the emulsifier(s) with or without stabilizer(s) make up the so-called emulsifying wax, and the wax together with the oil and fat make up the so-called emulsifying ointment base which forms the oily dispersed phase of the cream formulations.

Emulgents and emulsion stabilizers suitable for use in the formulation of the disclosure include Tween® 60, Span® 80, cetostearyl alcohol, benzyl alcohol, myristyl alcohol, glyceryl mono-stearate and sodium lauryl sulfate.

The choice of suitable oils or fats for the formulation is based on achieving the desired cosmetic properties. The cream should preferably be a non-greasy, non-staining and washable product with suitable consistency to avoid leakage from tubes or other containers. Straight or branched chain, mono- or dibasic alkyl esters such as, for example, di-isoadipate, isocetyl stearate, propylene glycol diester of coconut fatty acids, isopropyl myristate, decyl oleate, isopropyl palmitate, butyl stearate, 2-ethylhexyl palmitate or a blend of branched chain esters known as Crodamol CAP may be used, the last three being preferred esters. These may be used alone or in combination depending on the properties required. Alternatively, high melting point lipids such as, for example, white soft paraffin and/or liquid paraffin or other mineral oils are used.

Pharmaceutical formulations according to the present disclosure comprise one or more Compound I forms of the disclosure together with one or more pharmaceutically acceptable carriers or excipients and optionally other therapeutic agents. Pharmaceutical formulations containing the active ingredient may be in any form suitable for the intended method of administration. When used for oral use for example, tablets, troches, lozenges, aqueous or oil suspensions, emulsions, hard or soft capsules, syrups or elixirs may be prepared. Compositions intended for oral use may be prepared according to any method known to the art for the manufacture of pharmaceutical compositions and such compositions may contain one or more agents including sweetening agents, flavoring agents, coloring agents and preserving agents, in order to provide a palatable preparation. Tablets containing the active ingredient in admixture with non-toxic pharmaceutically acceptable excipient which are suitable for manufacture of tablets are acceptable. These excipients may be, for example, inert diluents, such as, for example, calcium or sodium carbonate, lactose, lactose monohydrate, croscarmellose sodium, povidone, calcium or sodium phosphate; granulating and disintegrating agents, such as, for example, maize starch, or alginic acid; binding agents, such as, for example, cellulose, microcrystalline cellulose, starch, gelatin or acacia; and lubricating agents, such as, for example, magnesium stearate, stearic acid or talc. Tablets may be uncoated or may be coated by known techniques including microencapsulation to delay disintegration and adsorption in the gastrointestinal tract and thereby provide a sustained action over a longer period. For example, a time delay material such as, for example, glyceryl monostearate or glyceryl distearate alone or with a wax may be employed.

Formulations for oral use may be also presented as hard gelatin capsules where the active ingredient is mixed with an inert solid diluent, for example calcium phosphate or kaolin, or as soft gelatin capsules wherein the active ingredient is mixed with water or an oil medium, such as, for example, peanut oil, liquid paraffin or olive oil.

Aqueous suspensions of the disclosure contain the active materials in admixture with excipients suitable for the manufacture of aqueous suspensions. Such excipients include a suspending agent, such as, for example, sodium carboxymethylcellulose, methylcellulose, hydroxypropyl methylcellulose, sodium alginate, polyvinylpyrrolidone, gum tragacanth and gum acacia, and dispersing or wetting agents such as, for example, a naturally occurring phosphatide (e.g., lecithin), a condensation product of an alkylene oxide with a fatty acid (e.g., polyoxyethylene stearate), a condensation product of ethylene oxide with a long chain aliphatic alcohol (e.g., heptadecaethyleneoxycetanol), a condensation product of ethylene oxide with a partial ester derived from a fatty acid and a hexitol anhydride (e.g., polyoxyethylene sorbitan monooleate). The aqueous suspension may also contain one or more preservatives such as, for example, ethyl or n-propyl p-hydroxy-benzoate, one or more coloring agents, one or more flavoring agents and one or more sweetening agents, such as, for example, sucrose or saccharin.

Oil suspensions may be formulated by suspending the active ingredient in a vegetable oil, such as, for example, arachis oil, olive oil, sesame oil or coconut oil, or in a mineral oil such as, for example, liquid paraffin. The oral suspensions may contain a thickening agent, such as, for example, beeswax, hard paraffin or cetyl alcohol. Sweetening agents, such as, for example, those set forth above, and flavoring agents may be added to provide a palatable oral preparation. These compositions may be preserved by the addition of an antioxidant such as, for example, ascorbic acid.

Granules of the disclosure suitable for preparation of an aqueous suspension by the addition of water provide the active ingredient in admixture with a dispersing or wetting agent, a suspending agent, and one or more preservatives. Suitable dispersing or wetting agents and suspending agents are exemplified by those disclosed above. Additional excipients, for example sweetening, flavoring and coloring agents, may also be present.

The pharmaceutical compositions of the disclosure may also be in the form of oil-in-water emulsions. The oily phase may be a vegetable oil, such as, for example, olive oil or arachis oil, a mineral oil, such as, for example, liquid paraffin, or a mixture of these. Suitable emulsifying agents include naturally-occurring gums, such as, for example, gum acacia and gum tragacanth, naturally occurring phosphatides, such as, for example, soybean lecithin, esters or partial esters derived from fatty acids and hexitol anhydrides, such as, for example, sorbitan monooleate, and condensation products of these partial esters with ethylene oxide, such as, for example, polyoxyethylene sorbitan monooleate. The emulsion may also contain sweetening and flavoring agents. Syrups and elixirs may be formulated with sweetening agents, such as, for example, glycerol, sorbitol or sucrose. Such formulations may also contain a demulcent, a preservative, a flavoring or a coloring agent.

The pharmaceutical compositions of the disclosure may be in the form of a sterile injectable preparation, such as, for example, a sterile injectable aqueous or oleaginous suspension. This suspension may be formulated according to the known art using those suitable dispersing or wetting agents and suspending agents which have been mentioned above. The sterile injectable preparation may also be a sterile injectable solution or suspension in a non-toxic parenterally acceptable diluent or solvent, such as, for example, a solution in 1,3-butane-diol or prepared as a lyophilized powder. Among the acceptable vehicles and solvents that may be employed are water, Ringer's solution and isotonic sodium chloride solution. In addition, sterile fixed oils may conventionally be employed as a solvent or suspending medium. For this purpose any bland fixed oil may be employed including synthetic mono- or diglycerides. In addition, fatty acids such as, for example, oleic acid may likewise be used in the preparation of injectables.

The amount of active ingredient that may be combined with the carrier material to produce a single dosage form will vary depending upon the host treated and the particular mode of administration. For example, a time-release formulation intended for oral administration to humans may contain approximately 1 to 1000 mg of active material compounded with an appropriate and convenient amount of carrier material which may vary from about 5 to 95% of the total compositions (weight:weight). The pharmaceutical composition may be prepared to provide easily measurable amounts for administration. For example, an aqueous solution intended for intravenous infusion may contain from about 3 to 500 μg of the active ingredient per milliliter of solution in order that infusion of a suitable volume at a rate of about 30 mL/hr may occur.

Formulations suitable for administration to the eye include eye drops wherein the active ingredient is dissolved or suspended in a suitable carrier, especially an aqueous solvent for the active ingredient. The active ingredient is preferably present in such formulations in a concentration of 0.5 to 20%, advantageously 0.5 to 10%, particularly about 1.5% w/w.

Formulations suitable for topical administration in the mouth include lozenges comprising the active ingredient in a flavored basis, usually sucrose and acacia or tragacanth; pastilles comprising the active ingredient in an inert basis such as, for example, gelatin and glycerin, or sucrose and acacia; and mouthwashes comprising the active ingredient in a suitable liquid carrier.

Formulations for rectal administration may be presented as a suppository with a suitable base comprising for example cocoa butter or a salicylate.

Formulations suitable for intrapulmonary or nasal administration have a particle size for example in the range of 0.1 to 500 microns (including particle sizes in a range between 0.1 and 500 microns in increments microns such as, for example, 0.5, 1, 30 microns, 35 microns, etc.), which is administered by rapid inhalation through the nasal passage or by inhalation through the mouth so as to reach the alveolar sacs. Suitable formulations include aqueous or oily solutions of the active ingredient. Formulations suitable for aerosol or dry powder administration may be prepared according to conventional methods and may be delivered with other therapeutic agents such as, for example, compounds heretofore used in the treatment or prophylaxis of conditions associated with HCV activity.

Formulations suitable for vaginal administration may be presented as pessaries, tampons, creams, gels, pastes, foams or spray formulations containing in addition to the active ingredient such carriers as are known in the art to be appropriate.

Formulations suitable for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents.

The formulations are presented in unit-dose or multi-dose containers, for example sealed ampoules and vials, and may be stored in a freeze-dried (lyophilized) condition requiring only the addition of the sterile liquid carrier, for example water for injection, immediately prior to use. Extemporaneous injection solutions and suspensions are prepared from sterile powders, granules and tablets of the kind previously described. Preferred unit dosage formulations are those containing a daily dose or unit daily sub-dose, as herein above recited, or an appropriate fraction thereof, of the active ingredient.

It should be understood that in addition to the ingredients particularly mentioned above the formulations of this disclosure may include other agents conventional in the art having regard to the type of formulation in question, for example those suitable for oral administration may include flavoring agents.

The disclosure further provides veterinary compositions comprising at least one active ingredient as above defined together with a veterinary carrier therefore.

Veterinary carriers are materials useful for the purpose of administering the composition and may be solid, liquid or gaseous materials which are otherwise inert or acceptable in the veterinary art and are compatible with the active ingredient. These veterinary compositions may be administered orally, parenterally or by any other desired route.

Compound I forms of the disclosure may also be formulated to provide controlled release of the active ingredient to allow less frequent dosing or to improve the pharmacokinetic or toxicity profile of the active ingredient. Accordingly, the disclosure also provides compositions comprising one or more Compound I forms of the disclosure formulated for sustained or controlled release.

Effective dose of active ingredient depends at least on the nature of the condition being treated, toxicity, whether the compound is being used prophylactically (lower doses), the method of delivery, and the pharmaceutical formulation, and will be determined by the clinician using conventional dose escalation studies.

Methods of Use

The solid forms of Compound I described herein are administered to a subject suffering from a neurological and/or cardiac condition associated with abnormal INaL enhancement. Administration routes include, for example, those described in any patents and patent applications incorporated by reference, such as rectal, buccal, intranasal and transdermal routes, by intra-arterial injection, intravenously, intraperitoneally, parenterally, intramuscularly, subcutaneously, orally, topically, as an inhalant, or via an impregnated or coated device such as a stent, for example, or an artery-inserted cylindrical polymer.

Oral administration may be carried out by delivering any of the Compound I forms disclosed herein by capsule or enteric coated tablets, or the like.

The Compound I forms also may be administered by transdermal delivery devices ("patches"). Such transdermal patches may be used to provide continuous or discontinuous infusion of the compounds of the present disclosure in controlled amounts. The construction and use of transdermal patches for the delivery of pharmaceutical agents is well known in the art. See, e.g., U.S. Pat. Nos. 5,023,252, 4,992,445 and 5,001,139. Such patches may be constructed for continuous, pulsatile, or on demand delivery of pharmaceutical agents.

The compounds are preferably formulated in a unit dosage form. The term "unit dosage forms" refers to physically discrete units suitable as unitary dosages for human subjects and other mammals, each unit containing a predetermined quantity of active material calculated to produce the desired therapeutic effect. The compounds are generally administered in a pharmaceutically effective amount.

For oral administration, each dosage unit typically contains from 0.1 mg 1 mg to 2 g of a compound described herein. It will be understood, however, that the amount of the compound actually administered usually will be determined by a physician, in the light of the relevant circumstances, including the condition to be treated, the chosen route of administration, the actual compound administered and its relative activity, the age, weight, and response of the individual patient, the severity of the patient's symptoms, and the like.

EXAMPLES

Example 1

Compound I Form I

Figure 33:
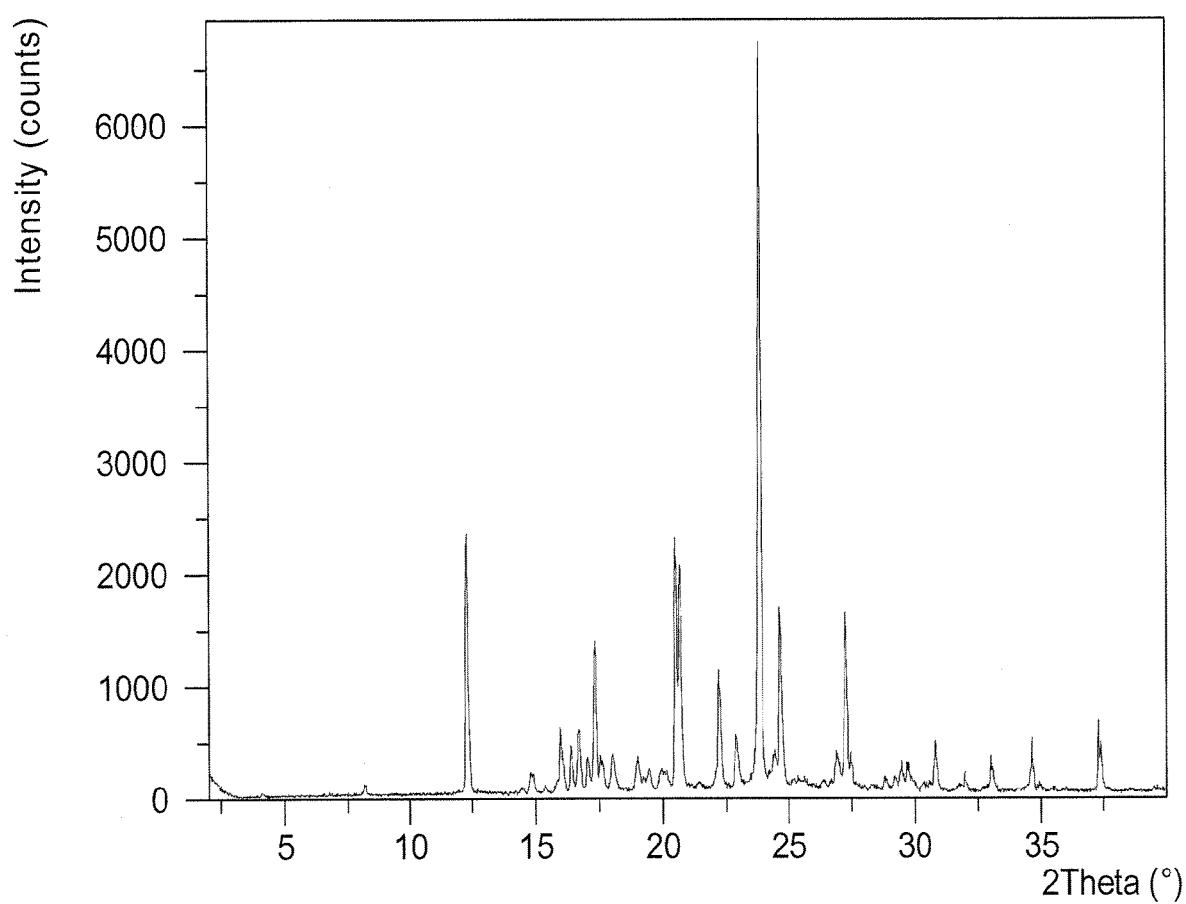
FIG. 33 shows an X-ray powder diffraction (XRPD) of Compound I Form I.
Figure 35:
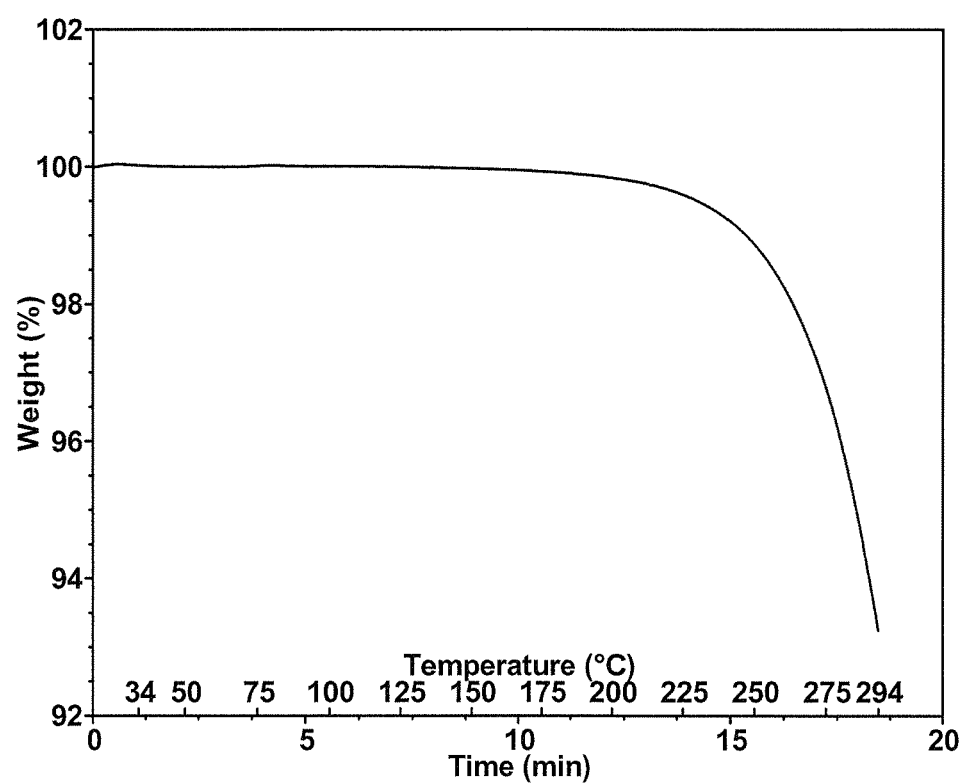
FIG. 35 shows a thermogravimetric analysis (TGA) of Compound I Form I.
Figure 42:
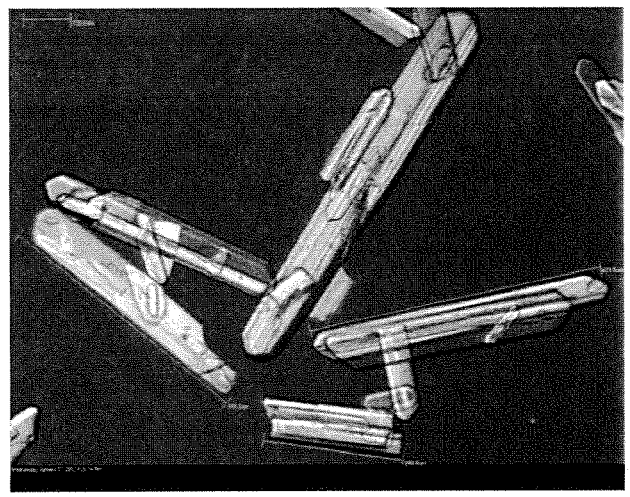
FIG. 42 shows microscopy pictures (200× magnification) of Compound I Form I: a) before and b) after grinding.
Figure 42:
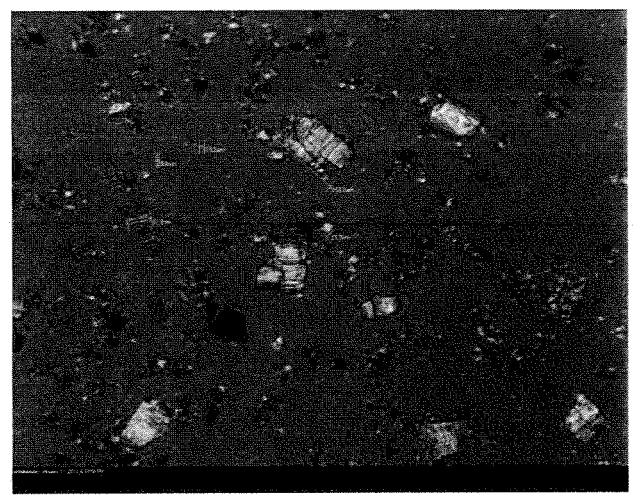

Compound I free base prepared by the procedure disclosed in PCT International publication WO 2013/006485 was isolated as a crystalline solid from MTBE/hexanes. Crystallization of Compound I under various conditions has also resulted in the isolation of Form I. A typical pXRD pattern of Form I is shown in FIG. 33. Form I is highly crystalline and may exist as large rod-like crystals, affording strong preferred orientation by pXRD. However, small rod shapes and undefined shapes have been observed. Light grinding with mortar and pestle indicates that the crystals are brittle and significantly reduces preferred orientation by pXRD and Polarized light Microscopy (PLM) images (FIG. 42a versus FIG. 42b). Differential scanning calorimetry (DSC) of Form I showed a sharp endotherm onset at about 78.6° C., with no thermal events prior to or after the endotherm (FIG. 34). Thermal gravimetric analysis (TGA) data showed 0.4% weight loss below 150° C., indicating that Form I is an anhydrous crystalline form of Compound I (FIG. 35). A 10° C./min heating rate was used for the DSC and TGA experiments.

Example 2

Compound I Form Screen

In order to determine whether other polymorphs of Compound I exist, a stable form screen was conducted. Compound I is highly soluble in many organic solvents. As a result, slurries were typically produced in non-polar solvents. Table 1). Slurries were also generated in solvent combinations with n-heptane (Table 2) and cyclohexane (Table 3). In cases where a slurry was formed, Form I was isolated after agitation for 1 day and 3 weeks.

TABLE 1

Stable Form Screen in Single Solvents

| Solvent | Solubility (mg/g) (3 weeks)* | Form (1 day) | Appearance |
|---|---|---|---|
| MTBE | >240 | NA | homogenous |
| Toluene | >500 | NA | homogenous |
| IPA | >300 | NA | homogenous |
| MeCN | >350 | NA | homogenous |

TABLE 1-continued

Stable Form Screen in Single Solvents

| Solvent | Solubility (mg/g) (3 weeks)* | Form (1 day) | Appearance |
|---|---|---|---|
| n-Heptane | 0.9 | I | slurry |
| Cyclohexane | 2.4 | I | slurry |
| IPE | 21.5 | I | slurry |
| Water | 0 | I | slurry |

*Solubility measured by HPLC based on external standard

TABLE 2

Stable Form Screen in Binary Solvents with Heptane

| Solvent (Ratio v/v) | Solubility (mg/g)* (3 weeks) | Form (1 day) | Appearance |
|---|---|---|---|
| MTBE/n-heptane (1:2) | 5.4 | I | slurry |
| Toluene/n-heptane (1:3) | 7.1 | I | slurry |
| IPA/n-heptane (1:4) | 20.0 | I | slurry |
| 2-MeTHF/n-heptane (1:5) | 6.7 | I | slurry |
| iPrOAc/n-heptane (1:3) | 18.9 | I | slurry |
| DCM/n-heptane (1:3) | NA | NA | Oiled out (2 d) |
| t-amyl alcohol/n-heptane (1:3) | 17.5 | I | slurry |

*Solubility measured by HPLC based on external standard.

TABLE 3

Stable Form Screen in Binary Solvents with Cyclohexane

| Solvent (Ratio v/v) | Solubility (mg/g) (1 day) | Form (1 day) | Appearance |
|---|---|---|---|
| EtOAc/cyclohexane (1:3) | 86 | I | slurry |
| MEK/cyclohexane (1:6) | NA | NA | Cloudy |
| Acetone/cyclohexane (1:6) | NA | NA | Cloudy |

Example 3

Compound I Form II

Figure 45:
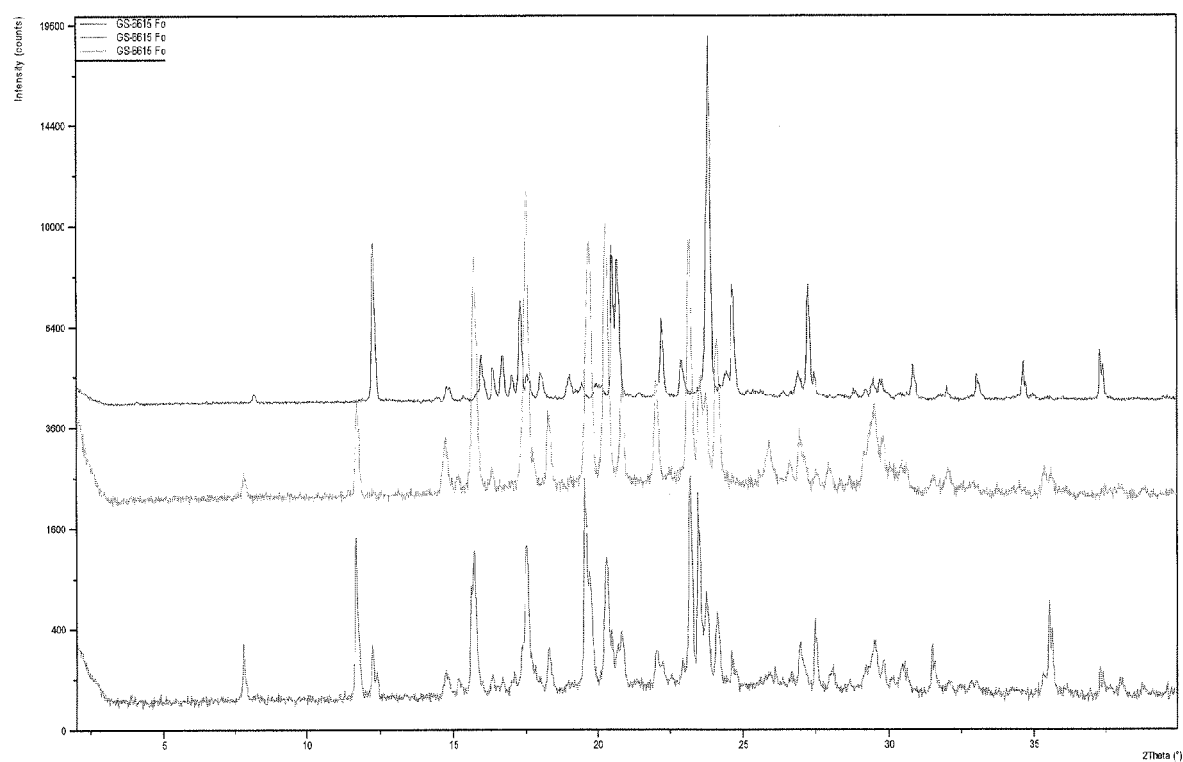
FIG. 45 shows an X-ray powder diffraction (XRPD) of Compound I Form I (top trace), Form II (center trace) and a mixture of Forms I and II (bottom trace).

Compound I Form II was discovered during laboratory crystallization of crude Compound I. The initial solids that were isolated were determined to be actually a mixture of Forms I and II (FIG. 45). In reviewing the crystallization conditions that afforded a mixture of Forms I and II, it was noted that the jacket temperature was set slightly higher than normal (35° C. versus 30° C.) during the crystallization in iPrOAc/n-heptane. It is contemplated that Forms I and II are enantiotropic forms.

Table 6 describes the set of experiments which concluded that Form I and II are enantiotropic forms and determined the transition temperature. Slurries of Form I with and without Form II seeds were stirred at 35° C. and 38° C. and samples were removed periodically for pXRD analysis. For slurries of Form I aged at 35° C., Form I dominated regardless of whether Form II seeds were present (albeit when Form II seeds were present, the full conversion to Form I took about 5 days) (Table 4). In contrast, slurries of Form I at 38° C. in the presence of Form II seeds rapidly turned over to Form II within 1 day and remained Form II even after the slurry was cooled to 20° C. for isolation. When no Form II seeds were present, Form I slurries remained unchanged even when aged at 38° C. From these results, the following conclusions may be made:

- Form I is the more stable form at below 35° C. while Form II is the more stable form at or above 38° C.
- The transition temperature between Forms I and II is approximately between 35 to 38° C.
- Form I to II conversion is accelerated by seeding, although the rate of conversion may be dependent on the solvent composition.
- Form I to II conversion in iPrOAc/n-heptane at 38° C. is rapid in the presence of Form II seeds.

TABLE 4

Determination of Transition Temperature between Forms I and II

| Temperature | Addition of Form II seed (10%) | Form I or II by XRPD (time) |
|---|---|---|
| 35° C. | No | I (3 h) |
| | | I (20 h) |
| | | I (2 days) |
| | | I (5 days) |
| 35° C. | Yes | I/II (3 h) |
| | | I/II (20 h) |
| | | I/II (2 days) |
| | | I (5 days) |
| 38° C. | No | I (2 h) |
| | | I (17 h) |
| | | I (2 days) |
| | | I (4 days) |
| | | I (6 days) |
| 38° C. | Yes | I/II (2 h) |
| | | II (17 h) |
| | | II (2 days) |
| | | II (4 days) |
| | | II (6 days) |

Figure 36:
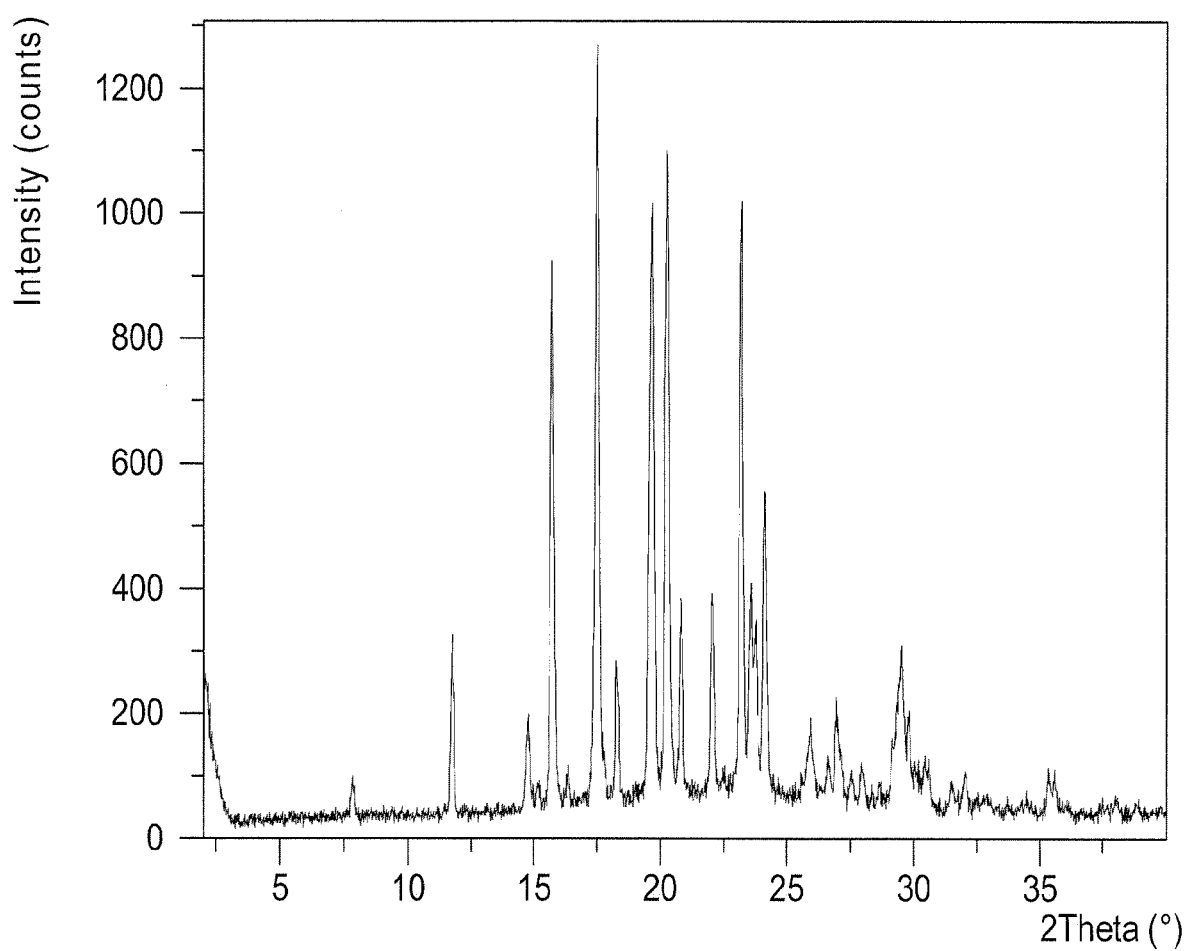
FIG. 36 shows an X-ray powder diffraction (XRPD) of Compound I Form II.
Figure 38:
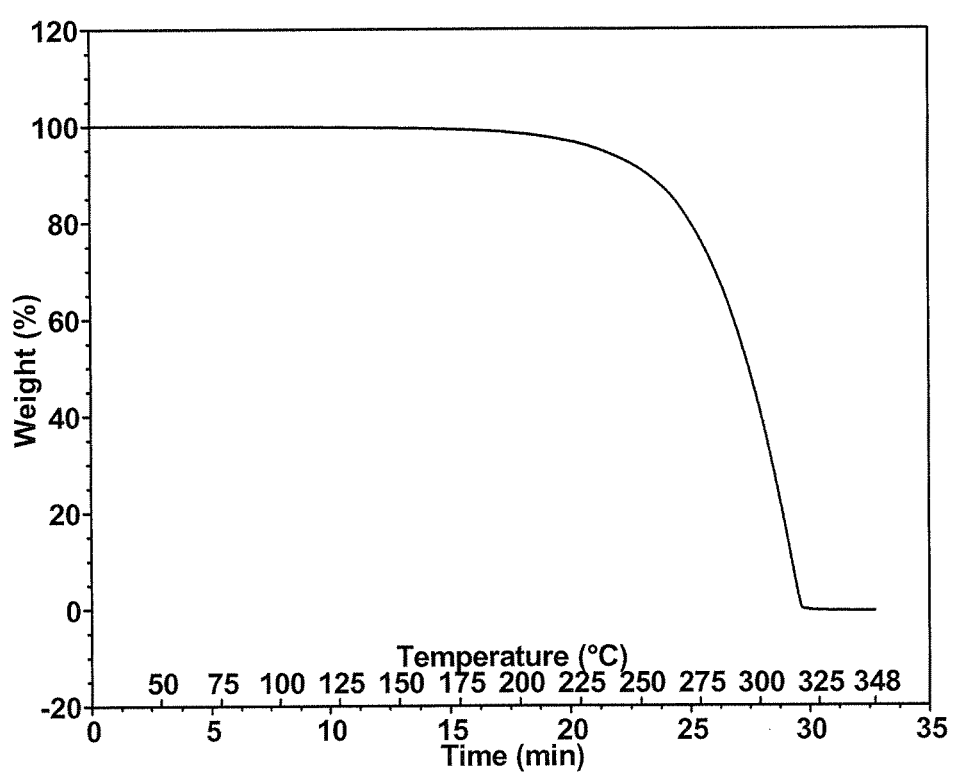
FIG. 38 shows a thermogravimetric analysis (TGA) of Compound I Form II.

The pXRD, DSC, and TGA profiles for Form II are presented in FIG. 36, FIG. 37 and FIG. 38, respectively. Compound I Form II can be made by a polymorph conversion of Form I at temperatures above about 38° C. A typical procedure is as follows.

Compound I Form I (0.5 g) is charged into a mixture of isopropyl acetate/n-heptane (5 ml, 1:3 v/v). The slurry is heated to about 38 to 40° C. and Form II seed (50 mg) is added. The slurry is aged for about 12 hours. The slurry is filtered, rinsed with n-heptane, and dried under vacuum to afford Form II as a crystalline solid.

Alternatively, a mixture of Compound I (5 g) in methyl tert-butyl ether (MTBE, 30 mL) was heated to about 25° C. and stirred until all the solids were dissolved (about 10 min). The solution was cooled to about 20° C. and n-heptane (5 mL) was added over about 10 minutes. Upon complete addition of n-heptane, a slurry mixture was formed. The slurry was stirred at about 20° C. for one hour and additional n-heptane (55 mL) was added over two hours. The slurry was cooled to about 0° C. over two hours, filtered, and dried under vacuum at about 20 to about 25° C. Analysis of the isolated Compound I by PXRD showed Form II.

Figure 43:
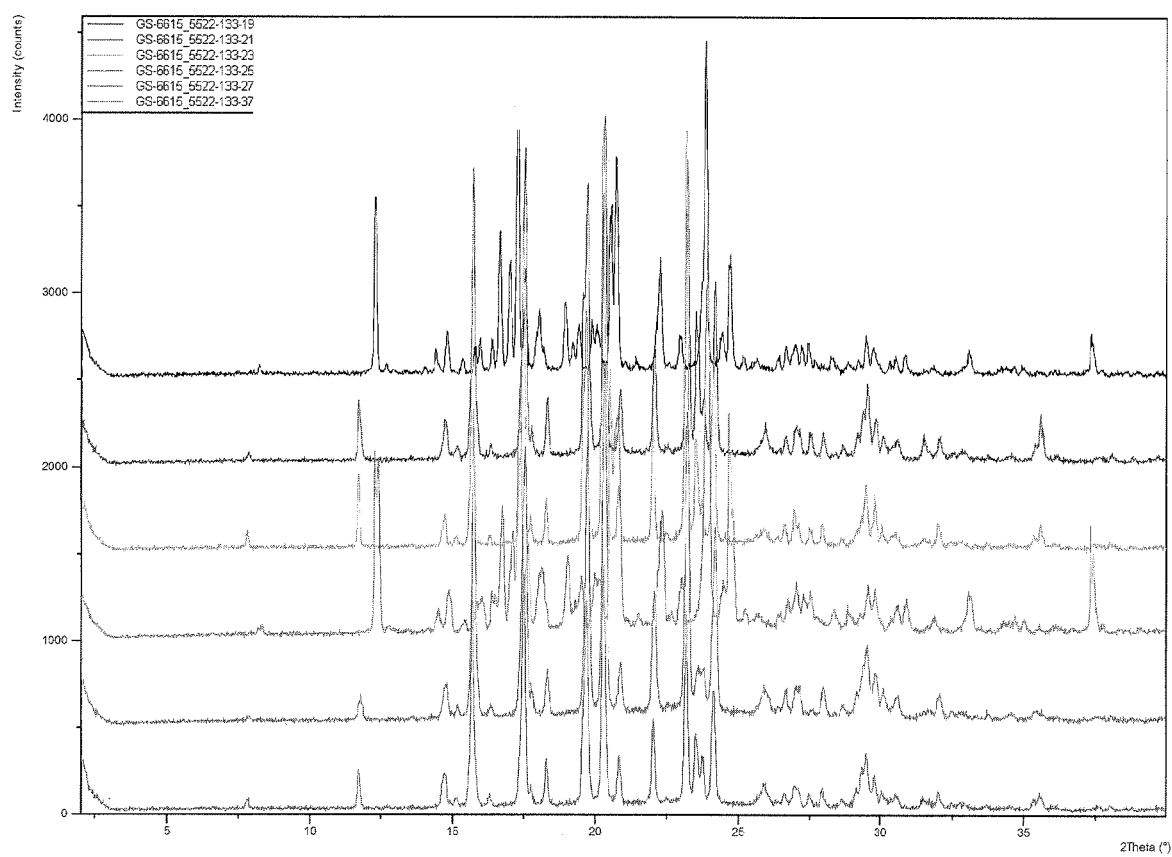
FIG. 43 shows an X-ray powder diffraction (XRPD) of Compound I extended stable Form screen (4 days).

An additional form screen in other solvent combinations was performed and the data is presented in Table 5. These experiments were performed at about 21° C. starting from Form II. After about 3 to 6 days in suspension two experiments produced full conversion from Form II to Form I; one became biphasic; and the rest remained Form II (FIG. 43). Three of the filtrates obtained from isolating the solid phase from samples became biphasic before the solubility could be measured by TGA.

Figure 44:
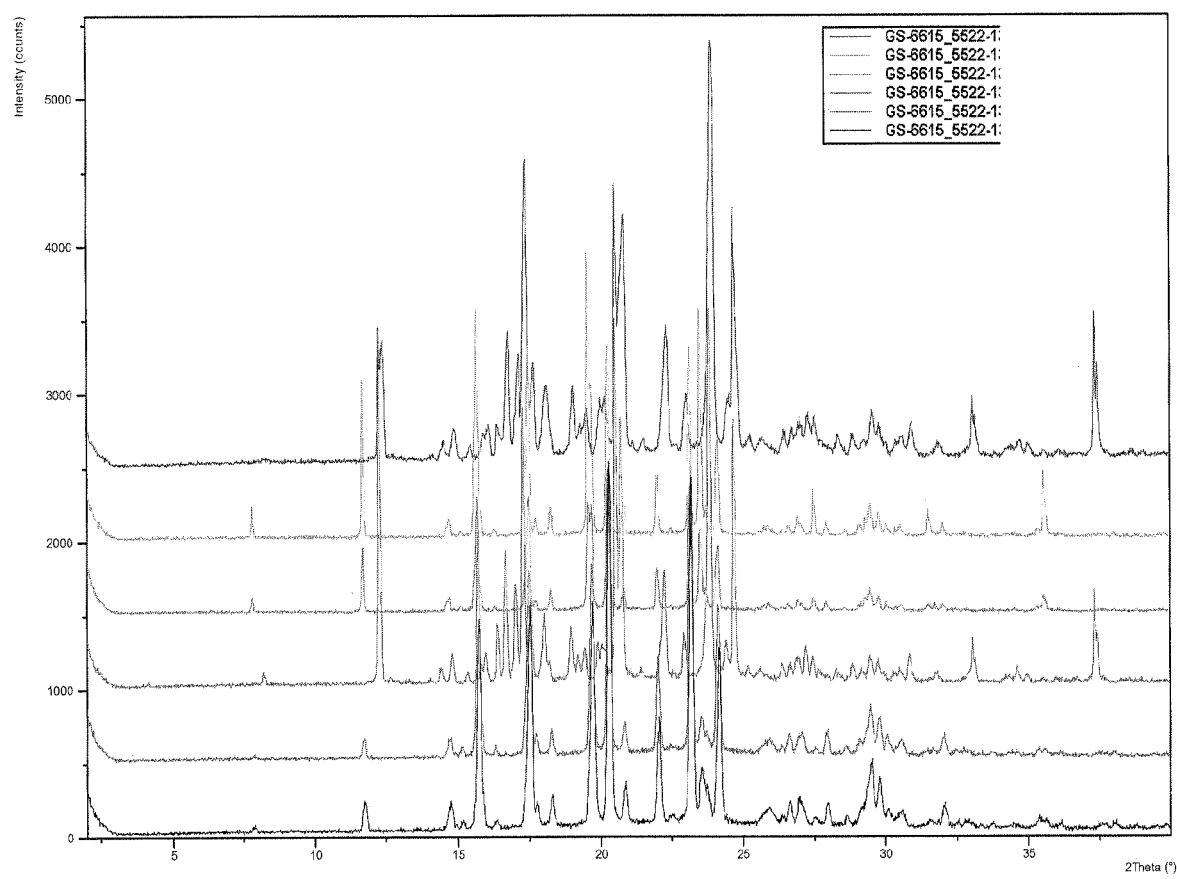
FIG. 44 shows an X-ray powder diffraction (XRPD) of Compound I extended stable Form screen (11 days).

After about 8 to 11 days in suspension the distribution of forms remained unchanged (FIG. 44). All of the filtrates except one became biphasic before solubility could be measured by TGA.

TABLE 5

Compound I Extended Stable Form Screen (4 mL vial, 2 mL solvent each)

| Form II (mg) | Solvent (v/v) | 4-6 Days XRPD | 4-6 Days Solubility (mg/mL) | 8-11 Day XRPD | 8-11 Day Solubility (mg/mL) | Comment |
|---|---|---|---|---|---|---|
| 291 | n-heptane sat'd w/ MeOH | NA | NA | NA | NA | biphasic; yellow oil at bottom |
| 293 | n-heptane sat'd w/ ACN | Form I | NA | Form I | NA | sticky solids; filtrate became biphasic |
| 323 | Ethanol/n-heptane (1/4) | Form II | 32 | Form II | NA | suspension |
| 290 | EtOAc/n-heptane (1/4) | Form II | NA | Form II | NA | suspension; filtrate became biphasic |
| 336 | MEK/n-heptane (1/4) | Form I | NA | Form I | NA | suspension; filtrate became biphasic |
| 330 | MIBK/n-heptane (1/4) | Form II | 26 | Form II | 35 | sticky solids then a suspension |
| 227 | THF/n-heptane (1/4) | Form II | 29 | Form II | NA | suspension |

* NA = Data not available.

Example 4

Compound I Hydrate Screen (Form III)

A hydrate screen starting from Form I was also conducted to evaluate whether hydrates of Compound I exist. The hydrate screen was conducted in ethanol/water (Table 6) and isopropanol/water (Table 7) mixtures, and in both cases, a new polymorph of Compound I was discovered (denoted as Form III).

TABLE 6

Ethanol/Water Hydrate Screen (5 days)

| Volume % EtOH | Water Activity | Form | Solubility (mg/g) | Appearance |
|---|---|---|---|---|
| 10% | >0.9 | I | 0 | Slurry |
| 20% | 0.8-0.9 | III | 0.05 | Slurry |
| 30% | 0.8-0.9 | I | 0.6 | Slurry |
| 40% | 0.8-0.9 | NA | NA | Oil |
| 50% | 0.8 | NA | NA | cloudy |

* NA = Data not available.

TABLE 7

Isopropanol/Water Hydrate Screen (5 days)

| Volume % IPA | Water Activity | Form | Solubility (mg/g) | Appearance |
|---|---|---|---|---|
| 10% | >0.9 | III | 0 | Slurry |
| 20% | >0.9 | I | 0 | Slurry |
| 25% | >0.9 | III | 0.5 | Slurry |
| 30% | >0.9 | NA | NA | oil |
| 40% | 0.8-0.9 | NA | NA | homogenous |

* NA = Data not available.

Figure 39:
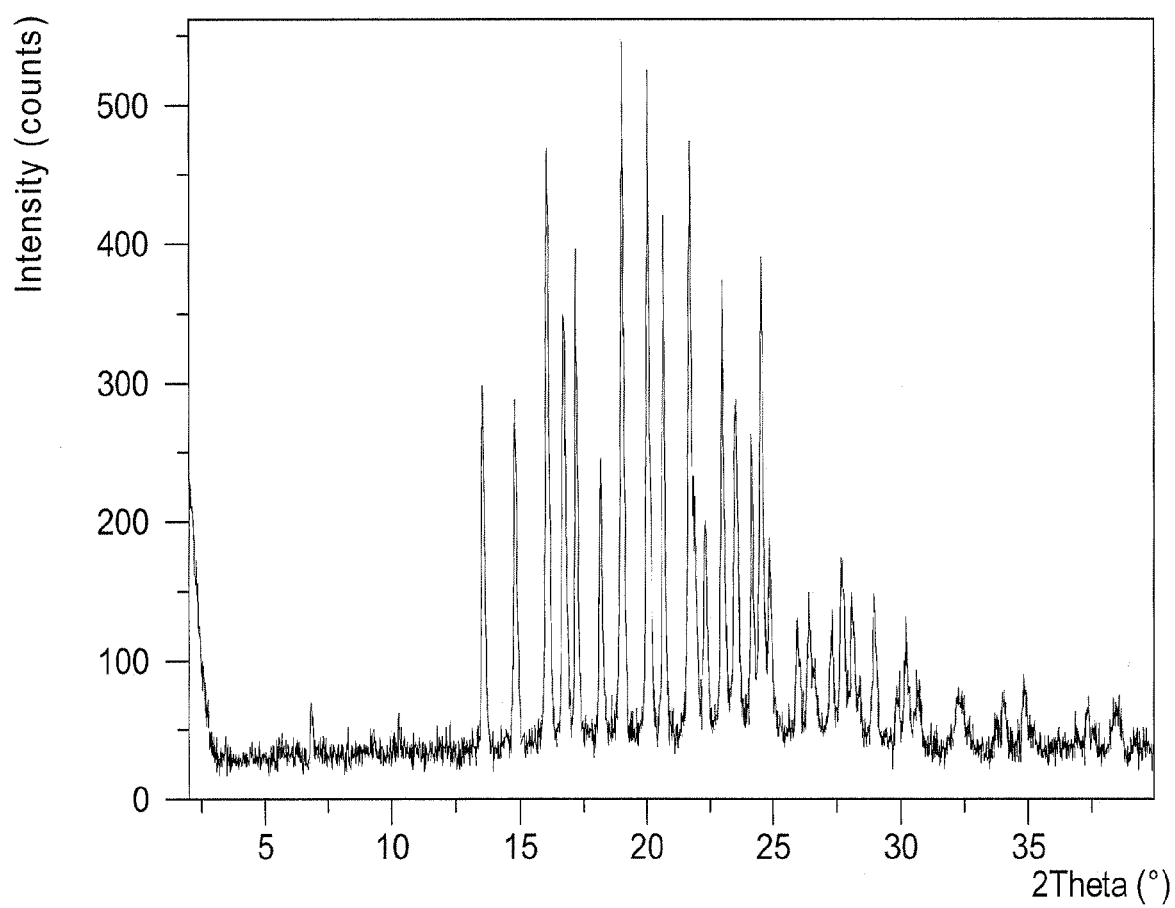
FIG. 39 shows an X-ray powder diffraction (XRPD) of Compound I Form III.
Figure 41:
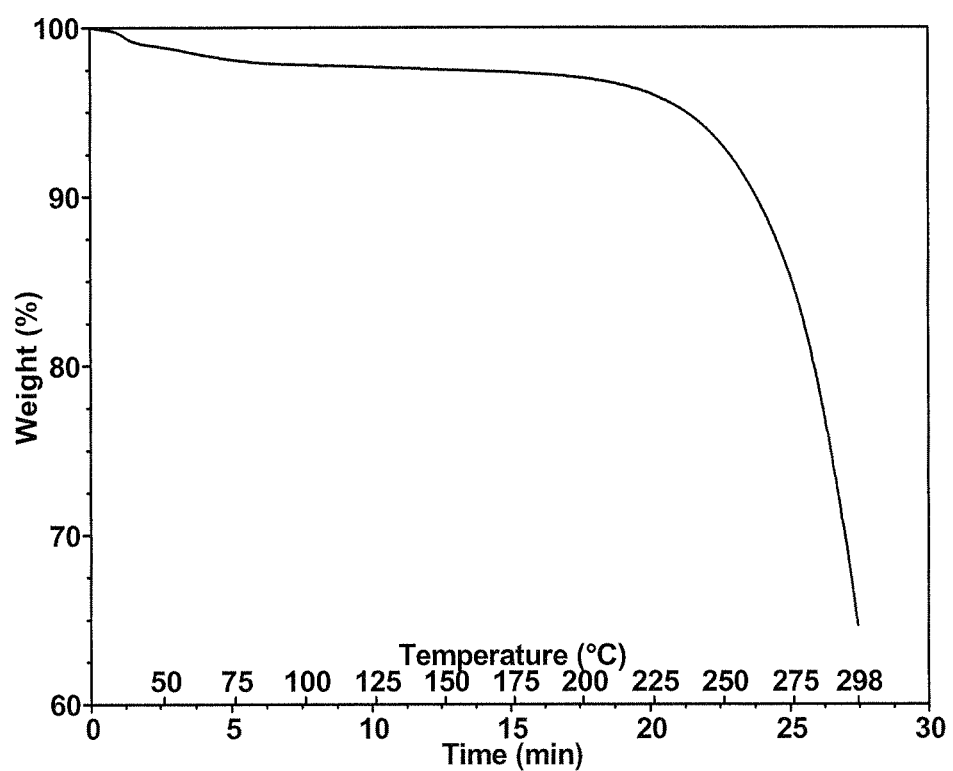
FIG. 41 shows a thermogravimetric analysis (TGA) of Compound I Form III.

The pXRD, DSC, and TGA profiles for Form III are presented in FIG. 39, FIG. 40 and FIG. 41, respectively. Based on this data and Karl Fischer analysis, Form III was determined to be a hydrate of Compound I. Form III is thought to be a variable hydrate. Depending on the method of drying, variable water content (as measured by Karl Fischer titration) has been observed. Variable weight loss (corresponding to loss of water) is also observed by TGA. A 10° C./min heating rate was implemented for the DSC and TGA experiments.

From the initial hydrate screens presented in Table 6 and Table 7 no apparent trends were observed. The stable hydrate screens were repeated starting from Form I and the data is presented in Table 10 and Table 11. In this case, all slurries of Form I in EtOH/water or IPA/water mixtures remained unchanged after 2 weeks (Table 8 and Table 9). Since Form III has been observed previously under the same conditions, it was suspected that the lack of form conversion is mainly due to slow kinetics. A follow-up competition slurry experiment showed that in the presence of Form III seed (50 wt %), Form I to III conversion occurred (after 1 day). In the range of water activities where a slurry exists, Form I to III conversion was observed in all cases. This information supports that Form III is the most stable polymorph of Compound I at water activities above 0.8. Attempts to determine the relative stability between Forms I and III at lower water activities were unsuccessful since Form I either was too soluble or oiled out at water activities of 0.8 or below.

TABLE 8

Stable Hydrate Screen in EtOH/water

| Entry | Volume % EtOH | Water Activity | Form (2 weeks) | Form I Solubility mg/g (2 weeks) |
|---|---|---|---|---|
| A1 | 10% | >0.9 | I | 0.09 |
| B1 | 20% | 0.8-0.9 | I | 0.10 |
| C1 | 30% | 0.8-0.9 | I | 0.49 |
| D1 | 35% | 0.8-0.9 | I | 1.3 |

TABLE 8-continued

Stable Hydrate Screen in EtOH/water

| Entry | Volume % EtOH | Water Activity | Mixture of Form I & III (50:50 w/w) (1 day) | Form III Solubility mg/g (1 day) |
|---|---|---|---|---|
| A2 | 10% | >0.9 | III | 0.06 |
| B2 | 20% | 0.8-0.9 | III | 0.10 |
| C2 | 30% | 0.8-0.9 | III | 0.49 |
| D2 | 35% | 0.8-0.9 | III | 1.8 |
| E2 | 52% | 0.8 | —[1] | —[1] |
| F2 | 52% | 0.8 | —[2] | —[2] |

[1]Attempts to supersaturate Form I in this solvent mixture resulted in oiling out of Form I.
[2]Form III was used in this experiment, which initially formed a slurry of Form III but eventually oiled out.

TABLE 9

Stable Hydrate Screen in IPA/water

| Entry | Volume % IPA | Water Activity | Form (2 weeks) | Form I Solubility mg/g (2 weeks) |
|---|---|---|---|---|
| A1 | 10% | >0.9 | I | 0.10 |
| B1 | 20% | >0.9 | I | 0.18 |
| C1 | 25% | >0.9 | I | 0.65 |
| D1 | 30% | >0.9 | I | 4.7 |

| Entry | Volume % IPA | Water Activity | Mixture of Form I & III (50:50 w/w) (1 day) | Form III Solubility mg/g (1 day) |
|---|---|---|---|---|
| A2 | 10% | >0.9 | III | 0.06 |
| B2 | 20% | >0.9 | III | 0.19 |
| C2 | 25% | >0.9 | III | 0.78 |
| D2 | 30% | >0.9 | III | 3.2 |
| E2 | 84% | 0.8 | —[1] | —[1] |
| F2 | 84% | 0.8 | —[2] | —[2] |

[1]Attempts to supersaturate this solvent mixture with Form I was unsuccessful (Form I dissolved, no slurry could be formed even at very high concentrations).
[2]Attempts to supersaturate Form III in this solvent mixture also led to dissolution of Form III.

Since the hydrate screens from aqueous mixtures of ethanol and isopropyl alcohol were performed in a fairly narrow range of water activity ($A_w \geq 0.8$), it was desirable to determine the outcome over a wider range of water activities. An attempt was made to explore this using a system of methanol and water (Table 10). Form I was used as the starting material. At $A_w$ below 0.6, the solubility was extraordinarily high and only solutions were present. At and above this $A_w$ only Form I was found. Notably, at $A_w$ 0.6 Form I was present after 3 days, but was replaced with an oil by 14 days.

TABLE 10

Stable Hydrate Screen in methanol/water

| Entry | Aw | 3 days TGA (mg/mL) | 3 days XRPD | 14 days TGA (mg/mL) | 14 days XRPD | comment |
|---|---|---|---|---|---|---|
| 1 | 0.1 | NA | NA | NA | NA | solution (entire time) |
| 2 | 0.2 | NA | NA | NA | NA | solution (entire time) |
| 3 | 0.3 | NA | NA | NA | NA | solution (entire time) |
| 4 | 0.4 | NA | NA | NA | NA | solution (entire time) |
| 5 | 0.5 | NA | NA | NA | NA | biphasic; no solids (entire time) |
| 6 | 0.6 | 14 | Form I | NA | NA | suspension (3 days); biphasic (14 days) |
| 7 | 0.7 | 4.5 | Form I | 2 | Form I | suspension (entire time) |
| 8 | 0.8 | 1.4 | Form I | 1 | Form I | suspension (entire time) |
| 9 | 0.9 | 0.5 | Form I | <1 | Form I | suspension (entire time) |

* NA = data not available.

Other solvents were briefly examined but resulted in oily residues or a cloudy solution and thus, was not further explored (Table 11).

TABLE 11

Hydrate Screen with Other Water Miscible Solvents

| Entry | Solvent (Ratio v/v) | Appearance |
|---|---|---|
| 1 | THF/water (1:3) | Oiled out |
| 2 | MeCN/water (1:3) | Oiled out |
| 3 | Acetone/water (1:3) | Slurry (t = 0) Oiled out (t = 1 d) |
| 4 | Acetone/water (1:2) | Cloudy (t = 0) Oiled out (t = 1 d) |

Example 5

Compound I Salt/Co-Crystal Screen

Compound I salt/co-crystal screen was performed in an attempt to obtain stable crystalline salt/co-crystal form of Compound I with higher melting point than Compound I Form I (m.p.=78° C.). Salt/co-crystal screen was performed by crystallizations using 19 co-formers and afforded four crystalline salts/co-crystals with hydrochloric acid (Compound I HCl), methanesulfonic acid (Compound I MSA), benzenesulfonic acid (Compound I BSA) and p-toluenesulfonic acid (Compound I p-TSA). Co-crystal screen performed by dry grinding did not afford any new forms. All crystalline salts/co-crystals were analyzed by XRPD, DSC, TGA, NMR, and DVS and showed higher melting point (>100° C.) compared to Compound I Form I or Form II.

Abbreviated polymorph/stable form screens were performed for the selected co-crystals/salts: Compound I HCl showed three forms (Form XI, Form XII, and Form XIII), Compound I MSA showed only one form (Form IV), Compound I BSA showed two forms (Form V and Form VI), and Compound I p-TSA showed several forms with unique XRPD patterns (Form VII, Form VIII, Form IX, and Form X). Each of the crystalline co-crystal/salt forms afforded a higher melting point compared to Compound I Form I as summarized in Table 12 below.

TABLE 12

Summary of co-crystal/salt forms

| Compound I co-crystal | Form by XRPD | DSC (° C.) |
|---|---|---|
| Compound I HCl | Form XI | 119 |
|  | Form XII (hydrate) | 29, 126 |
|  | Form XIII | 123 |
| Compound MSA | Form IV | 185 |
| Compound I BSA | Form V (toluene solvate) | 80, 164 |
|  | Form VI | 164 |
| Compound I p-TSA | Form VII (EtOAc solvate) | 74, 106, 133 |
|  | Form VIII (anhydrous) | 109, ~130, 133 |
|  | Form IX | 46, 105, 134 |
|  | Form X* | 58, 134 |

*This form has 1.5 equivalent of the acid. All other forms have 1 equivalent of the acid.

Experiments, Results and Discussions

1. Co-Crystal/Salt Screen by Crystallization

Initial co-crystal/salt screen was conducted using 19 co-formers (Table 13). The following crystallization procedure was performed: Compound I Form I (about 50 mg) was dissolved in 1 mL of solvent (MeCN or other solvent as shown in Table 13) at 70° C., followed by the addition of 1.05 eq. of co-former (as 0.5M or 1M solutions). After about 5-10 min equilibration at about 70° C. all mixtures were cooled to room temperature and allowed to stir at room temperature overnight. Those samples that contain solids were isolated by filtration, dried under vacuum at room temperature (RT) and analyzed by XRPD (Table 13). Crystalline solids were obtained with p-TSA, MSA, BSA and HCl (using 4M HCl solution in dioxane). The samples were further characterized by DSC, TGA, etc. as described herein.

The samples which remained as oils were charged with 0.5 mL n-heptane and stirred overnight. None of them formed solids. Solvents were evaporated under gentle nitrogen flow, followed by the addition of 0.5 mL EtOAc and stirring at room temperature overnight. All mixtures afforded clear solutions, and no co-crystal formation was observed.

TABLE 13

Co-crystal/salt screen by crystallization

| Co-former (CF) | Solvent | Compound I Form by XRPD |
|---|---|---|
| Acetic Acid | MeCN | oil |
| Adipic acid |  | Form I + CF |
| Citric acid |  | oil |
| Fumaric acid |  | Fumaric acid |
| Glycine |  | Glycine |
| Glycolic acid |  | oil |
| Glutaric acid |  | oil |
| Maleic acid |  | oil |
| L-Malic acid |  | oil |
| L-Tartaric acid |  | oil |
| Succinic acid |  | Form I + CF |
| Urea |  | Form I + CF |
| p-TSA | EtOAc | Form VII (EtOAc solvate) |
| HCl (aq.) | Toluene | amorphous |
| Sulfuric acid |  | amorphous |
| MSA |  | Form IV |
| BSA |  | Form V (Toluene solvate) |
| Benzoic acid |  | oil |
| NDSA |  | NDSA |
| HCl (in dioxane) | IPA | Form XI |
|  | IPAc | Form XII (hydrate) |
|  | Dioxane | Form XIII |
|  | Toluene | Form XIII |
|  | MeCN | Form XIII |

2. Co-Crystal Screen by Grinding

Dry grinding was also performed using 14 co-formers in an attempt to obtain crystalline co-crystals. Compound I Form I (about 50 mg) was mixed with 1 molar equivalent of co-former, followed by ball-milling using Wig-L-Bug for 5 min. All obtained solids were analyzed by XRPD. No co-crystal formation was observed (Table 14).

TABLE 14

Co-crystal screen by grinding

| Co-former (CF) | Form by XRPD |
|---|---|
| Glycine | Form I + CF |
| Glycolic acid | Form I + CF + amorphous |
| Urea | Form I + CF |
| Maleic acid | amorphous + CF |
| Fumaric acid | Form I + CF |
| Succinic acid | Form I + CF |
| Glutaric acid | oil |
| L-Malic acid | amorphous |
| Adipic acid | Form I + CF |
| L-Tartaric acid | Form I + CF |
| Citric acid | amorphous + CF |
| D-Mannitol | Form I + CF |
| meso-Erythritol | Form I + CF |
| Saccharin | Form I + CF |

3. Stable Form Screens

Abbreviated stable form screens were conducted for the salt/co-crystals discovered in the salt/co-crystal screen, including MSA and BSA salts/co-crystals, to determine the stability of the crystalline forms. These salts/co-crystals were designated as Compound I MSA and Compound I BSA, respectively. All isolated solids were analyzed by XRPD to determine form conversion. Solids with unique XRPD patterns were further analyzed by DSC, TGA, $^1$H NMR, KF and DVS (if applicable) as discussed herein.

Stable form screens were not performed for Compound I HCl and Compound I p-TSA because several forms of each salt/co-crystal were obtained during salt/co-crystal formation in different organic solvents as discussed below.

i. 3.1 Stable Form Screen of Compound I Form IV

Stable form screen of Compound I Form IV was performed using 17 solvents in an attempt to determine the most stable form (Table 15). Compound I Form IV (about 50 mg) was slurried in 0.5-1 mL of solvent and allowed to stir at room temperature for 2 weeks. The first aliquot (about 0.3 mL) was taken after 24 h of stirring for XRPD analysis and solubility test. XRPD showed no form change in all solvents except water, which afforded Compound I Form III of wet material and a mixture of Form III and Form II after the overnight air drying. Similar results were observed after 2 weeks of equilibration (Table 15).

TABLE 15

Stable form screen of Compound I Form IV

| | Form after 24 h | | Solubility after 24 h | Form after 2 weeks | |
|---|---|---|---|---|---|
| Solvent | wet | air dried | (mg/mL) | wet | air dried |
| Water | Form III | Form III + Form II | 4.34 | Form III | Form III + Form II |
| EtOH/ water * | solution | solution | >150** | solution | solution |
| MeCN | Form IV | Form IV | 4.82 | Form IV | Form IV |
| MeOH | Form IV | Form IV | 40.36 | Form IV | n/a |

TABLE 15-continued

Stable form screen of Compound I Form IV

| Solvent | Form after 24 h wet | Form after 24 h air dried | Solubility after 24 h (mg/mL) | Form after 2 weeks wet | Form after 2 weeks air dried |
|---|---|---|---|---|---|
| EtOH | Form IV | Form IV | 12.24 | Form IV | n/a |
| IPA | Form IV | Form IV | 5.42 | Form IV | n/a |
| Acetone | Form IV | Form IV | 4.16 | Form IV | n/a |
| MEK | Form IV | Form IV | 3.14 | Form IV | n/a |
| MIBK | Form IV | Form IV | 1.42 | Form IV | n/a |
| DCM | Form IV | Form IV | 5.48 | Form IV | n/a |
| THF | Form IV | Form IV | 7.94 | Form IV | n/a |
| 2-Me-THF | Form IV | Form IV | 2.30 | Form IV | n/a |
| EtOAc | Form IV | Form IV | 1.26 | Form IV | n/a |
| IPAc | Form IV | Form IV | 0.78 | Form IV | n/a |
| MTBE | Form IV | Form IV | 0.34 | Form IV | n/a |
| Toluene | Form IV | Form IV | 0.36 | Form IV | n/a |
| Heptane | Form IV | Form IV | 0.10 | Form IV | n/a |

Starting material: Compound I Form IV
n/a = not analyzed.
* EtOH/water 0.8 water activity (480 µL H$_2$O and 520 µL EtOH)
** All solids were dissolved - solubility >150 mg/mL ii. 3.2 Abbreviated Stable Form Screen of Compound I Form V Abbreviated stable form screen of Compound I Four V was performed by slurrying Form I (about 100 mg) in IPA, IPAc and MTBE (1-2 mL) in an attempt to obtain anhydrous form as summarized in Table 16. The first aliquot (about 0.5 mL) was taken for XRPD analysis and solubility assessment after 3 days of equilibration at room temperature. Solids were analyzed before and after overnight drying at 45° C. XRPD patterns showed that all solids converted to anhydrous Compound I Form VI. After two weeks equilibration at room temperature no form change was observed. XRPD patterns of all samples were consistent with Compound I Form VI.

TABLE 16

Abbreviated stable form screen of Compound I Form V*

| Solvent | Form by XRPD 3 days | Solubility 3 days (mg/mL) | Form by XRPD 2 weeks |
|---|---|---|---|
| IPA | Form VI | 16.08 | Form VI |
| IPAc | Form VI | 2.20 | Form VI |
| MTBE | Form VI | 0.46 | Form VI |

*Starting material: Compound I Form V

4. Characterization of Crystalline Salts/Co-Crystals

The solids with unique XRPD patterns were characterized by DSC, TGA, $^1$H NMR, KF and DVS. All XRPD patterns were obtained in the experimental setting as follows: 45 kV, 40 mA, Kα$_1$=1.5406 Å, scan range 2 to 40°, step size 0.0167°, counting time: 15.24 s. DSC and TGA analyses were performed using 10° C./min heating rate over the 20 to 350° C. temperature range.

4.1 Compound I MSA

Only one crystalline form of Compound I MSA was discovered during salt/co-crystal screen and stable form screen. This form was designated as Compound I Form IV.

4.1.1 Compound I Form IV

Figure 3:
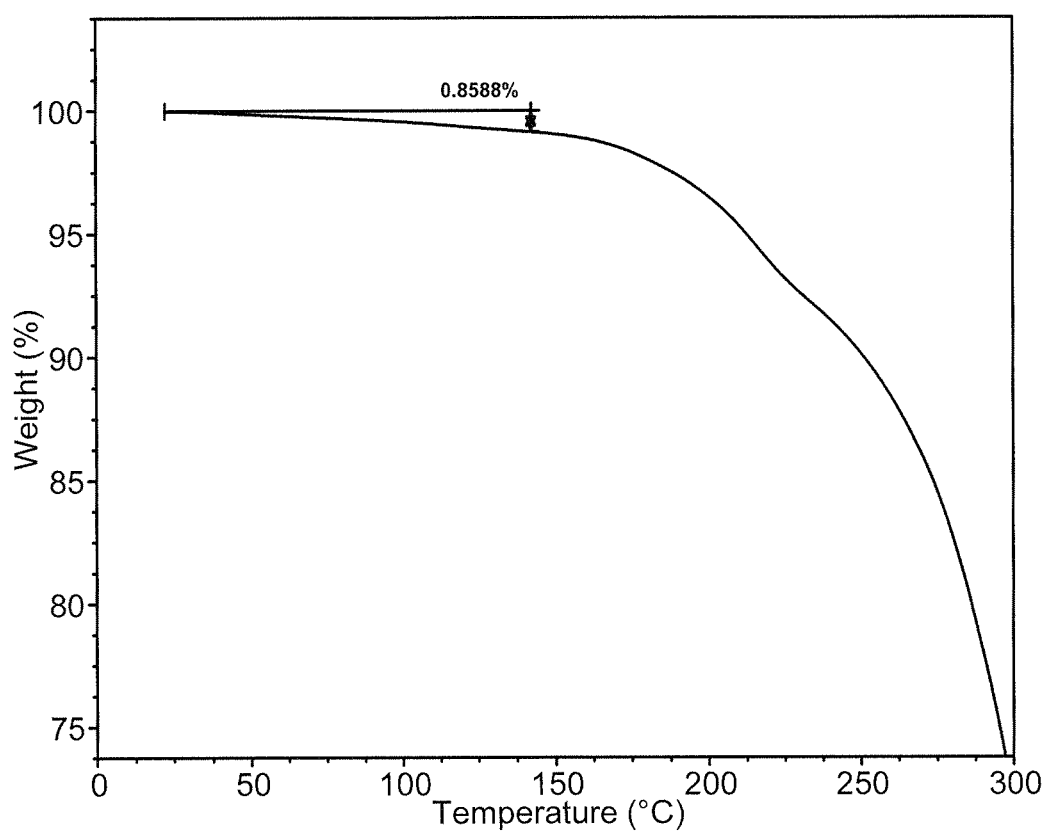
FIG. 3 shows a thermogravimetric analysis (TGA) of Compound I Form IV.
Figure 4:
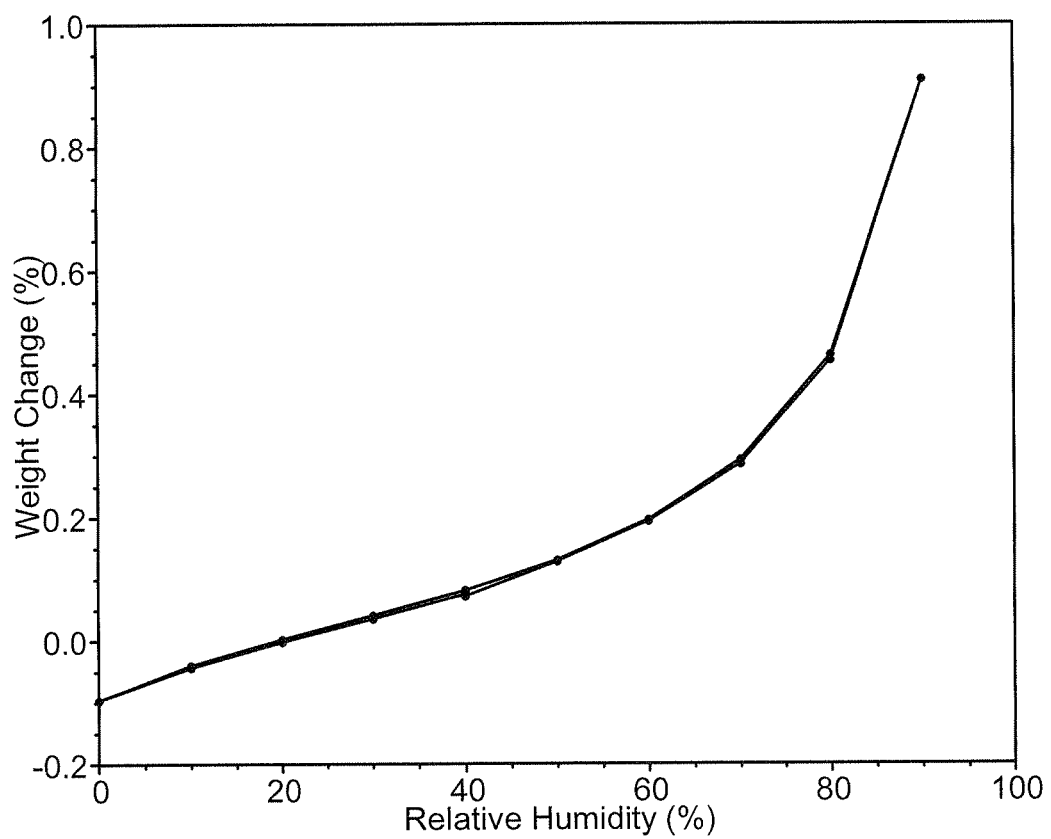
FIG. 4 shows a dynamic vapor sorption (DVS) curve of Compound I Form IV.

Compound I Form IV was obtained from toluene (about 10 volumes) with about one equivalent of MSA and was found to be crystalline by XRPD (FIG. 1). XRPD patterns of wet and dried material were consistent with each other. The characteristic peaks of Compound I Form IV include: 4.8, 14.2, 16.5, 18.9, 19.7, 20.6°2θ. $^1$H NMR spectrum was consistent with Compound I structure with 1 equivalent of MSA. DSC shows single endotherm with onset at 185° C. (FIG. 2). TGA shows 0.86% weight loss below 150° C. (FIG. 3). DVS analysis shows that Compound I Form IV is slightly hygroscopic with 1.0 wt % moisture uptake at 90% RH (FIG. 4). KF analysis shows 0.56% of water content.

(1) 4.1.2 Thermal Stability of Compound I Form IV at 45° C.

Drying study was also performed of Compound I Form IV under vacuum at 45° C. in an attempt to determine the chemical stability of this material by HPLC as well as form stability by XRPD. Sample was analyzed by XRPD and HPLC after 2 and 7 days of drying as summarized in Table 17. XRPD analysis did not show any form change during drying. HPLC analysis showed 100% (AUC) purity and 80 to 85% strength, compared to theoretical strength (81.21%).

TABLE 17

Stability of Compound I MSA co-crystals at 45° C.

| Drying time (days) | XRPD | HPLC (% ES) | HPLC (% AN) |
|---|---|---|---|
| 0 | Form IV | 80.2 | 100 |
| 2 | Form IV | 85.4 | 100 |
| 7 | Form IV | 82.1 | 100 |

Crystallization procedure (1 g scale): 1.05 equivalents of MSA (245 mg in 2 mL of 1:1 toluene/MeCN solvent mixture) were added to the solution of 1 g Compound I Form I in 8 mL toluene at room temperature. Solids started to form upon acid addition. The mixture was stirred at room temperature overnight. The solids were isolated by filtration, washed with 1 mL toluene and dried under vacuum at room temperature for 2-3 days to afford Compound I Form IV.

iii. 4.2 Compound I BSA

Two crystalline forms of Compound I BSA were discovered during salt/co-crystal screen: Form V—toluene solvate and Form VI—anhydrous form.

(1) 4.2.1 Compound I Form V (Toluene Solvate)

Figure 5:
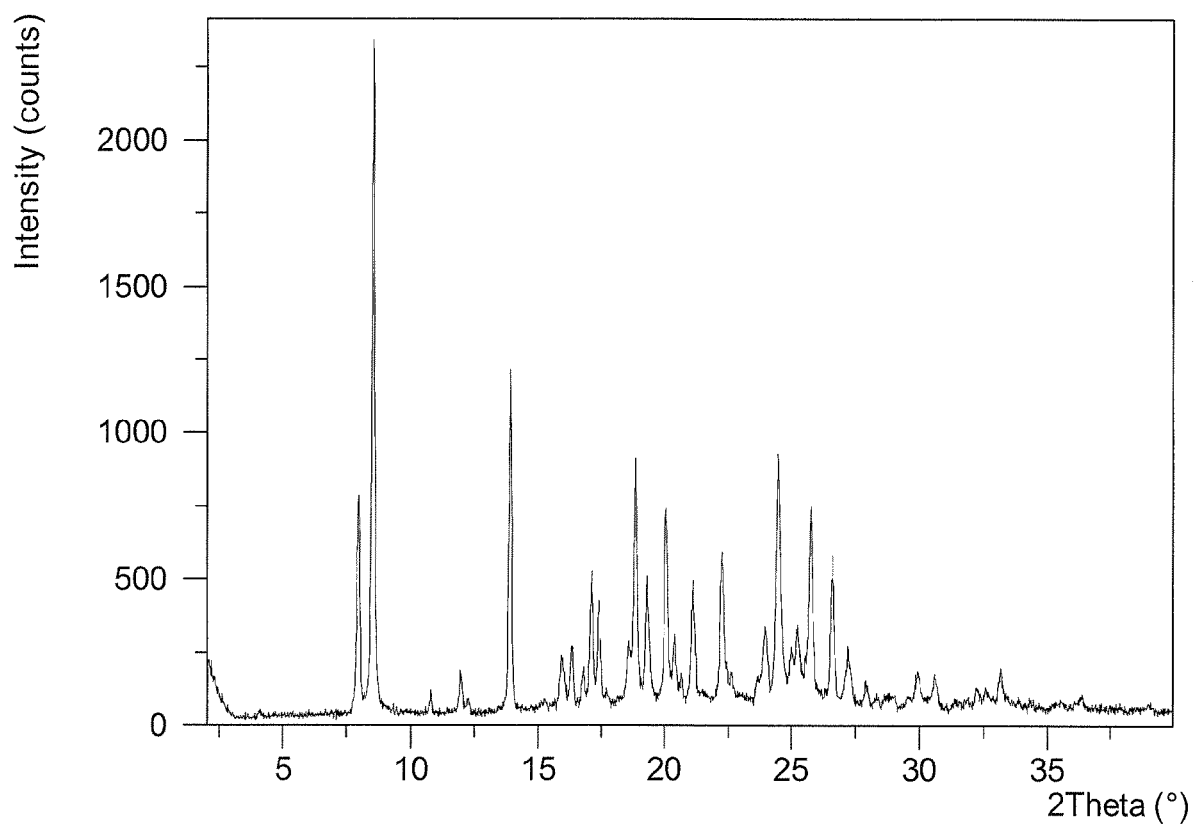
FIG. 5 shows an X-ray powder diffraction (XRPD) of Compound I Form V.
Figure 7:
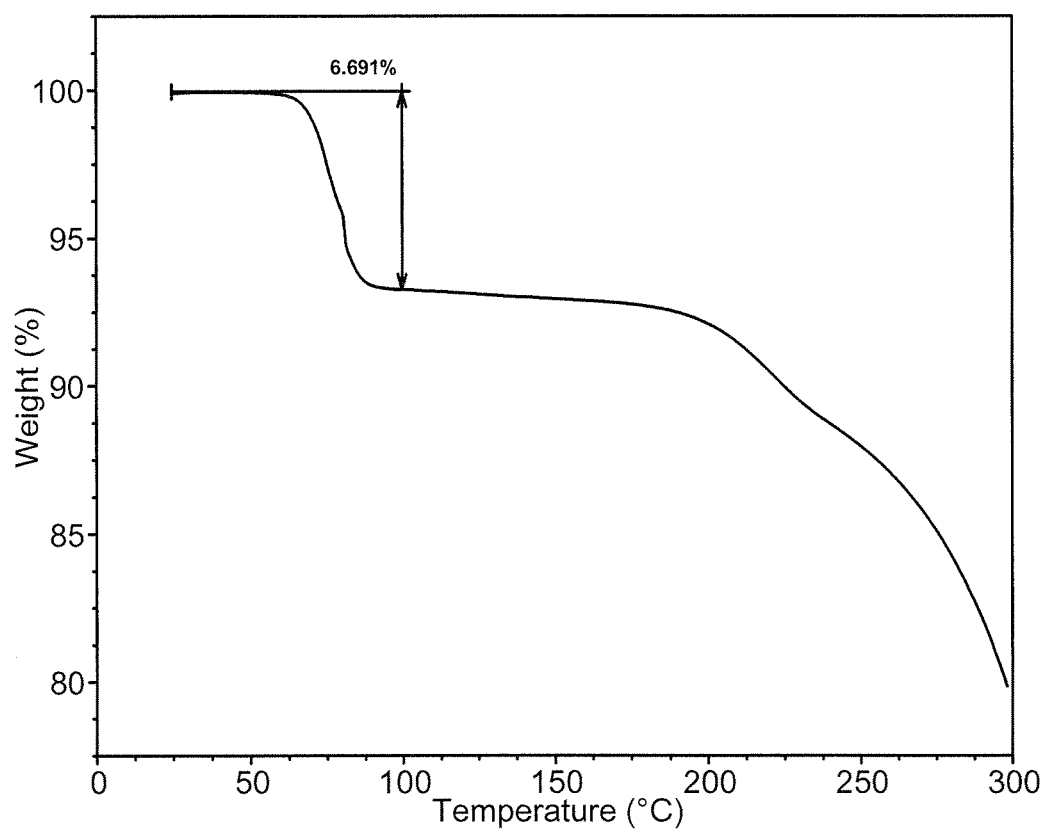
FIG. 7 shows a thermogravimetric analysis (TGA) of Compound I Form V.

Compound I Form V was obtained from toluene with one equivalent of BSA and was found to be crystalline by XRPD (FIG. 5). The characteristic peaks of Compound I Form V include: 8.0, 8.6, 13.9, 17.1, 18.9, 20.1°2θ. Solids were also analyzed by DSC, TGA and $^1$H NMR. DSC shows two endothermic events with onsets at about 80 and 165° C., corresponding to solvent loss and melting, respectively (FIG. 6). TGA shows 6.7% weight loss at about 50 to 90° C. (FIG. 7), corresponding to solvent loss. It was confirmed by $^1$H NMR that the solids contains 0.44 equivalents of toluene (about 6.6 wt %). These data suggests that Compound I Form V is a toluene solvate.

Crystallization procedure (1 g scale): Compound I Form V was obtained by dissolving Compound I Form I (1 g) in 9 mL of toluene, followed by the addition of 1.05 equivalents of BSA (400 mg dissolved in 1 mL MeCN). Thick precipitate was formed within 5 min after the acid addition. Toluene (5 mL) was added to improve stirring. The reaction mixture was allowed to stir at room temperature overnight. Solids were isolated by filtration, washed with toluene (1 mL) and dried under vacuum at about 45° C. overnight to afford Compound I Form V.

(2) 4.2.2 Compound I Form VI (Anhydrous Form)

Figure 8:
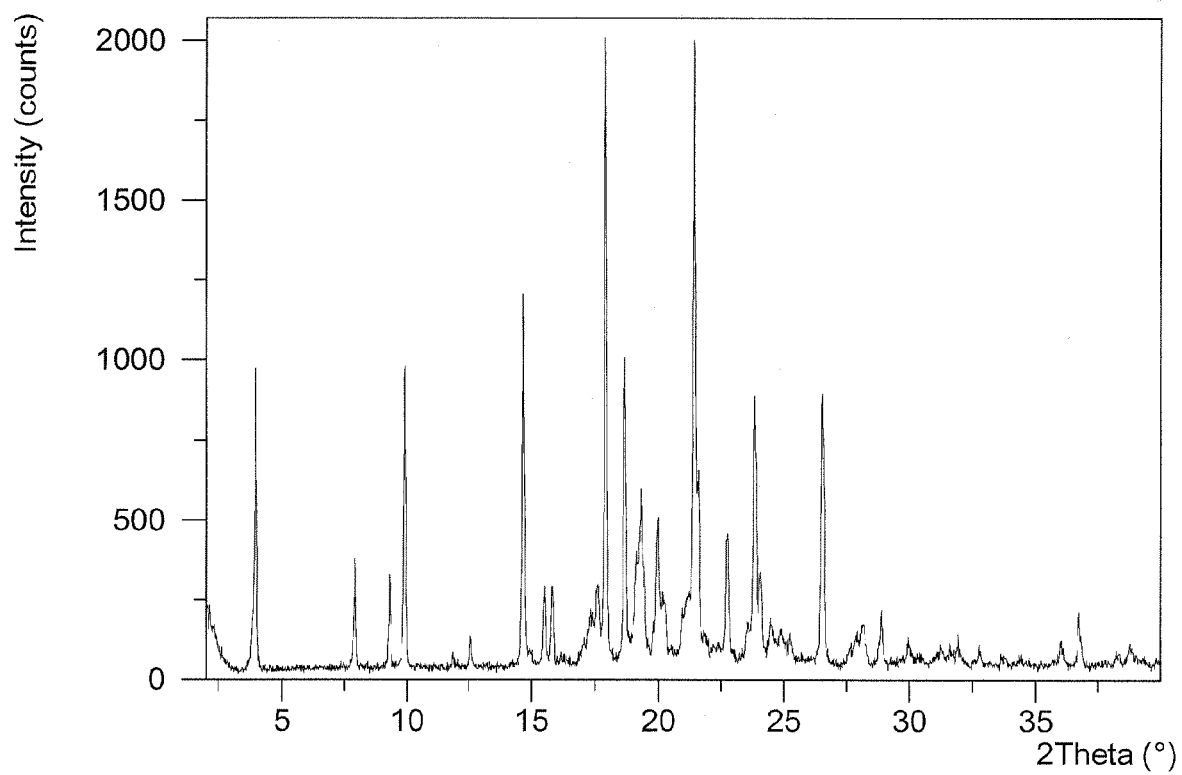
FIG. 8 shows an X-ray powder diffraction (XRPD) of Compound I Form VI.
Figure 10:
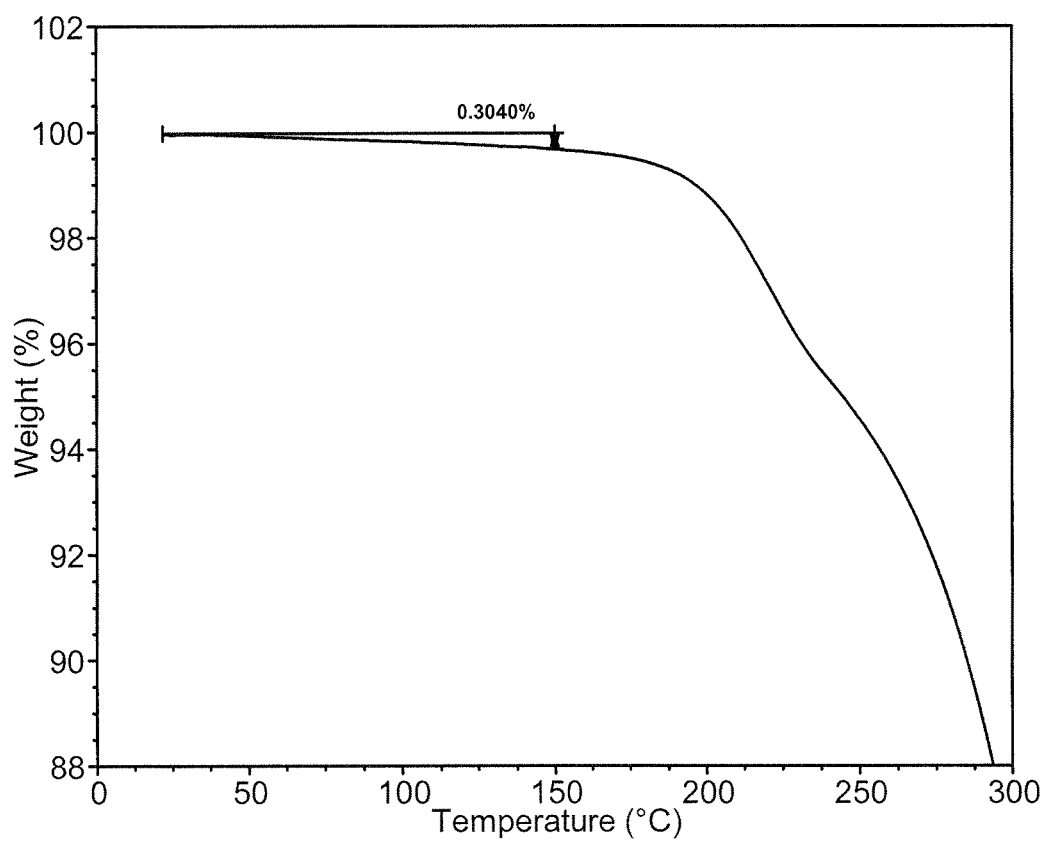
FIG. 10 shows a thermogravimetric analysis (TGA) of Compound I Form VI.
Figure 11:
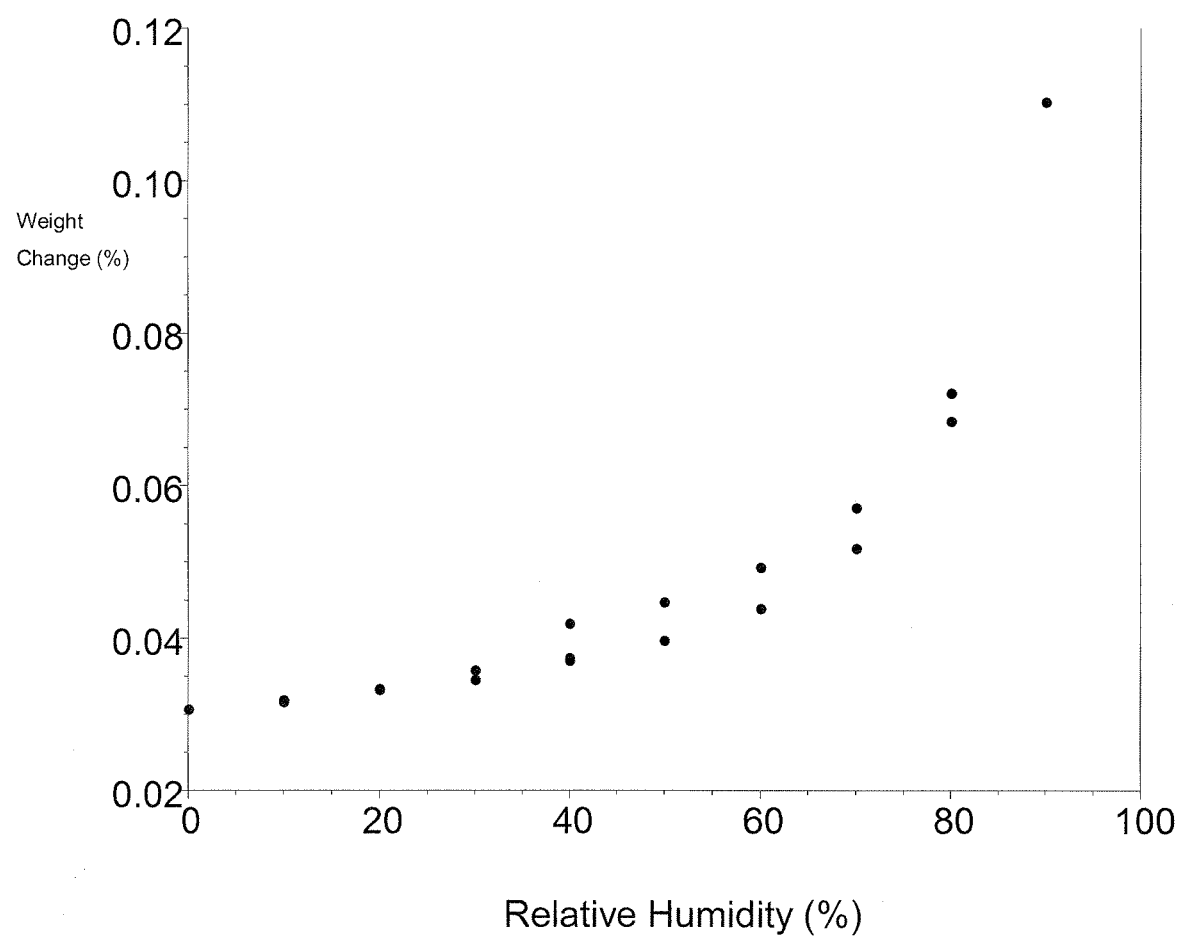
FIG. 11 shows a dynamic vapor sorption (DVS) curve of Compound I Form VI.

Compound I Form VI was obtained from the slurries of Compound I Form V in IPA, IPAc and MTBE. It was also obtained from the salt formation in IPAc/MeCN with one equivalent of BSA. XRPD analysis of Compound I Form VI showed a unique pattern with the following characteristic peaks: 4.0, 7.9, 9.3, 9.9, 14.7, 17.9°2θ (FIG. 8). A representative sample of Compound I Form VI was also analyzed by DSC, TGA, DVS, KF, $^1$H NMR and HPLC. DSC shows a single endotherm with onset at 164° C. (FIG. 9). TGA shows 0.3% of weight loss below about 155° C. (FIG. 10). $^1$H NMR was consistent with Compound I structure with 1 equivalent of BSA and no residual solvents. KF analysis showed 0.0 wt % moisture content. DVS analysis confirmed that Compound I Form VI is non-hygroscopic, which absorbs about 0.1% moisture at 90% RH (FIG. 11). HPLC shows 98.9% AN purity.

Conversion procedure of Compound I Form V to Form VI in IPA: Compound I Form V (850 mg) was stirred in IPA (17 mL, 20 volumes) at room temperature overnight. Thick precipitate was formed within 10 min of stirring. The obtained solids were isolated by filtration and dried under vacuum at 45° C. overnight.

Crystallization procedure of Compound I Form VI from IPAc/MeCN: In an attempt to avoid formation of Compound I Form V (BSA toluene solvate), IPAc was used as a primary solvent (9 volumes) to dissolve Compound I Form I (0.5 g) at room temperature. To the solution, 1.05 equivalents of BSA (solution in MeCN, 1 volume based on Compound I) was added. No precipitation was observed after 1 h stirring at room temperature. A small amount of Compound I Form VI seeds was added. Precipitates started to form immediately after the addition of seeds. The reaction mixture was allowed to stir at room temperature overnight. The solids were isolated by filtration, washed with IPAc (3 volumes) and dried under vacuum at about 45° C. overnight to afford Compound I Form VI, which was confirmed by XRPD.

iv. 4.3 Compound I p-TSA

Figure 46:
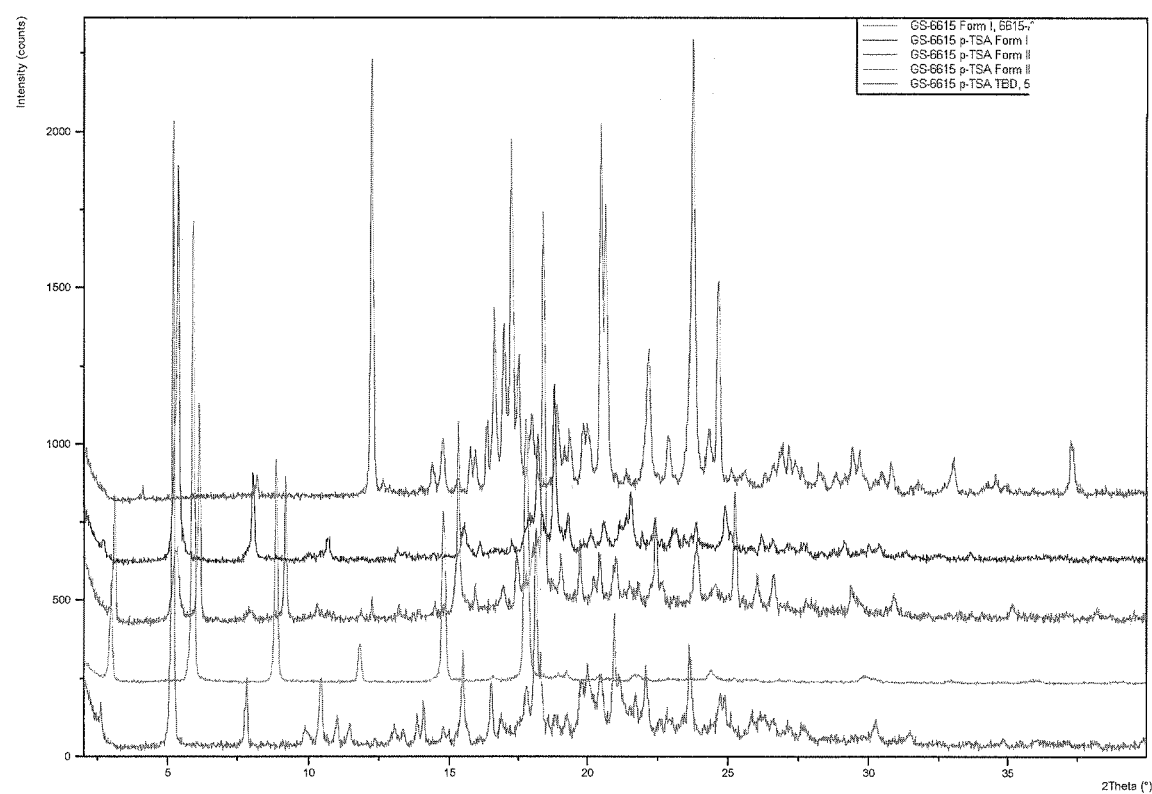
FIG. 46 shows XRPD patterns of Compound I Form I (top trace), Compound I Form VII (second from top trace), Compound I Form VIII (center trace), Compound I Form IX (second from bottom trace), and Compound I Form X (bottom trace).

Several crystalline polymorphic forms were obtained for Compound I p-TSA during salt/co-crystal screen (FIG. 46): Compound I Form VII, Compound I Form VIII, Compound I Form IX and Compound I Form X.

(1) 4.3.1 Compound I Form VII (EtOAc Solvate)

Figure 12:
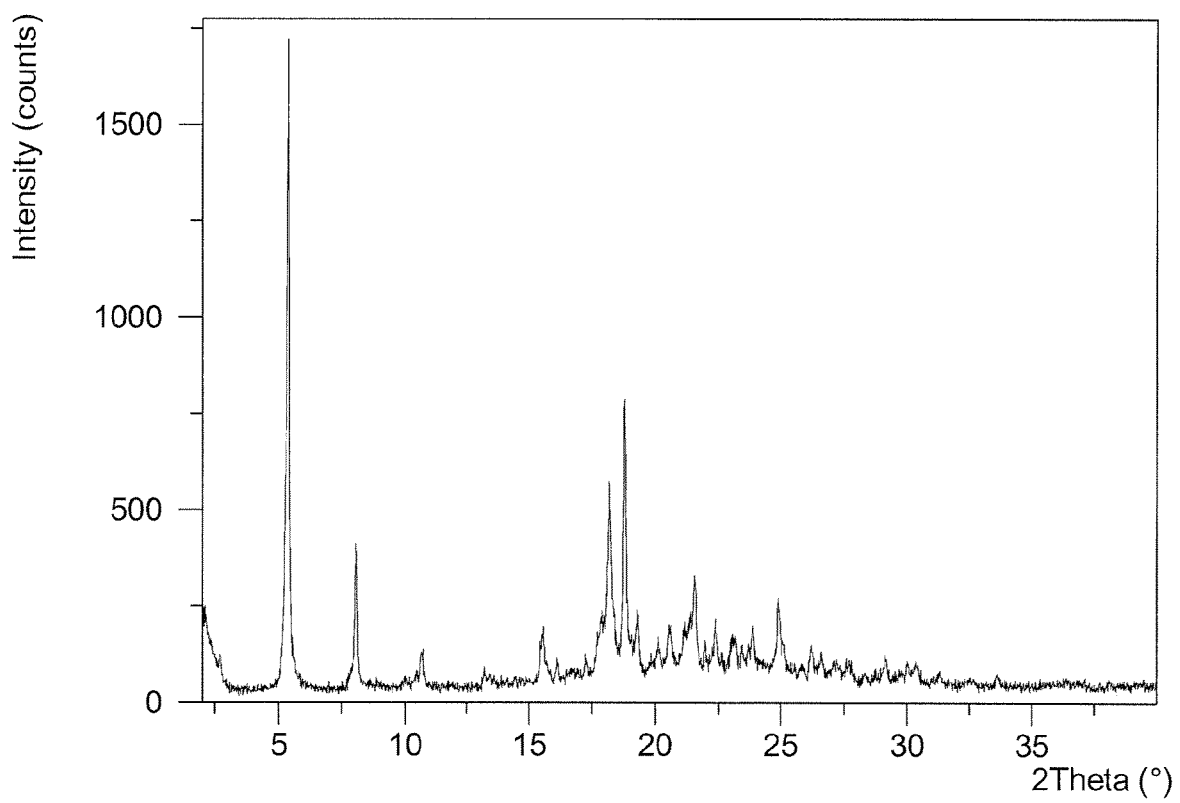
FIG. 12 shows an X-ray powder diffraction (XRPD) of Compound I Form VII.
Figure 14:
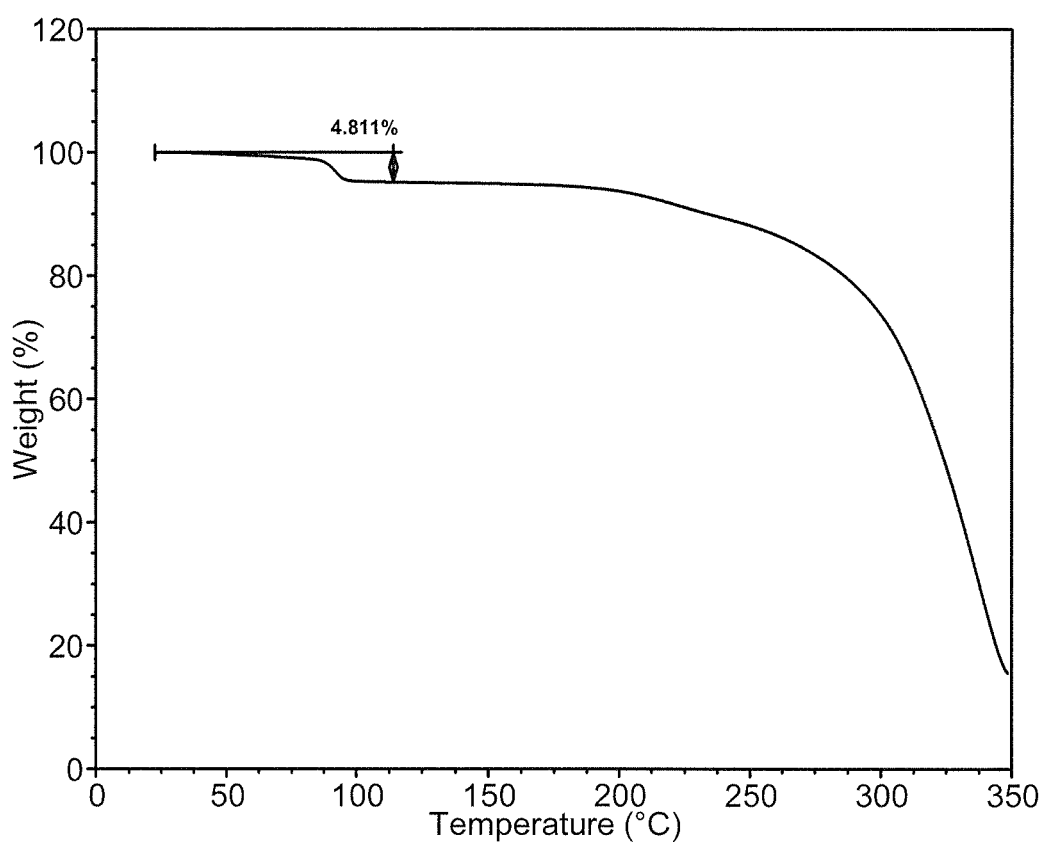
FIG. 14 shows a thermogravimetric analysis (TGA) of Compound I Form VII.
Figure 15:
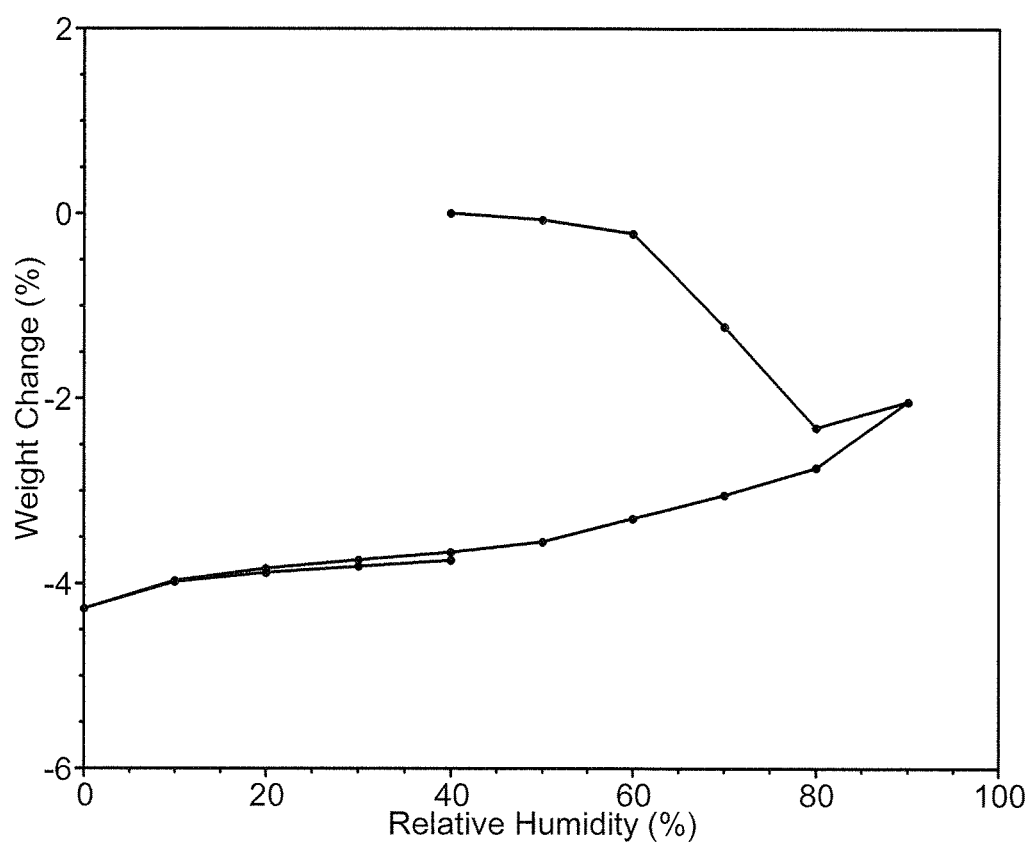
FIG. 15 shows a dynamic vapor sorption (DVS) curve of Compound I Form VII.

Crystalline Compound I Form VII was obtained in EtOAc with 1 eq. p-TSA mono-hydrate as a co-former, and afforded solids with a unique XRPD pattern. The characteristic peaks of Compound I Form VII include: 5.4, 8.1, 15.5, 18.2, 18.8°2θ (FIG. 12). The solids were analyzed by DSC, TGA, $^1$H NMR and DVS. DSC shows broad endotherm at about 74° C., followed by melting with onset at 106° C., recrystallization and another melting event with onset at about 133° C. (FIG. 13). TGA shows 4.8% bound weight loss below about 100° C. (FIG. 14). $^1$H NMR spectrum is consistent with Compound I structure with about 1 molar equivalent of p-TSA and 0.2 molar equivalents of EtOAc (about 4.1 wt %) suggesting that this form is an EtOAc solvate. Based on DVS analysis (FIG. 15) this form is moderately hygroscopic adsorbing about 2.75 wt % water (about 0.9 molar equivalents) at 90% RH.

A dissolution test of Compound I Form VII (about 8 mg) and 0.5 mL of DI water was performed. The solids were almost completely dissolved at first, and then more solids precipitated out. The slurry was allowed to be stirred overnight at room temperature before XRPD and $^1$H NMR analyses, which confirm Compound I free base (Form I). This experiment shows that Compound I Form VII is unstable in water and dissociates in it.

Crystallization procedure: 25 mg of p-TSA mono-hydrate (about 0.05 eq.) was dissolved in 1 mL of EtOAc at 70° C., followed by addition of Compound I Form I (50 mg). Precipitates were formed immediately after dissolution. The reaction mixture was allowed to stir at about 70° C. for 1 h. The solids were isolated by vacuum filtration, washed with EtOAc and dried under vacuum at room temperature.

(2) 4.3.2 Compound I Form VIII (Anhydrous Form)

Figure 16:
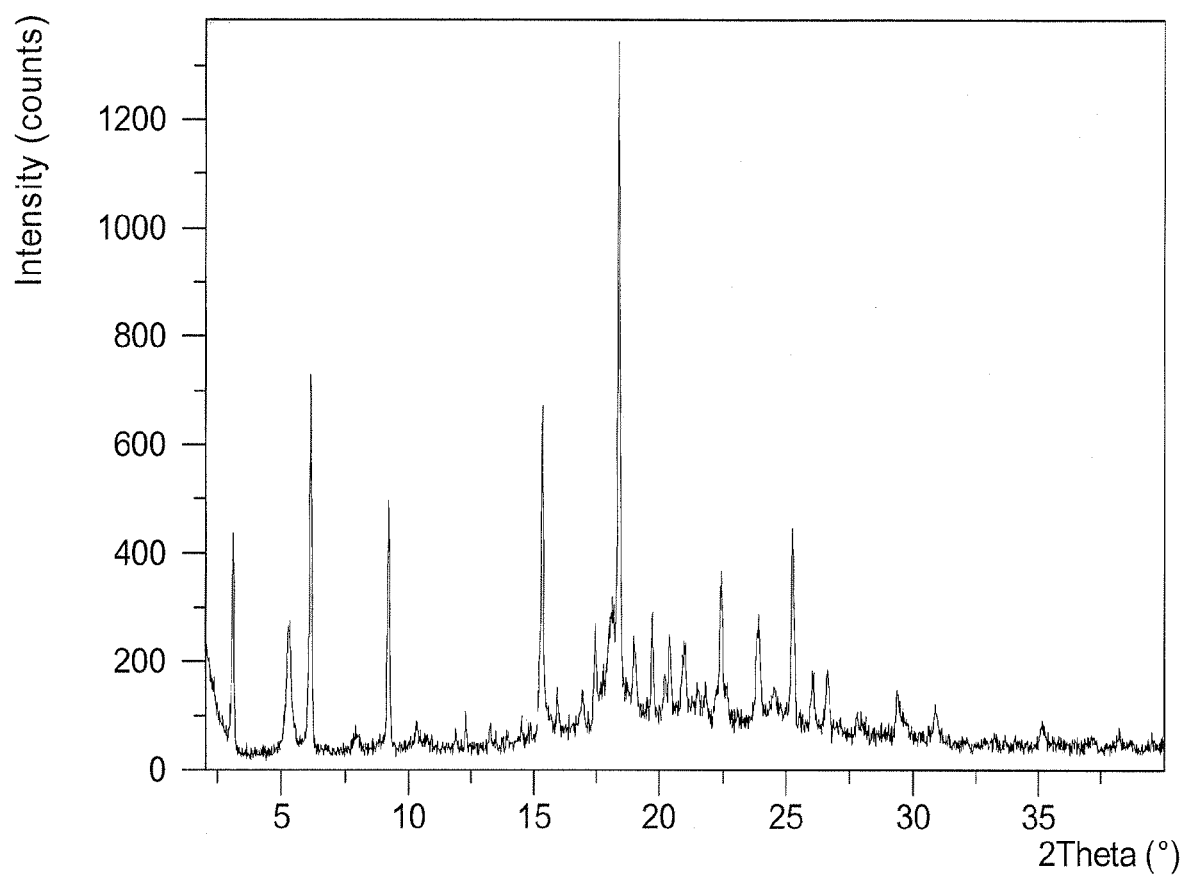
FIG. 16 shows an X-ray powder diffraction (XRPD) of Compound I Form VIII.

A sample of Compound I Form VII was used for DVS analysis and dried afterwards at about 60° C. at 0% RH for about 2 h to determine the dry weight. The XRPD pattern of this sample was different from that of the starting material (before DVS analysis), and it was most likely due to desolvation. This material was designated as Compound I Form VIII (anhydrous form). The characteristic peaks of Compound I Form VIII include: 3.1, 5.3, 6.2, 9.2, 15.3, 18.4°2θ (FIG. 16). DSC shows a small endothermic event with onset at about 109° C. and two endothermic events with onsets at about 130 and 133° C. (FIG. 17). $^1$H NMR spectrum is consistent with the Compound I structure with about 1 eq. of p-TSA and no residual EtOAc.

(3) 4.3.3 Compound I Form IX

Figure 18:
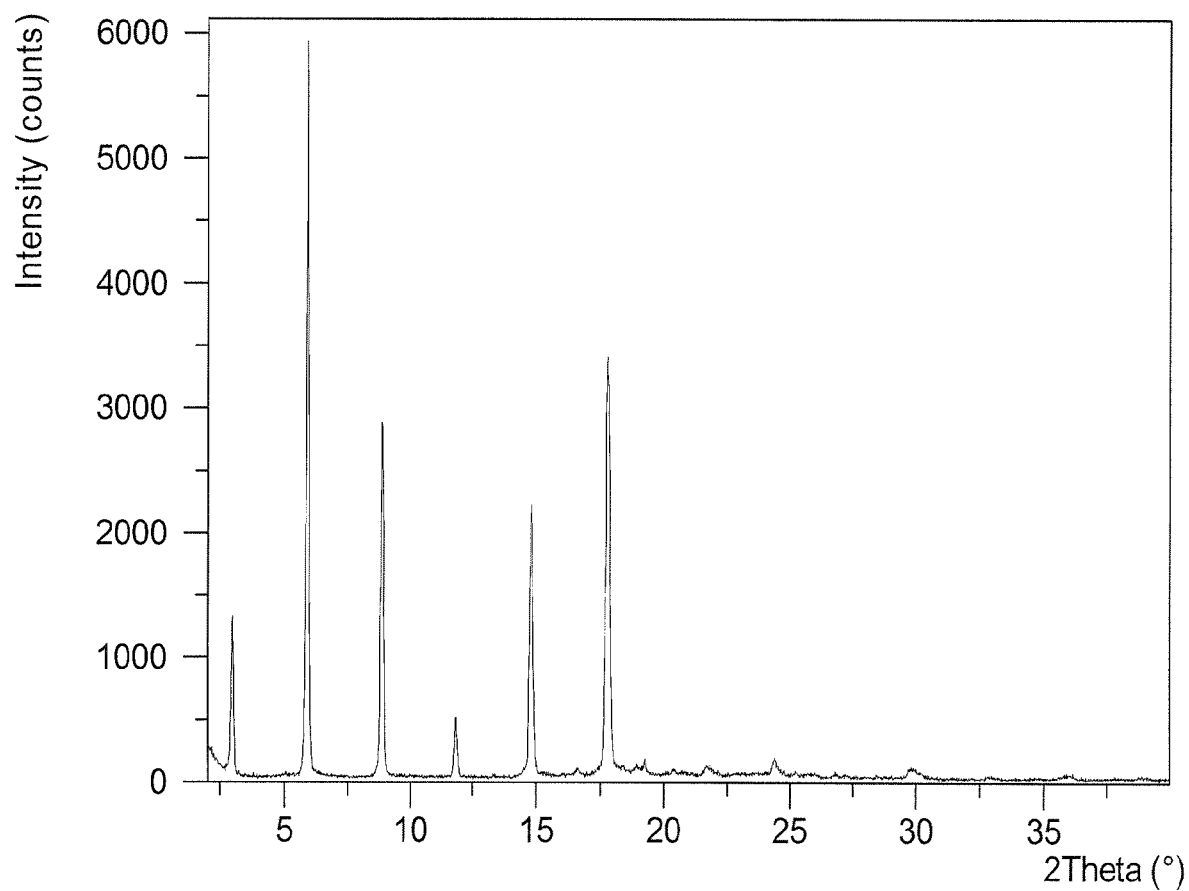
FIG. 18 shows an X-ray powder diffraction (XRPD) of Compound I Form IX.
Figure 20:
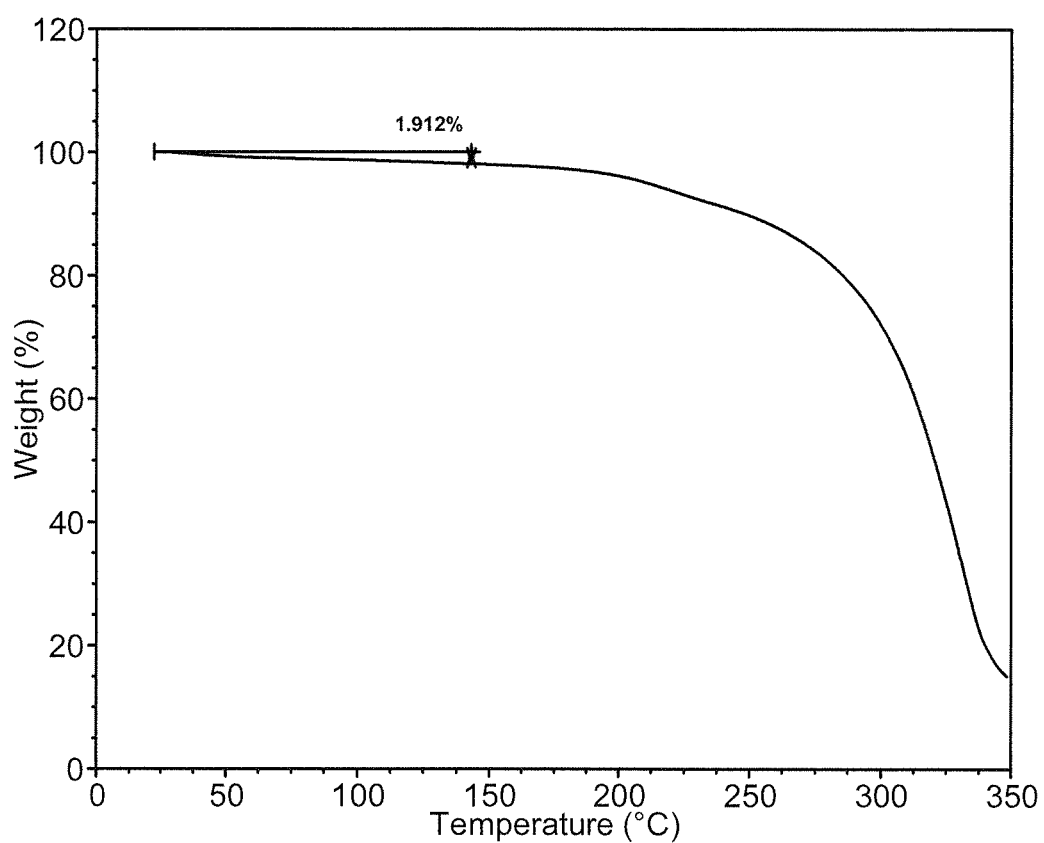
FIG. 20 shows a thermogravimetric analysis (TGA) of Compound I Form IX.

Compound I Form IX was obtained from MeCN by mixing a solution of Compound I Form I in 10 volumes of MeCN and a solution of p-TSA (1 eq. in 10 vol. of MeCN). No precipitation was observed. Then the reaction mixture was concentrated to dryness. The residual solids were dried under vacuum at about 40° C. and were analyzed by XRPD, DSC, TGA and $^1$H NMR. XRPD afforded a unique pattern. The characteristic peaks of Compound I Form IX include: 3.0, 5.9, 8.9, 11.8, 14.8, 17.7°2θ (FIG. 18). $^1$H NMR spectrum is consistent with Compound I structure with 1 eq. p-TSA. DSC shows a small and broad endothermic event with onset at 46° C., followed by two endothermic events with onsets at about 105 and 134° C. (FIG. 19). TGA shows 1.91% weight loss below about 140° C., most likely due to the loss of residual solvent (FIG. 20).

(4) 4.3.4 Compound I Form X

A new form, Compound I Form X, was obtained from toluene/MeCN using the following procedure: The solution of 1.05 eq. Compound I Form VII in MeCN (25 mg in 250 μL) was added to the solution of Compound I Form I in toluene (50 mg in 0.5 mL) affording clear solution. A small amount of Compound I Form IX seeds (<1 mg) was added. The precipitate started to form immediately. The reaction mixture was stirred at room temperature overnight. Solids were isolated by filtration, washed with 1 mL toluene and dried under vacuum at room temperature over two to three days.

Figure 21:
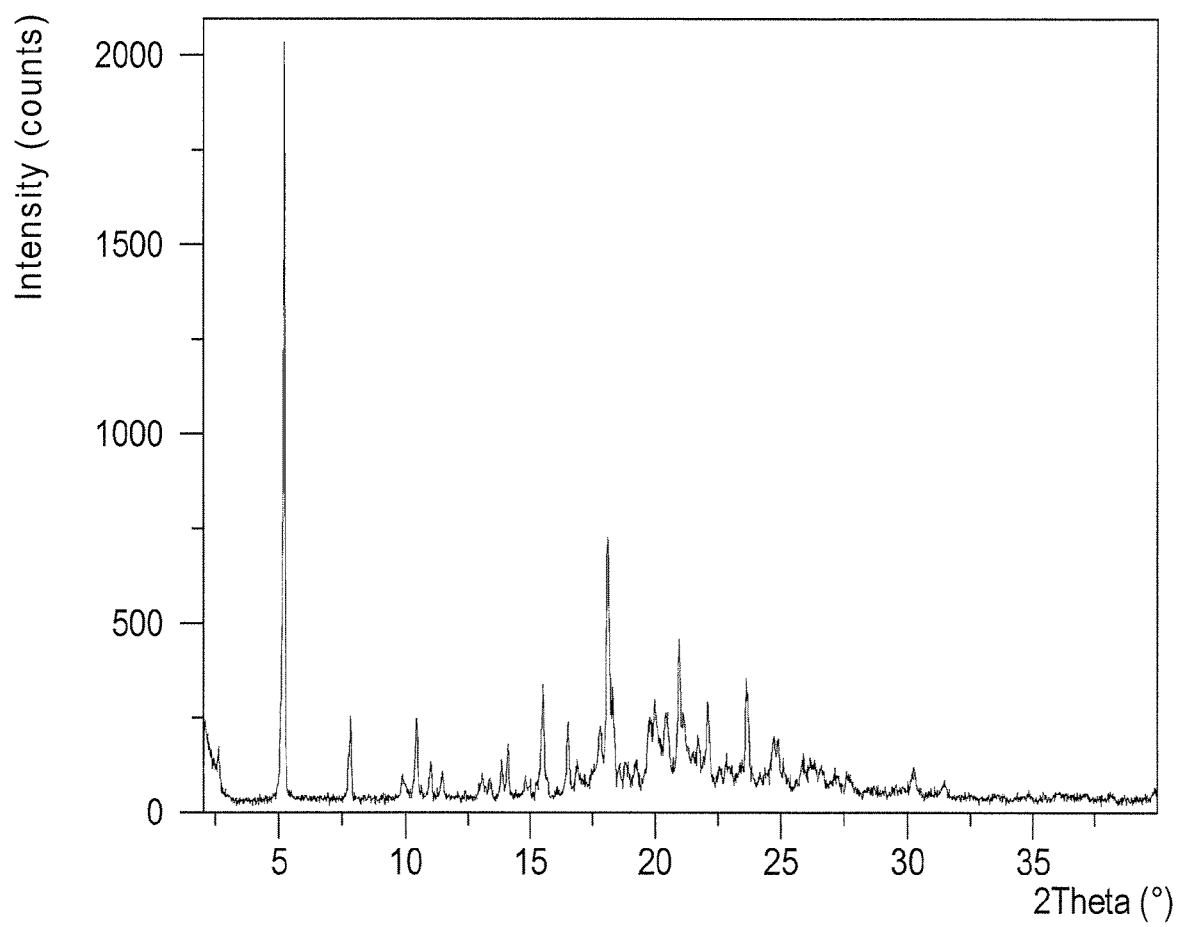
FIG. 21 shows an X-ray powder diffraction (XRPD) of Compound I Form X.
Figure 23:
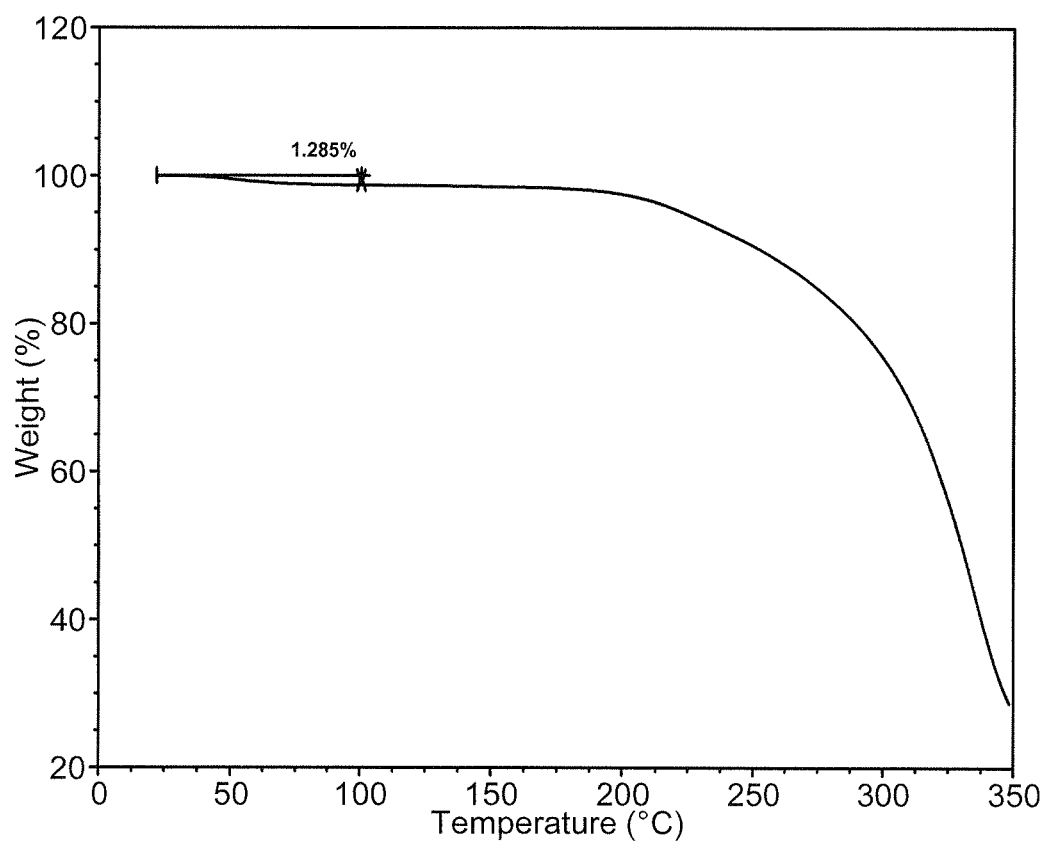
FIG. 23 shows a thermogravimetric analysis (TGA) of Compound I Form X.

The oven dried solids were analyzed by XRPD, DSC, TGA, KF and $^1$H NMR. XRPD shows a unique pattern with the following characteristic peaks of Compound I Form X: 5.2, 7.8, 10.5, 15.5, 18.1°2θ (FIG. 21). DSC shows broad endotherm with onset at about 58° C. followed by melting with onset at 134° C. (FIG. 22). TGA shows 1.28% weight loss below about 100° C. (FIG. 23), which correlates with KF data of 1.16 wt % water (about 0.4 molar equivalent). $^1$H NMR spectrum is consistent with structure and shows about 1.5 eq. p-TSA and no residual solvents. This material is most likely is a hemi-hydrate of Compound I•1.5 p-TSA. This form was designated as Compound I Form X.

v. 4.4 Compound I Form XI

Initially aqueous solution of HCl was used in the salt/co-crystal screen, which afforded amorphous material. However, using 4M HCl solution in dioxane for the salt formation in different organic solvents afforded three crystalline polymorphs of Compound I HCl: two most likely anhydrous forms—Form XI and Form XIII; and Form XII, which is a hydrated form.

Figure 47:
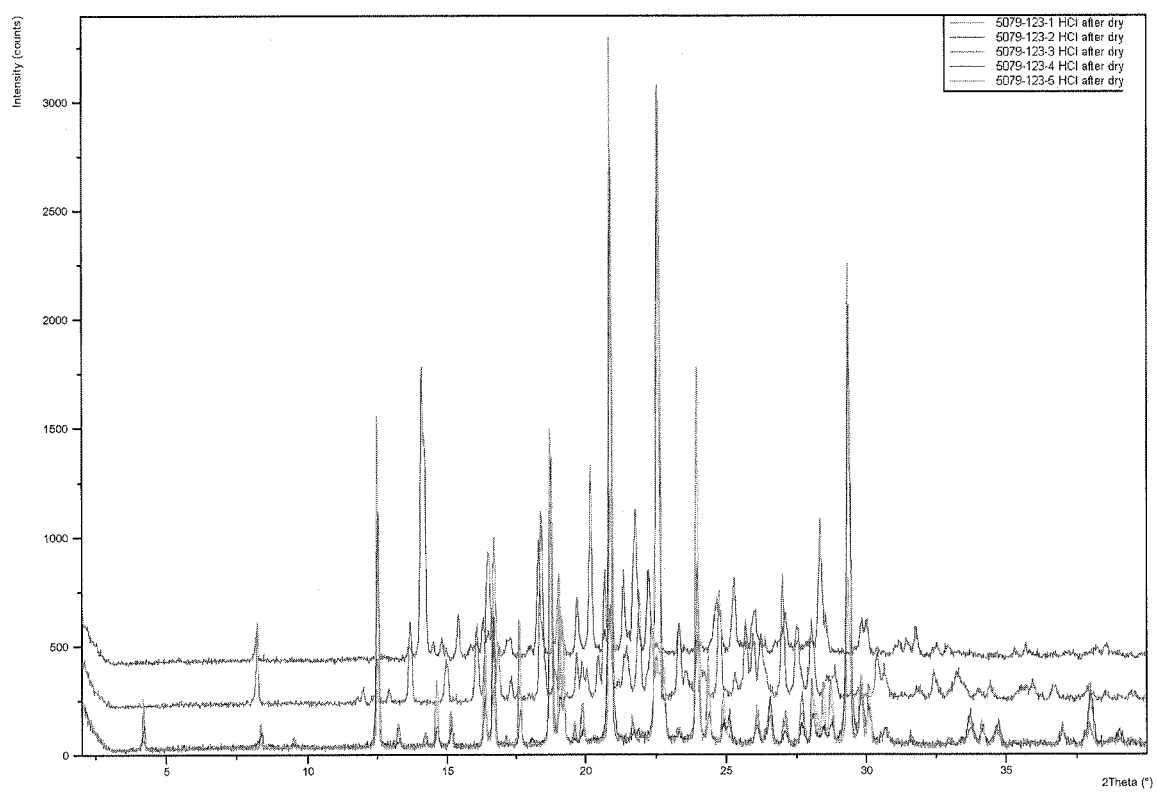
FIG. 47 shows XRPD patterns of Compound I Form XI (top trace), Compound I Form XII (center trace), and Compound I Form XIII (three lots, bottom traces).
Figure 48:
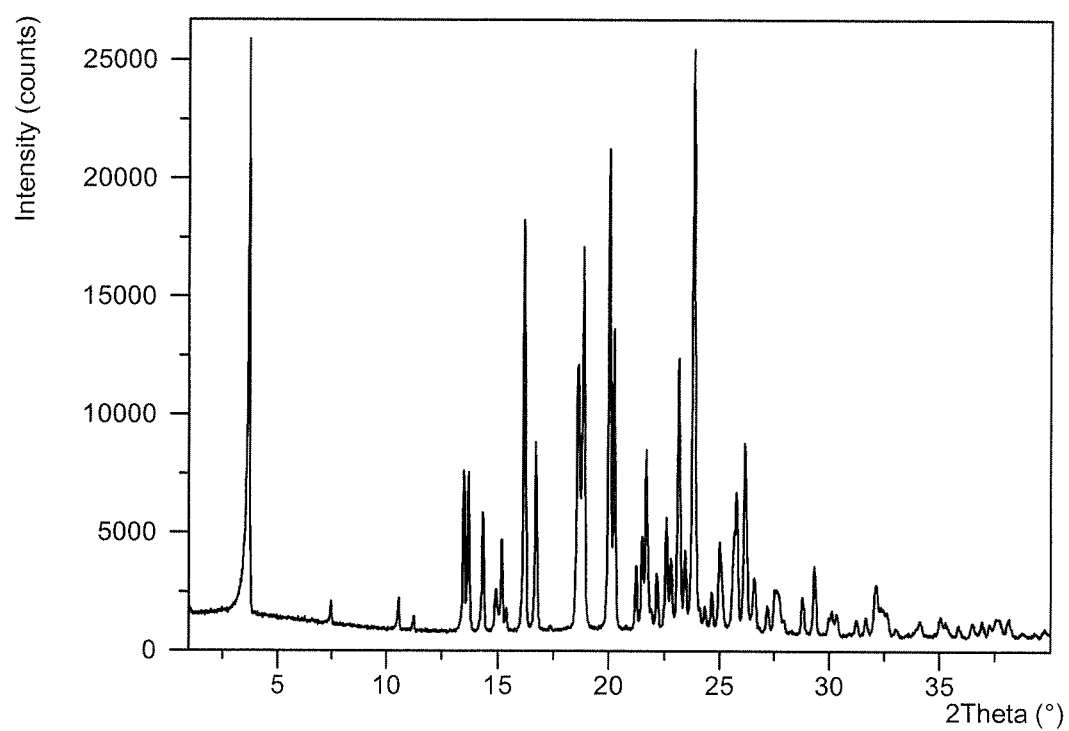
FIG. 48 shows XRPD pattern of crystalline 4-(pyrimidin-2-ylmethyl)-7-(4-(trifluoromethoxy)phenyl)-3,4-dihydrobenzo[f][1,4]oxazepin-5(2H)-one mono sulfate (Compound I Form XIV).
Figure 49:
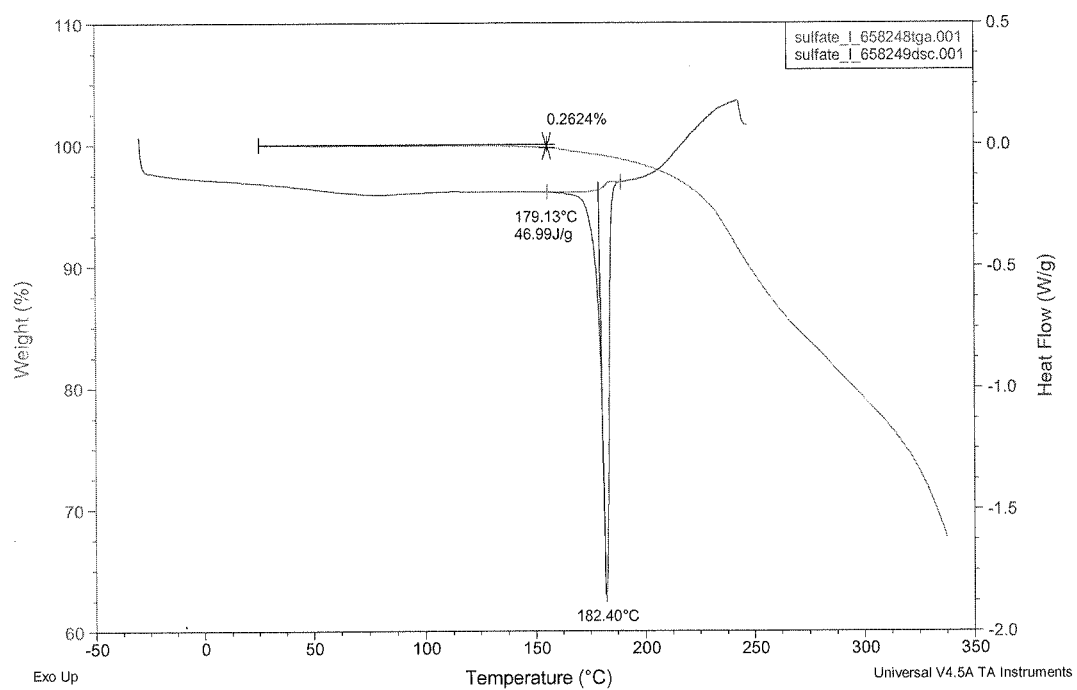
FIG. 49 shows TGA and DSC data of crystalline 4-(pyrimidin-2-ylmethyl)-7-(4-(trifluoromethoxy)phenyl)-3,4-dihydrobenzo[f][1,4]oxazepin-5 (2H)-one mono sulfate (Compound I Form XIV).
Figure 50:
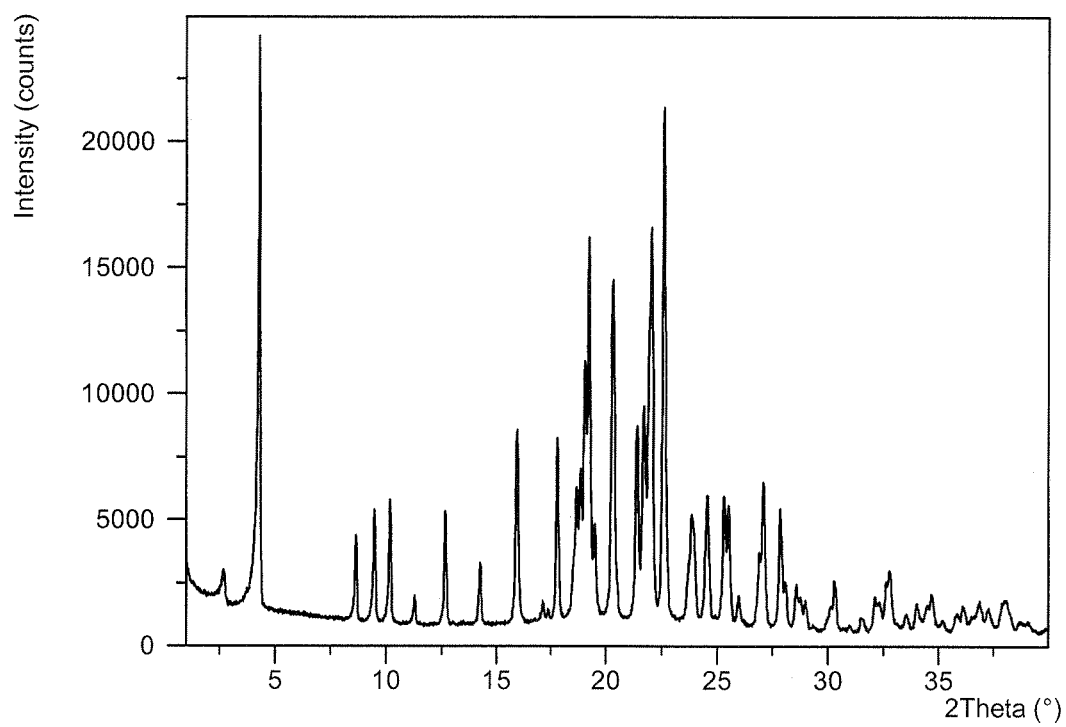
FIG. 50 shows XRPD pattern of crystalline 4-(pyrimidin-2-ylmethyl)-7-(4-(trifluoromethoxy)phenyl)-3,4-dihydrobenzo[f][1,4]oxazepin-5 (2H)-one mono sulfate (Compound I Form XV).
Figure 51:
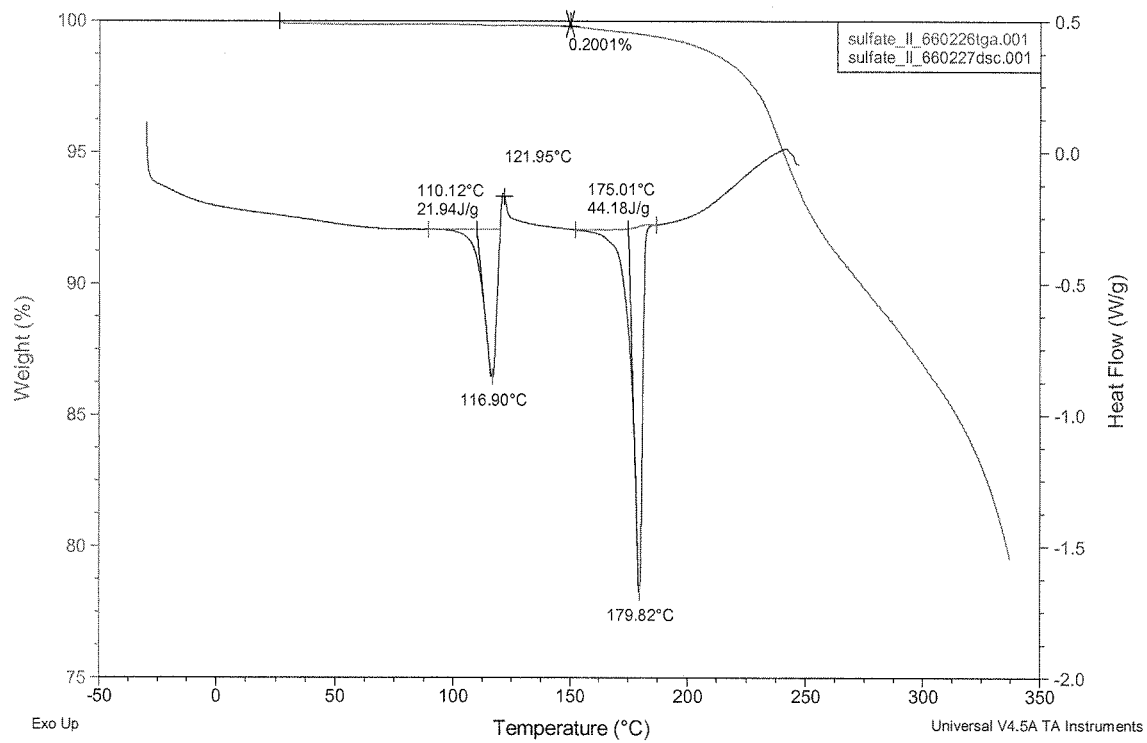
FIG. 51 shows TGA and DSC data of crystalline 4-(pyrimidin-2-ylmethyl)-7-(4-(trifluoromethoxy)phenyl)-3,4-dihydrobenzo[f][1,4]oxazepin-5 (2H)-one mono sulfate (Compound I Form XV).
Figure 52:
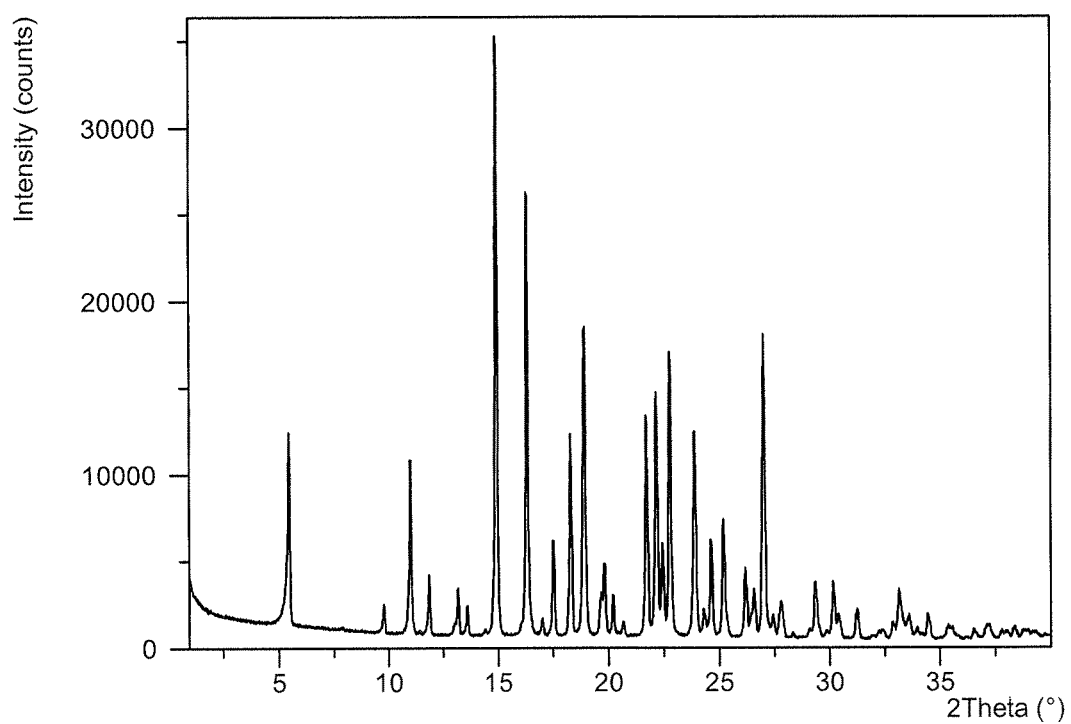
FIG. 52 shows XRPD pattern of crystalline 4-(pyrimidin-2-ylmethyl)-7-(4-(trifluoromethoxy)phenyl)-3,4-dihydrobenzo[f][1,4]oxazepin-5(2H)-one esylate (Compound I Form XVI).
Figure 53:
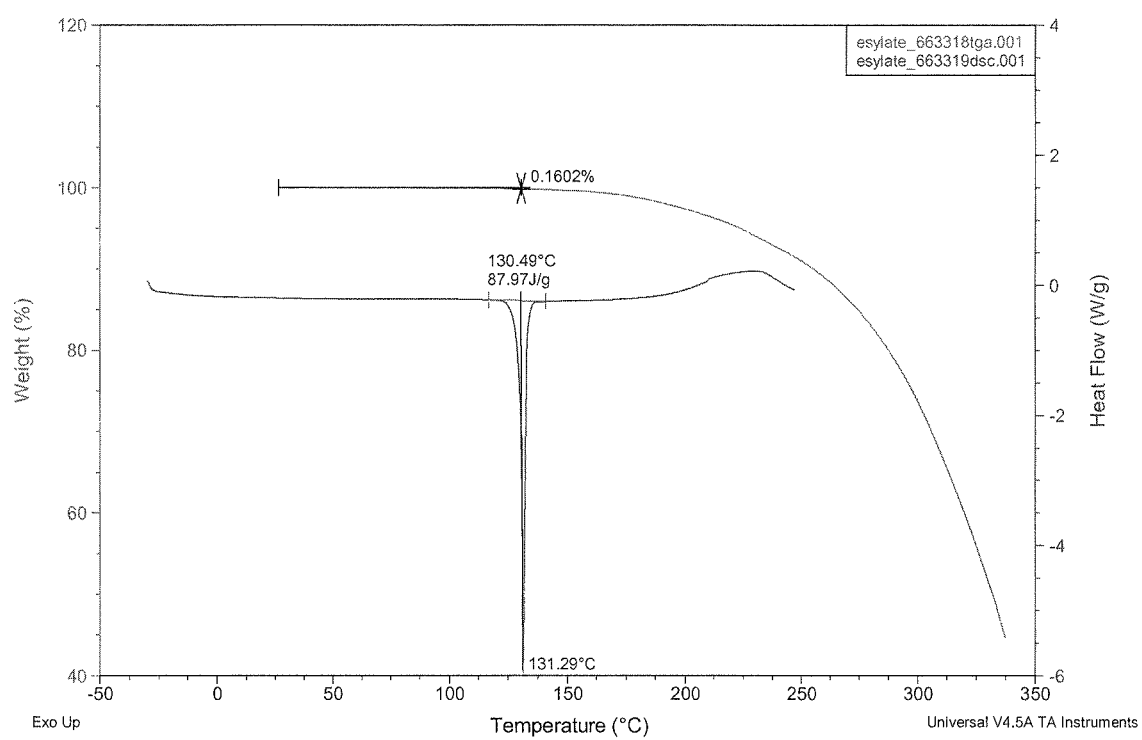
FIG. 53 shows TGA and DSC data of crystalline 4-(pyrimidin-2-ylmethyl)-7-(4-(trifluoromethoxy)phenyl)-3,4-dihydrobenzo[f][1,4]oxazepin-5(2H)-one esylate (Compound I Form XVI).
Figure 54:
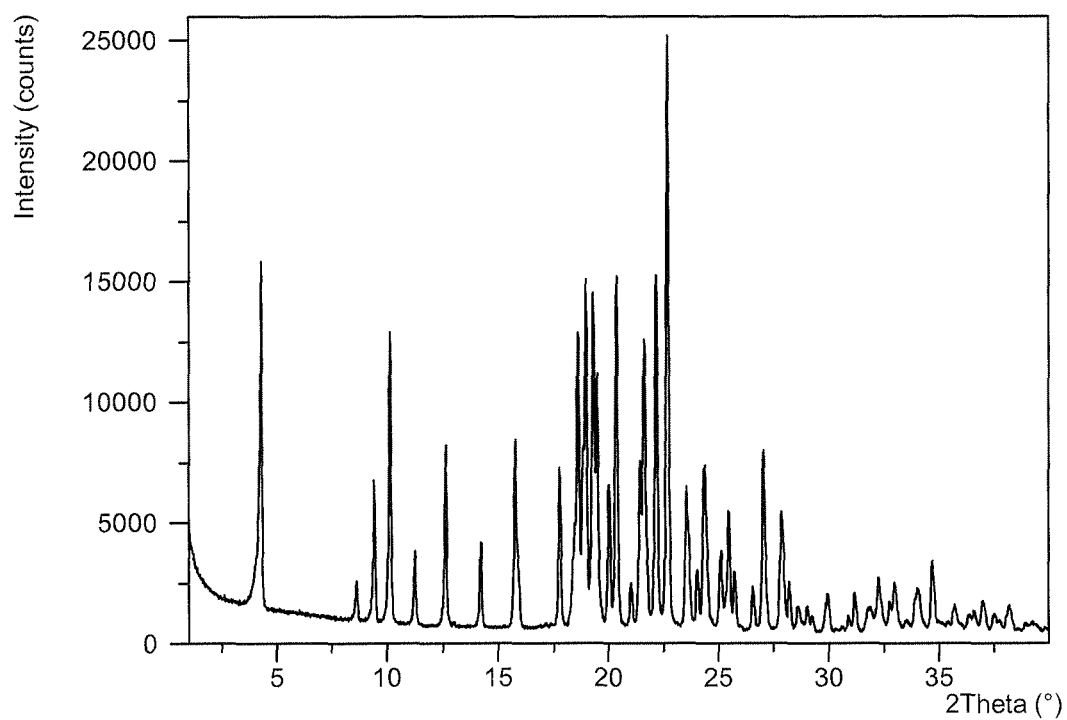
FIG. 54 shows XRPD pattern of crystalline 4-(pyrimidin-2-ylmethyl)-7-(4-(trifluoromethoxy)phenyl)-3,4-dihydrobenzo[f][1,4]oxazepin-5(2H)-one edisylate (Compound I Form XVII).
Figure 55:
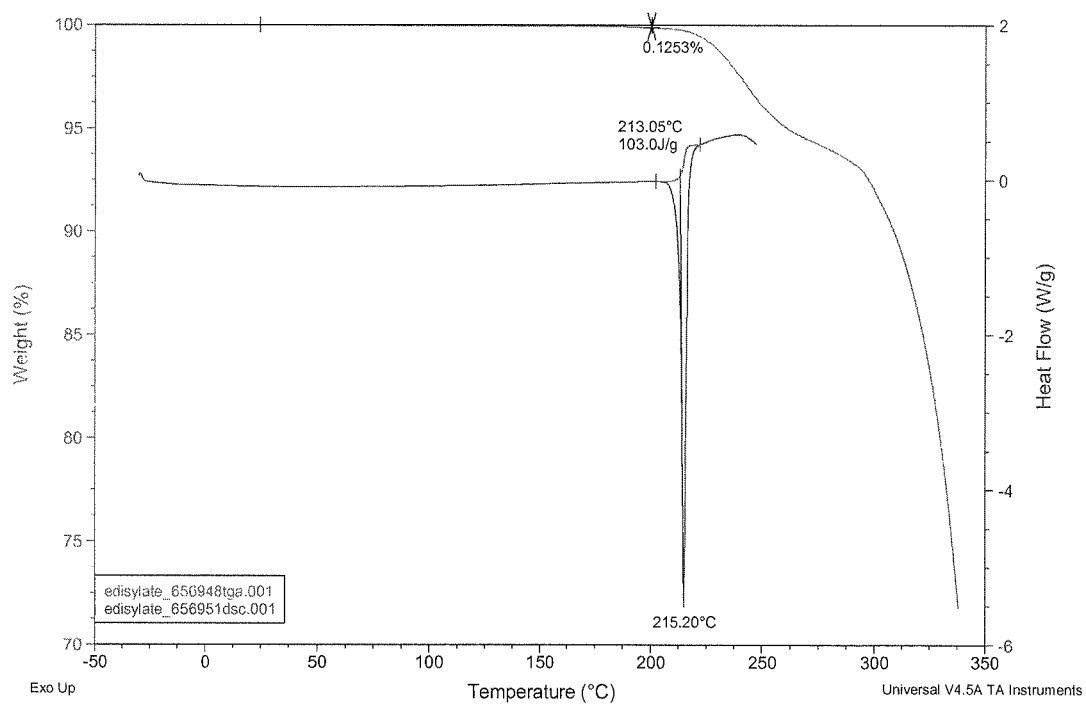
FIG. 55 shows TGA and DSC data of crystalline 4-(pyrimidin-2-ylmethyl)-7-(4-(trifluoromethoxy)phenyl)-3,4-dihydrobenzo[f][1,4]oxazepin-5 (2H)-one edisylate (Compound I Form XVII) vacuum dried at 21° C. for 3 hours.
Figure 56:
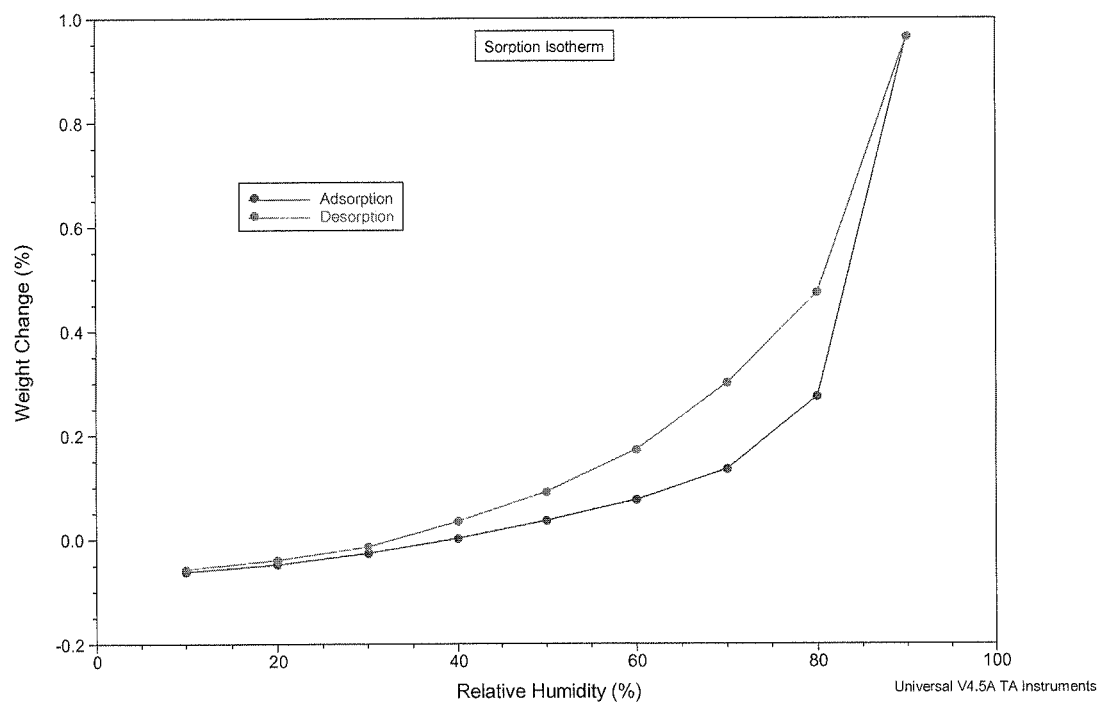
FIG. 56 shows sorption isotherm of crystalline 4-(pyrimidin-2-ylmethyl)-7-(4-(trifluoromethoxy)phenyl)-3,4-dihydrobenzo[f][1,4]oxazepin-5(2H)-one edisylate (Compound I Form XVII) vacuum dried at 21° C. for 3 hours.
Figure 57:
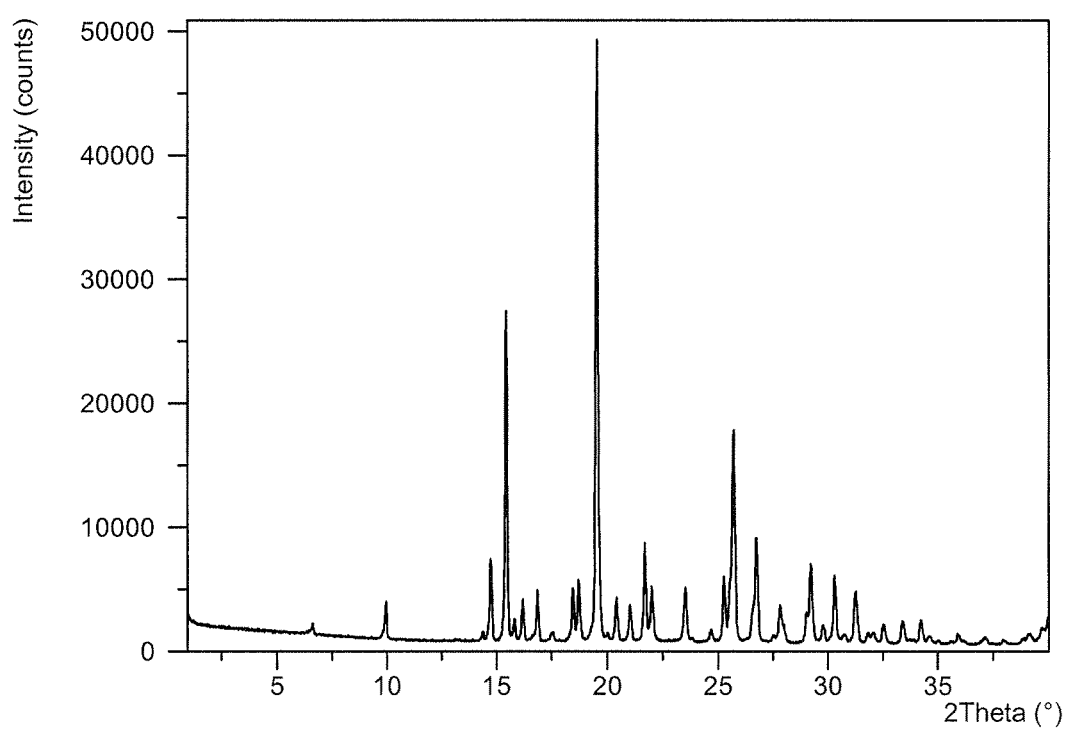
FIG. 57 shows XRPD pattern of crystalline 4-(pyrimidin-2-ylmethyl)-7-(4-(trifluoromethoxy)phenyl)-3,4-dihydrobenzo[f][1,4]oxazepin-5(2H)-one oxalate (Compound I Form XVIII).
Figure 58:
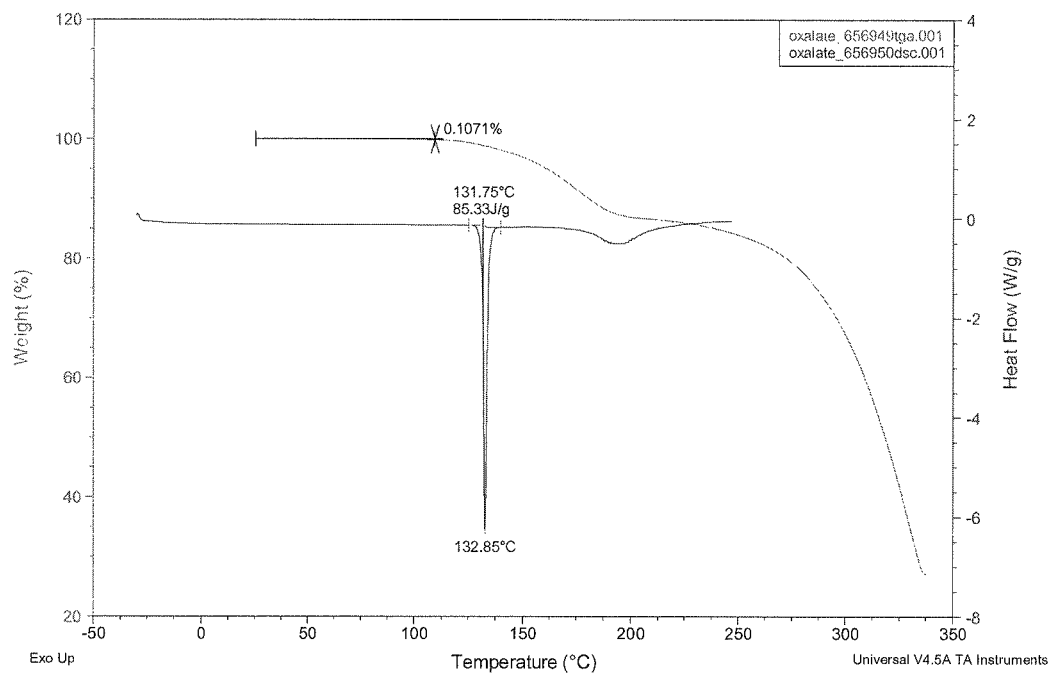
FIG. 58 shows TGA and DSC data of crystalline 4-(pyrimidin-2-ylmethyl)-7-(4-(trifluoromethoxy)phenyl)-3,4-dihydrobenzo[f][1,4]oxazepin-5(2H)-one oxalate (Compound I Form XVIII) vacuum dried at 21° C. for 3 hours.
Figure 59:
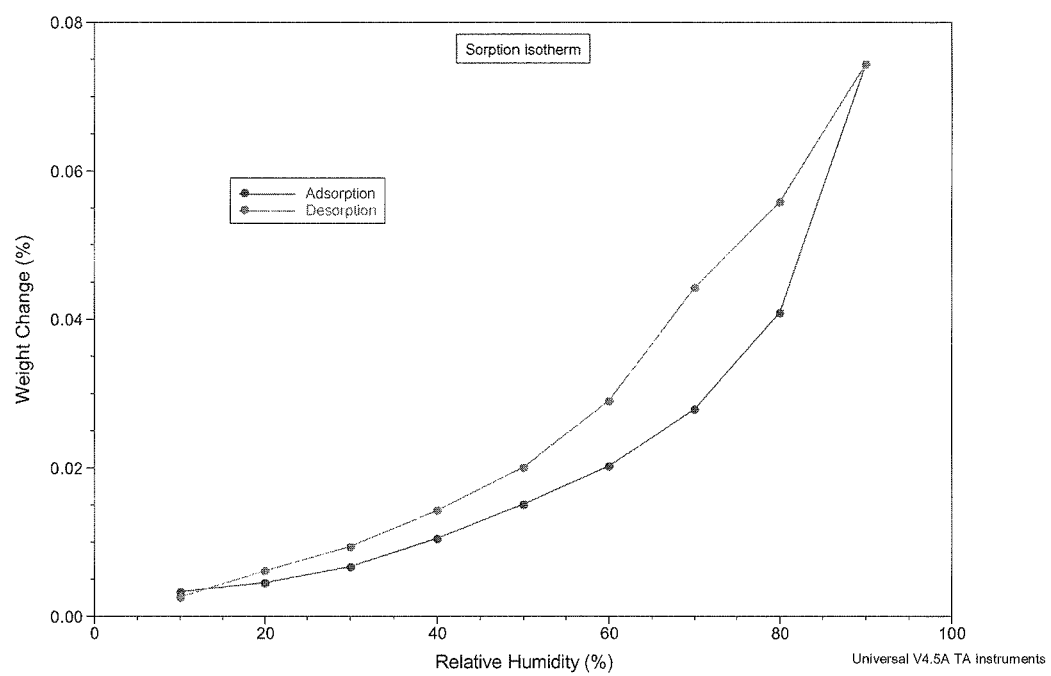
FIG. 59 shows sorption isotherm of crystalline 4-(pyrimidin-2-ylmethyl)-7-(4-(trifluoromethoxy)phenyl)-3,4-dihydrobenzo[f][1,4]oxazepin-5(2H)-one oxalate (Compound I Form XVIII) vacuum dried at 21° C. for 3 hours.

Crystallization procedure: 4M HCl solution in dioxane was used for these experiments. Each vial was charged with about 100 mg of Compound I Form I and 0.5 mL of chosen solvent to afford clear solutions at room temperature, followed by the addition of 1.05 equivalents of HCl (65 μL of 4M HCl solution in dioxane). Thick precipitates were formed upon acid additions. More solvents (0.5 mL) were added to improve stirring (except IPAc). All mixtures were allowed to stir at room temperature overnight. The obtained solids were isolated by filtration and dried under vacuum at room temperature overnight, followed by characterization by XRPD, DSC and TGA. Three unique XRPD patterns were obtained (FIG. 47).

(1) 4.4.1 Compound I Form XI

Figure 24:
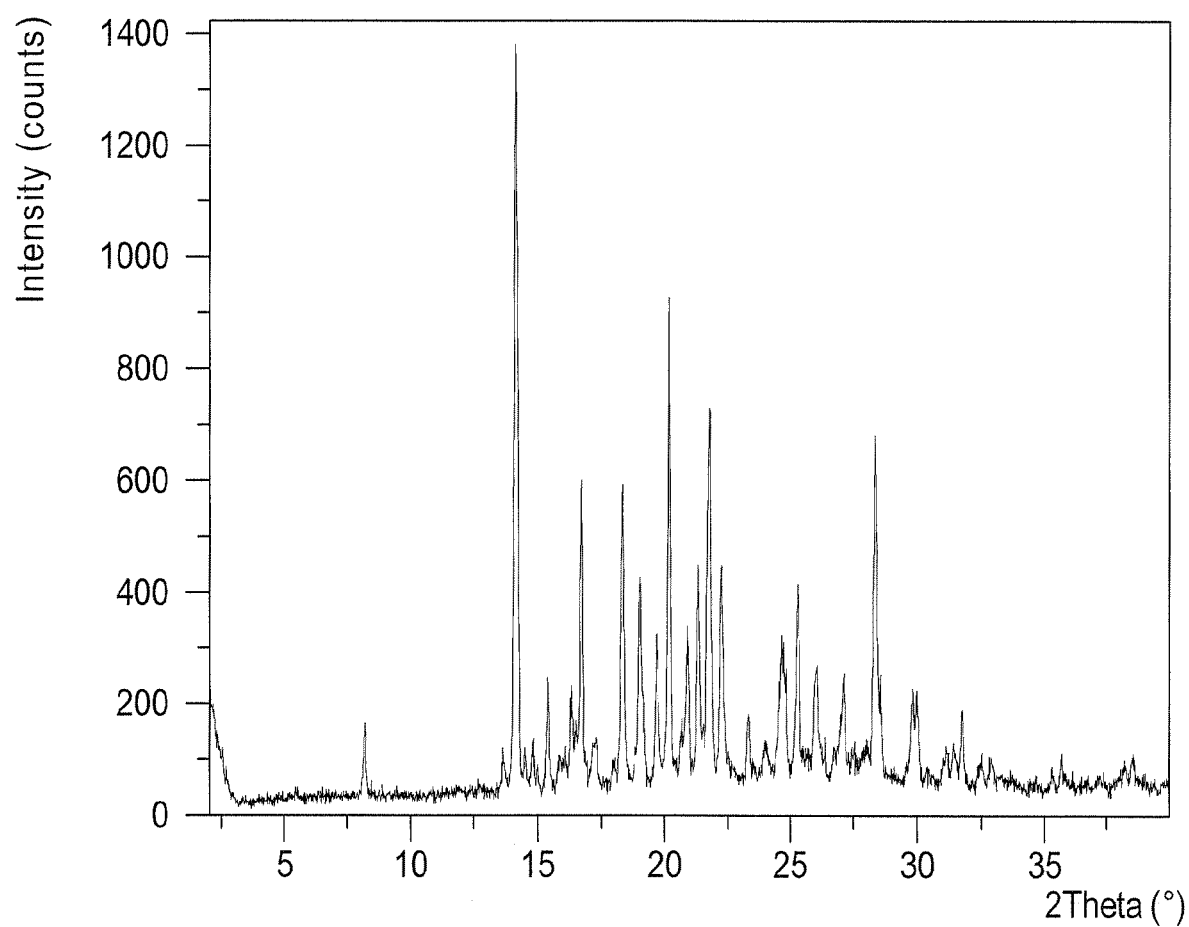
FIG. 24 shows an X-ray powder diffraction (XRPD) of Compound I Form XI.
Figure 26:
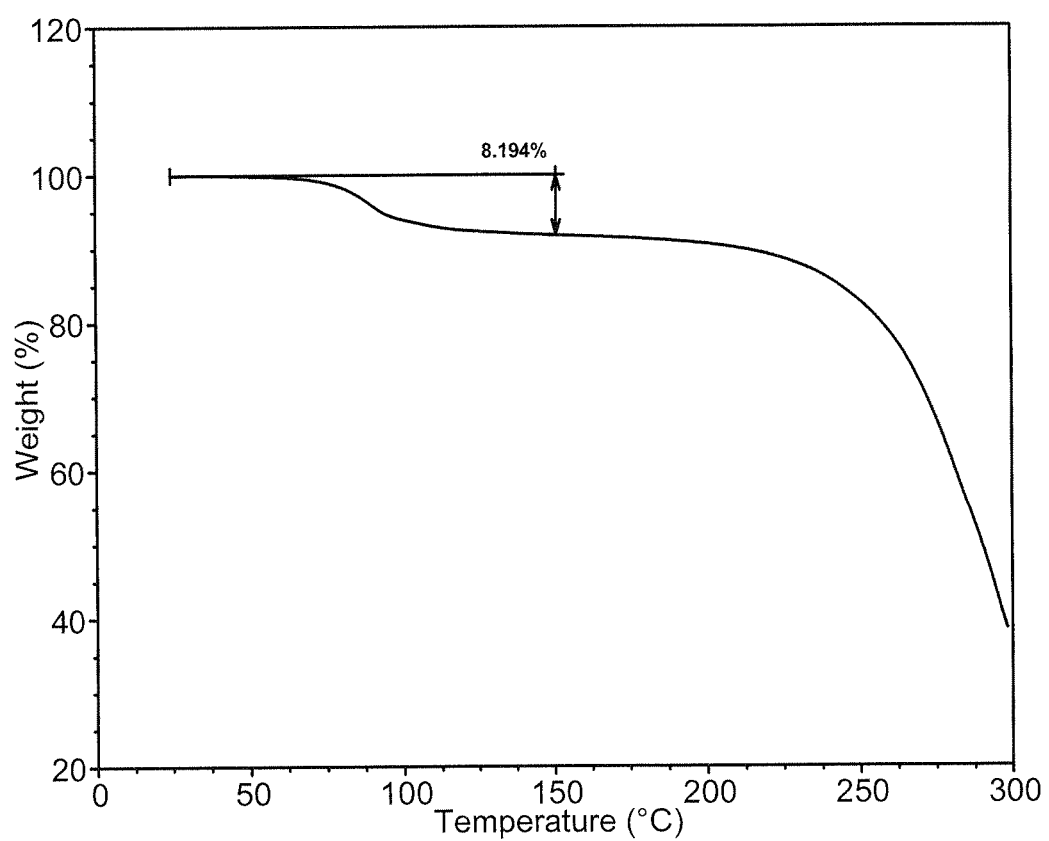
FIG. 26 shows a thermogravimetric analysis (TGA) of Compound I Form XI.

Solids from IPA were designated as Compound I Form XI. The characteristic XRPD peaks of Compound I Form XI include: 8.2, 14.1, 16.7, 18.3, 19.0, 20.2°2θ (FIG. 24). DSC shows broad endotherm with onset at about 119° C. (FIG. 25); TGA shows 8.19% weight loss at about 60 to 150° C. most likely corresponding to the loss of HCl (FIG. 26). KF shows 0.79% water.

(2) 4.4.2 Compound I Form XII

Figure 27:
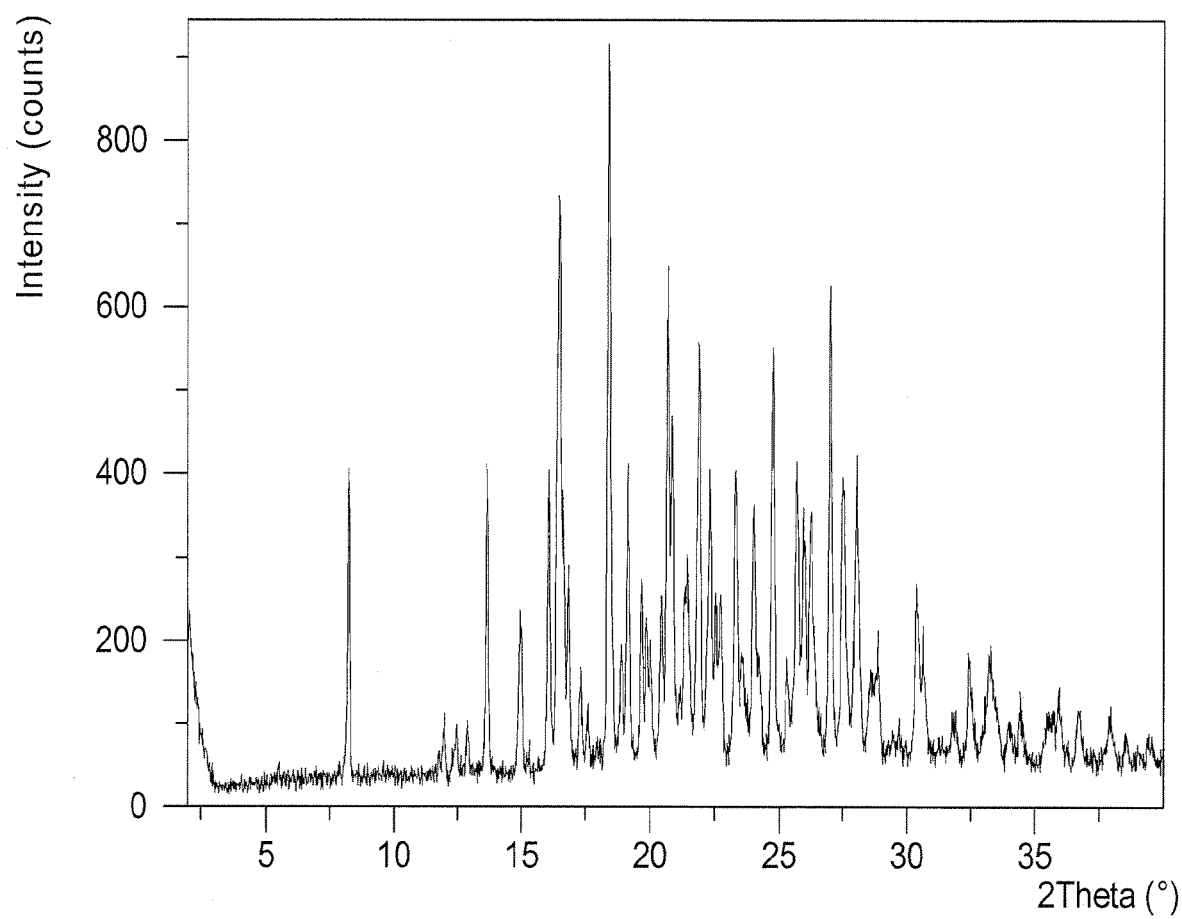
FIG. 27 shows an X-ray powder diffraction (XRPD) of Compound I Form XII.
Figure 29:
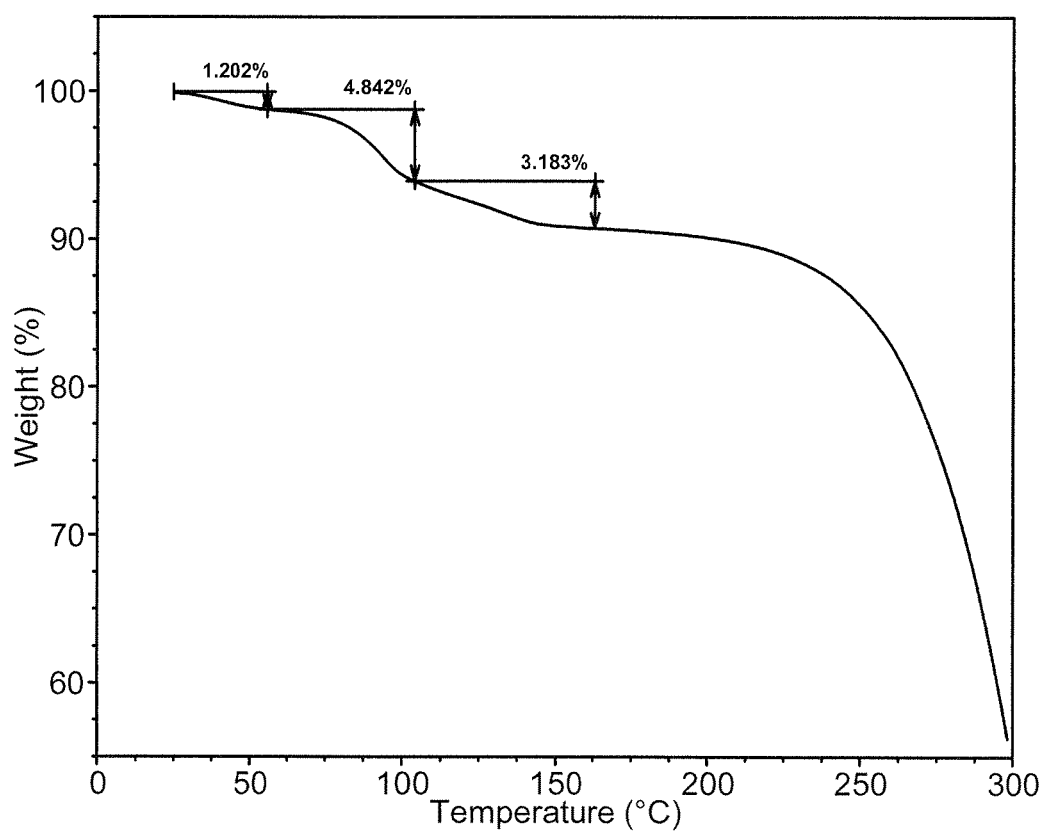
FIG. 29 shows a thermogravimetric analysis (TGA) of Compound I Form XII.

The solids obtained from IPAc were designated as Compound I Form XII. The characteristic XRPD peaks of Compound I Form XII include: 8.2, 13.7, 15.0, 16.5, 18.4, 20.7°2θ (FIG. 27). DSC shows two broad endotherms with onsets at about 29 and 126° C., corresponding to solvent loss and melting, respectively (FIG. 28). TGA shows 1.3, 4.8 and 3.2% weight losses most likely corresponding to solvent loss and step-wise HCl loss (FIG. 29). This form appears to be a hydrated form since KF shows 2.73 wt % water.

(3) 4.4.3 Compound I Form XIII

Figure 30:
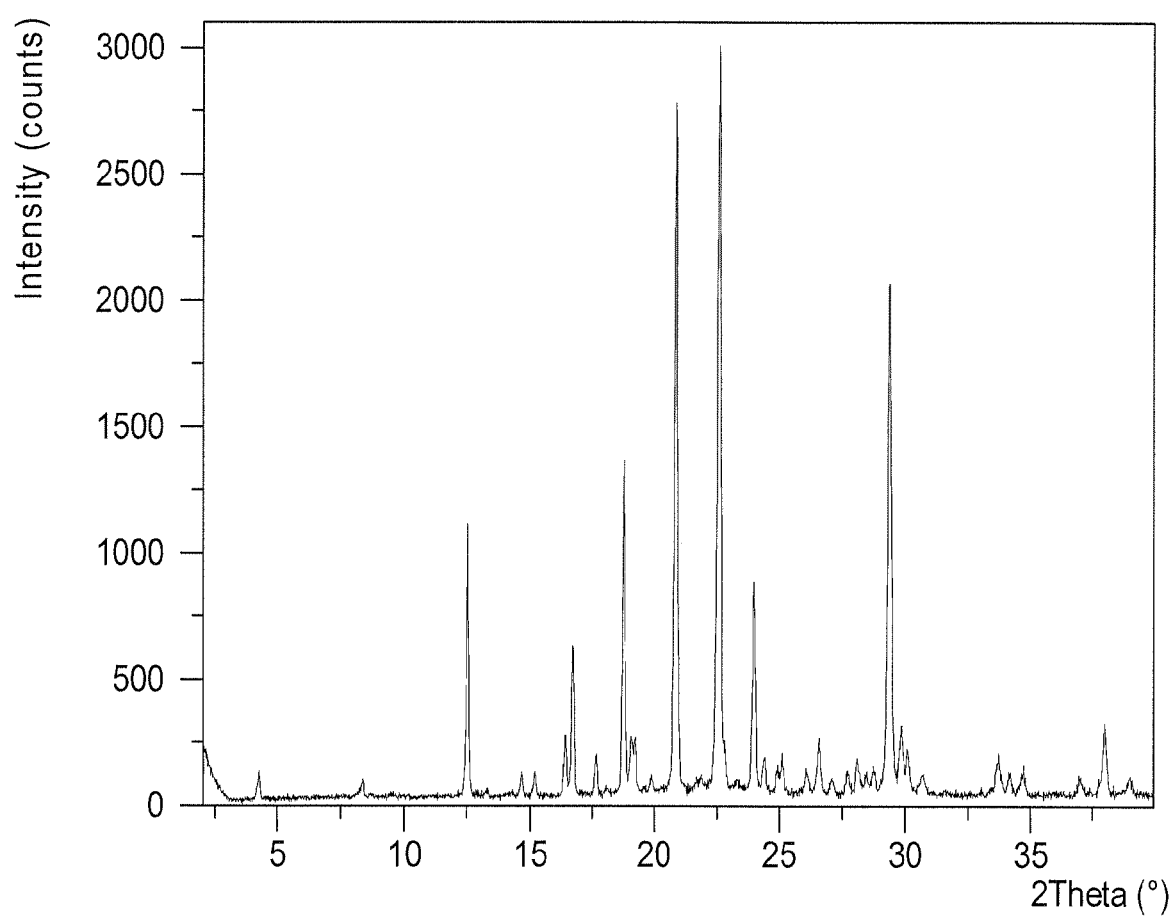
FIG. 30 shows an X-ray powder diffraction (XRPD) of Compound I Form XIII.
Figure 32:
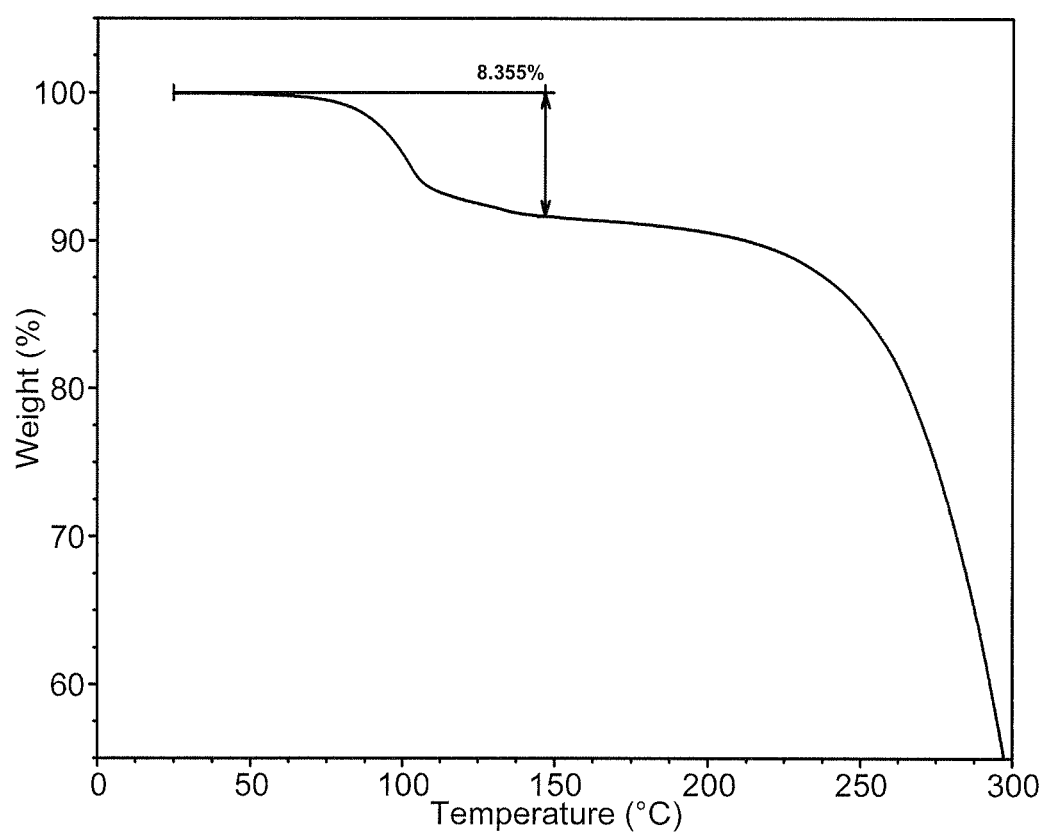
FIG. 32 shows a thermogravimetric analysis (TGA) of Compound I Form XIII.

Solids from dioxane, toluene and MeCN afforded XRPD patterns consistent with each other and were designated as Compound I Form XIII. The characteristic XRPD peaks of Compound I Form XIII include: 12.5, 16.7, 18.8, 20.9, 22.6°2θ (FIG. 30). All lots showed broad endotherm with onset at about 123 to 126° C. by DSC (FIG. 31), and 8.0 to 8.6% weight loss by TGA (FIG. 32), which also most likely corresponds to the loss of HCl.

vi. 4.5 Summary of all Crystalline Salt/Co-Crystal Forms

Co-crystal/salt screens of Compound I using 22 co-formers afforded four crystalline co-crystals/salts with MSA, BSA, p-TSA and HCl:

Compound I MSA has the highest melting point at about 185° C. and has only one stable polymorphic form.

Compound I BSA has a melting point at about 164° C. and has two polymorphs from the abbreviated stable form screen.

Compound I p-TSA has four polymorphs, each having a slightly different DSC profile. (m.p.=about 106, 133° C.).

Compound I HCl has three polymorphs. These polymorphs lose HCl before melting (m.p.=about 119 to 126° C.).

Table 18 summarizes analytical data for all obtained crystalline salt/co-crystal forms. Due to very low pKa (<2) and absence of the single crystal data, it is difficult to conclude whether some new crystalline solids are salts or co-crystals. Indeed each of these crystalline forms may be either a salt, co-crystal or a mixture of both.

These two forms are crystalline, have endotherms at about 185° C. and 164° C., respectively and exhibit relatively low hygroscopicity.

TABLE 18

Characterization of crystalline Compound I salts/co-crystals

| Compound I co-crystal Form by XRPD | DSC (° C.) | TGA weight loss (%) | KF (wt %) | $^1$H NMR | HPLC (% AN) | DVS |
|---|---|---|---|---|---|---|
| Form IV | 185 | 0.86% below 140° C. | 0.56 | 1 eq. MSA; No residual solvents | 100 | Slightly hygroscopic: 1.01 wt % at 90% RH |
| Form V (toluene solvate) | 80, 164 | 6.7% below 100° C. | n/a | 1 eq. BSA; 0.44 eq. toluene (6.6 wt %) | n/a | n/a |
| Form VI | 164 | 0.3% below 150° C. | 0.0 | 1 eq. BSA; No residual solvents | 98.9 | Non-hygroscopic: 0.11 wt % at 90% RH |
| Form VII (possible EtOAc solvate) | 74, 106, 133 | 4.8% below 100° C. | n/a | 1 eq. p-TSA, 0.2 eq. (4.1%) EtOAc | n/a | Moderately hygroscopic: 2.75 wt % at 90% RH |
| Form VIII (after DVS, most likely anhydrous) | 109, ~130, 132 | n/a | n/a | 1 eq. p-TSA; No residual solvents | n/a | n/a |
| Form IX (from MeCN, unknown) | 46, 105, 134 | 1.9% below 140° C. | n/a | 1 eq. p-TSA; no residual solvents | n/a | n/a |
| Form X (from Toluene/MeCN) | 58, 134 | 1.28% below 100° C. | 1.16 | 1.5 eq. p-TSA, no residual solvents | n/a | n/a |
| Form XI | 119 | 8.2 | 0.79 | n/a | n/a | n/a |
| Form XII (hydrate) | 29, 126 | 1.3, 4.8, 3.2 | 2.73 | n/a | n/a | n/a |
| Form XIII | 123 | 8.4 | 0.0 | n/a | n/a | n/a | n/a = not analyzed

5. Scale-up of Compound I Form IV and Compound I Form VI vii. 5.1 Compound I Form IV Compound I Form I (5 g) was dissolved in 45 mL toluene at room temperature, followed by dropwise addition of 1.05 equivalents of MSA (1.215 g in 5 mL MeCN). The precipitate started to form upon acid addition. The reaction mixture was allowed to stir at room temperature overnight. The solids were isolated by filtration, washed with toluene (2×5 mL) and dried under vacuum at about 50° C. overnight to afford 5.9 g of Compound I Form IV. Solids were analyzed by XRPD, DSC, TGA and NMR. All data were consistent with small scale.

viii. 5.2 Compound I Form VI

Compound I Form I (5 g) was dissolved in 45 mL IPAc at room temperature, followed by dropwise addition of 1.05 equivalents of BSA (2.0 g in 5 mL MeCN). A clear solution was obtained. Seeds of Compound I Form VI (about 1 mg) were added; and the precipitate started to form immediately. The reaction mixture was allowed to stir at room temperature overnight. The obtained solids were isolated by filtration, washed with IPAc (1×5 mL) and dried under vacuum at about 50° C. overnight to afford Compound I Form VI. Solids were analyzed by XRPD, DSC, TGA and NMR. All data were consistent with small scale.

Example 6

Compound I Sulfate Form I (Compound I FORM XIV)

Compound I (72.4 mg, 0.174 mmole) was dissolved in 1.0 ml of t-butyl methyl ether. Measured amount of sulfuric acid (10 µL, ~0.174 mmole) was diluted in 100 µL of tetrahydrofuran. The acid solution was added dropwise and stirring to Compound I solution producing milky solution that fainted a ball around the magnetic stir bar. Aliquots of isopropyl ether (2×0.5 mL) were added and the system was heated to 40° C. while stirred producing off-white suspension. After stirring at 40° C. for approximately 0.5 hour, the suspension was slow cooled to ambient temperature by turning off the heater. The solids were isolated by vacuum filtration.

Compound I FORM XIV was prepared by a slow cooling experiment from about 40° C. to 21° C. in a mixture of methyl t-butyl ether, diisopropyl ether, and tetrahydrofuran (10:10:1 volume ratio).

The XRPD pattern of Compound I FORM XIV is consistent with a crystalline material with characteristic peaks at 3.7, 16.2, 18.9, 20.0, and 23.8°±0.2°2θ. The successful indexing solution of its XRPD pattern indicates that the material is composed primarily or exclusively of a single crystalline phase.

The percentage of sulfate anion present in the molecule determined by ionic chromatography is consistent with Compound I monosulfate.

The DSC thermogram of Compound I FORM XIV demonstrated a sharp endotherm with onset at about 179° C. most likely associated with melting.

TGA thermogram of Compound I FORM XIV showed insignificant weight loss of about 0.26% from 25 to 179° C. Based on the TGA data, it appeared to be an anhydrous/non-solvated form.

DVS analysis of Compound I FORM XIV showed it deliquesced at around 70% RH.

TABLE 19

| XRPD Peak list of Compound I FORM XIV | | |
|---|---|---|
| No. | Pos. [°2Th.] | Rel. Int. [%] |
| 1 | 3.7 | 98.3 |
| 2 | 7.5 | 4.0 |
| 3 | 10.7 | 5.5 |
| 4 | 13.5 | 27.6 |
| 5 | 13.7 | 28.0 |
| 6 | 14.3 | 20.4 |
| 7 | 14.9 | 7.1 |
| 8 | 15.2 | 15.8 |
| 9 | 16.2 | 71.8 |
| 10 | 16.7 | 33.3 |
| 11 | 18.6 | 44.7 |
| 12 | 18.9 | 67.1 |
| 13 | 20.0 | 83.1 |
| 14 | 20.3 | 52.6 |
| 15 | 21.2 | 10.5 |
| 16 | 21.5 | 15.3 |
| 17 | 21.7 | 30.8 |
| 18 | 22.2 | 8.5 |
| 19 | 22.6 | 18.4 |
| 20 | 22.8 | 11.1 |
| 21 | 23.1 | 45.9 |
| 22 | 23.4 | 12.7 |
| 23 | 23.8 | 100.0 |
| 24 | 24.6 | 5.7 |
| 25 | 25.0 | 14.1 |
| 26 | 25.8 | 23.3 |
| 27 | 26.1 | 31.4 |
| 28 | 26.6 | 8.4 |
| 29 | 27.5 | 7.0 |
| 30 | 28.8 | 6.2 |
| 31 | 29.3 | 11.5 |

Example 7

Compound I Sulfate Form II (Compound I FORM XV)

Compound I (59.4 mg, 0.143 mmole) was dissolved in 1.0 ml of t-butyl methyl ether:isopropyl ether 1:1 at 40° C. Solution of sulfuric acid in tetrahydrofuran:isopropyl ether 1:3 (0.544 mL of 0.263 mmolar solution; 0.143 mmole) was added to the clear Compound I solution producing white milky solution. The system was allowed to slow cool overnight to ambient temperature with cooling rate of 0.1° C./min resulting in white thick suspension. An attempt was made to vacuum filter the solids however it appeared that they started to deliquesce. Solids (53 mg) were transferred immediately in a tared vial which was place open in a chamber over phosphorous pentoxide. After approximately 29 hours of exposure to strong desiccant, the sample appeared as dry large agglomerates freely flowing. The solids submitted for analyses.

In general, (Compound I FORM XV) was prepared by mixing the solution of Compound I and sulfuric acid at elevated temperature (about 40° C.) in a mixture of methyl t-butyl ether, diisopropyl ether, and tetrahydrofuran (4:7:1 volume ratio) followed by slow cooling of the resulting white milky solution from about 40° C. to 21° C. The isolated solids were dried over phosphorous pentoxide prior to XRPD analysis. The characteristic peaks of Compound I FORM XV include: 4.3, 10.2, 19.3, 20.3, and 22.6°±0.2°2θ.

The TGA thermogram of Compound I FORM XV showed insignificant weight loss of about 0.2% between 25 and 150° C. This result indicates it being an anhydrous/non-solvated form.

The DSC thermogram of Compound I FORM XV demonstrated an endotherm with onset at about 110° C. followed by a small exotherm at about 122° C. suggestive of melting and recrystallization to a material consistent with Compound I FORM XIV based on the next melting endotherm with onset at about 175° C.

Attempts were made to reproduce Compound I Forms XIV and XV with seeding (using the respective seed crystals) and resulted in mixtures with Form XV being the minor component. In another experiment, Compound I FORM XV was heated at about 130° C. for about 10 minutes and cooled to about 21° C. prior to XRPD analysis. The resulting material exhibited an XRPD pattern consistent with Compound I FORM XIV with minor Compound I FORM XV peak and small additional peaks. These results suggest Compound I FORM XIV being the more stable phase in comparison with Compound I FORM XV.

TABLE 20

XRPD peak list of Compound I Form XV

| No. | Pos. [°2Th.] | Rel. Int. [%] |
|---|---|---|
| 1 | 2.7 | 5.2 |
| 2 | 4.3 | 100.0 |
| 3 | 8.7 | 15.1 |
| 4 | 9.5 | 19.8 |
| 5 | 10.2 | 22.1 |
| 6 | 12.7 | 20.0 |
| 7 | 14.3 | 10.9 |
| 8 | 15.9 | 34.6 |
| 9 | 17.8 | 32.7 |
| 10 | 18.7 | 22.9 |
| 11 | 18.9 | 26.3 |
| 12 | 19.1 | 45.5 |
| 13 | 19.3 | 66.9 |
| 14 | 19.5 | 16.0 |
| 15 | 20.4 | 58.4 |
| 16 | 21.4 | 34.3 |
| 17 | 21.7 | 36.5 |
| 18 | 22.1 | 67.4 |
| 19 | 22.6 | 92.2 |
| 20 | 23.8 | 18.1 |
| 21 | 24.0 | 13.7 |
| 22 | 24.6 | 22.0 |
| 23 | 25.3 | 21.9 |
| 24 | 25.5 | 21.0 |
| 25 | 26.9 | 12.8 |
| 26 | 27.1 | 25.5 |
| 27 | 27.8 | 20.8 |
| 28 | 28.1 | 7.7 |
| 29 | 28.6 | 7.5 |
| 30 | 30.3 | 8.8 |
| 31 | 32.8 | 9.3 |
| 32 | 34.7 | 5.4 |

Example 8

Compound I Esylate Form I (Compound I FORM XVI)

Compound I (56.9 mg, 0.137 mmole) was dissolved in 1.0 ml of t-butyl methyl ether:isopropyl ether 1:1 at 40° C. with stirring. A measured amount of ethanesulfonic acid (11.5 μL, 0.137 mmole) was diluted in 50 μL of in tetrahydrofuran:isopropyl ether 1:3. The acid solution was added to Compound I solution at 40° C. resulting in milky solution that oiled out. Additionally, aliquots of tetrahydrofuran:isopropyl ether 1:3 mixture (2×0.5 mL) and isopropyl ether (2×0.5 mL) were added at 40° C. without any effect on the system. The sample was crash cooled by placing it a freezer. Off-white precipitation occurred within approximately 0.5 hour. The solids were isolated by vacuum filtration.

Compound I FORM XVI has only one crystalline form to date, and it was designated as Form I. It was first prepared by crash cooling from about 40° C. to −20° C. in a mixture of methyl t-butyl ether, tetrahydrofuran, and diisopropyl ether. The salt was reproduced in a solvent mixture of acetonitrile, tetrahydrofuran, and isopropyl ether after seeding.

The XRPD pattern of Compound I Form XVI is consistent with a crystalline material with characteristic peaks at 14.9, 16.4, 18.9, and 27.0°±0.2°2θ. The successful indexing solution of the XRPD pattern indicates that the material is composed primarily or exclusively of a single crystalline phase. The integration values and peak position in the $^1$H NMR spectrum of the material are consistent with the chemical structure of Compound I containing ethanesulfonic acid in approximate 1:1 stoichiometry.

The TGA thermogram of Compound I Form XVI showed insignificant weight loss of about 0.16% between 25 and 130.5° C. This result indicates it being an anhydrous/non-solvated form. The DSC thermogram of Compound I Form XVI showed a potential melting onset at about 130.5° C.

DVS analysis of Compound I esylate Form XVI showed it deliquesced at around 90% RH.

TABLE 21

XRPD peak list of Compound I esylate Form I (Compound I Form XVI)

| No. | Pos. [°2Th.] | Rel. Int. [%] |
|---|---|---|
| 1 | 5.5 | 31.2 |
| 2 | 9.8 | 4.6 |
| 3 | 11.0 | 28.7 |
| 4 | 11.9 | 9.9 |
| 5 | 13.2 | 7.5 |
| 6 | 14.9 | 100.0 |
| 7 | 16.4 | 73.4 |
| 8 | 17.5 | 15.6 |
| 9 | 18.3 | 33.1 |
| 10 | 18.9 | 50.8 |
| 11 | 19.7 | 6.7 |
| 12 | 19.8 | 11.6 |
| 13 | 20.2 | 6.4 |
| 14 | 21.7 | 36.1 |
| 15 | 22.2 | 39.2 |
| 16 | 22.4 | 14.8 |
| 17 | 22.8 | 46.6 |
| 18 | 23.9 | 33.6 |
| 19 | 24.6 | 15.4 |
| 20 | 25.2 | 18.5 |
| 21 | 26.2 | 10.7 |
| 22 | 26.6 | 7.4 |
| 23 | 27.0 | 49.5 |
| 24 | 27.8 | 5.6 |
| 25 | 29.3 | 8.8 |
| 26 | 30.2 | 9.0 |
| 27 | 33.1 | 7.6 |

Example 9.0

Compound I Edisylate Form I (Compound I Form XVII

Compound I (85.2 mg, 0.205 mmole) was dissolved in 1.0 ml of acetonitrile at ambient temperature. Ethanedisulfonic acid (27.6 mg, 0.110 mmole) was added as a solid when white precipitate formed instantly. Additionally, acetonitrile (0.5 mL) was added and the suspension was allowed to stir at ambient temperature for 1 hour. The solids were vacuum filtered, washed 3×0.3 mL of acetonitrile, and air-dried shortly under reduced pressure.

Compound I edisylate has only one crystalline form to date, and it was designated as Form XVII. The XRPD pattern has characteristic peaks at 4.3, 10.2, 19.0, 22.2, and 22.7°±0.2°2θ. The indexing solution of this XRPD pattern indicated that the material is composed primarily or exclusively of a single crystalline phase.

The integration values and peak position in the $^1$H NMR spectrum are consistent with the chemical structure of Compound I and signified the presence of 1,2-ethanedisulfonic acid in API: acid approximate 2:1 stoichiometry.

The thermal data including DSC and TGA thermograms are consistent with an anhydrous/non-solvated form with melting onset at about 213° C.

DVS analysis of (Compound I Form XVII) showed it is slightly hygroscopic with about 1% moisture uptake at 90% RH.

TABLE 22

XRPD peak list of Compound I Edysylate Form I (Compound I Form XVII)

| No. | Pos. [°2Th.] | Rel. Int. [%] |
|---|---|---|
| 1 | 4.3 | 57.1 |
| 2 | 8.6 | 6.6 |
| 3 | 9.5 | 23.4 |
| 4 | 10.2 | 48.2 |
| 5 | 11.3 | 12.0 |
| 6 | 12.6 | 30.4 |
| 7 | 14.2 | 14.3 |
| 8 | 15.8 | 31.9 |
| 9 | 17.8 | 26.7 |
| 10 | 18.6 | 49.0 |
| 11 | 18.8 | 28.3 |
| 12 | 19.0 | 57.5 |
| 13 | 19.3 | 55.3 |
| 14 | 19.5 | 41.5 |
| 15 | 20.0 | 22.9 |
| 16 | 20.4 | 58.5 |
| 17 | 21.0 | 6.3 |
| 18 | 21.5 | 27.1 |
| 19 | 21.6 | 47.7 |
| 20 | 22.2 | 57.6 |
| 21 | 22.7 | 100.0 |
| 22 | 23.6 | 23.2 |
| 23 | 24.1 | 8.8 |
| 24 | 24.4 | 26.5 |
| 25 | 25.1 | 12.2 |
| 26 | 25.5 | 19.4 |
| 27 | 25.7 | 9.3 |
| 28 | 26.6 | 7.1 |
| 29 | 27.0 | 30.2 |
| 30 | 27.9 | 19.5 |
| 31 | 28.2 | 7.7 |
| 32 | 29.9 | 5.9 |
| 33 | 31.2 | 5.9 |
| 34 | 32.3 | 7.5 |
| 35 | 33.0 | 7.2 |
| 36 | 34.0 | 6.4 |
| 37 | 34.7 | 11.1 |

Example 10.0

Compound I Oxalate Form I (Compound I Form XVIII)

Compound I oxalate was prepared by slow evaporation in multicomponent solvent system including acetonitrile, ethyl acetate, isopropyl acetates, diisopropyl ether, and tetrahydrofuran.

For example, Compound I (88.4 mg, 0.213 mmole) was dissolved in 0.5 ml of acetonitrile at ambient temperature. Solution of oxalic acid in multicomponent mixture of acetonitrile:isopropyl acetate:ethyl acetate:tetrahydrofuran:isopropyl ether 10:5:3:12:20 (0.89 mL of 0.24 mmolar solution; 0.214 mmole) was added resulting in slightly turbid yellow solution. The solution was allowed to slow evaporate from vial covered with perforated aluminum foil producing yellow opaque sticky sample. Aliquots of dioxane (100 μL) and isopropyl ether (2×100 μL) were added yielding white opaque solid in yellow solution. The solids were filtered under vacuum, washed with 2×0 5 mL of isopropyl ether, and air-dried shortly under reduced pressure.

Compound I oxalate salt has only one crystalline form to date, and it was designated as Form XVIII.

The XRPD pattern of Compound I Form XVIII is consistent with a crystalline material with characteristic peaks at 15.5, 19.5, and 25.7°±0.2°2θ. The successful indexing solution of its XRPD pattern indicates that the material is composed primarily or exclusively of a single crystalline phase.

The integration values and peak position in the $^1$H NMR spectrum of the material are consistent with the chemical structure of Compound I.

The thermal data including DSC and TGA thermograms are consistent with an anhydrous/non-solvated form with melting onset at about 132° C.

DVS analysis of Compound I Form XVIII showed it is non-hygroscopic with about 0.075% moisture uptake at 90% RH.

TABLE 23

XRPD peak list of Compound I Oxalate Form I (Compound I Form XVIII)

| No. | Pos. [°2Th.] | Rel. Int. [%] |
|---|---|---|
| 1 | 10.0 | 6.0 |
| 2 | 14.8 | 13.5 |
| 3 | 15.5 | 54.1 |
| 4 | 16.2 | 6.5 |
| 5 | 16.9 | 8.2 |
| 6 | 18.5 | 8.3 |
| 7 | 18.7 | 9.9 |
| 8 | 19.5 | 100.0 |
| 9 | 20.4 | 6.9 |
| 10 | 21.0 | 5.8 |
| 11 | 21.7 | 16.0 |
| 12 | 22.0 | 8.7 |
| 13 | 23.5 | 8.7 |
| 14 | 25.3 | 10.3 |
| 15 | 25.5 | 9.2 |
| 16 | 25.7 | 34.8 |
| 17 | 26.7 | 16.9 |
| 18 | 27.8 | 6.0 |
| 19 | 29.2 | 12.4 |
| 20 | 30.3 | 10.3 |
| 21 | 31.3 | 8.0 |

The present disclosure is not to be limited in scope by the specific embodiments disclosed in the examples, which are intended to be illustrations of a few embodiments of the disclosure, nor is the disclosure to be limited by any embodiments that are functionally equivalent within the scope of this disclosure. Indeed, various modifications of the disclosure in addition to those shown and described herein will become apparent to those skilled in the art and are intended to fall within the scope of the appended claims. To this end, it should be noted that one or more hydrogen atoms or methyl groups may be omitted from the drawn structures consistent with accepted shorthand notation of such organic compounds, and that one skilled in the art of organic chemistry would readily appreciate their presence

What is claimed is:

1. Crystalline 4-(pyrimidin-2-ylmethyl)-7-(4-(trifluoromethoxy)phenyl)-3,4-dihydrobenzo[f][1,4]oxazepin-5(2H)-one (Compound I Form I), characterized by an X-ray powder diffractogram comprising the following peaks: 12.3, 23.8, and 27.2°2θ±0.2°2θ, as determined on a diffractometer using Cu-Kα radiation at a wavelength of 1.5406 Å.

2. Compound I Form I according to claim 1, wherein the diffractogram further comprises peaks at 20.5 and 20.7°2θ±0.2°2θ.

3. Crystalline 4-(pyrimidin-2-ylmethyl)-7-(4-(trifluoromethoxy)phenyl)-3,4-dihydrobenzo[f][1,4]oxazepin-5(2H)-one (Compound I Form II), characterized by an X-ray powder diffractogram comprising the following peaks: 15.7, 17.5, and 20.3°2θ±0.2°2θ, as determined on a diffractometer using Cu-Kα radiation at a wavelength of 1.5406 Å.

4. Compound I Form II according to claim 3, wherein the diffractogram further comprises peaks at 11.7, 19.7, and 23.2°2θ±0.2°2θ.

5. Crystalline 4-(pyrimidin-2-ylmethyl)-7-(4-(trifluoromethoxy)phenyl)-3,4-dihydrobenzo[f][1,4]oxazepin-5(2H)-one (Compound I Form III), characterized by an X-ray powder diffractogram comprising the following peaks: 13.6, 20.6, and 24.1°2θ±0.2°2θ, as determined on a diffractometer using Cu-Kα radiation at a wavelength of 1.5406 Å.

6. Compound I Form III according to claim 5, wherein the diffractogram further comprises peaks at 17.2, 19.1, and 21.7°2θ±0.2°2θ.

7. Crystalline 4-(pyrimidin-2-ylmethyl)-7-(4-(trifluoromethoxy)phenyl)-3,4-dihydrobenzo[f][1,4]oxazepin-5(2H)-one methanesulfonic acid (Compound I Form IV) characterized by an X-ray powder diffractogram comprising the following peaks: 16.5, 18.9, and 20.6°2θ±0.2°2θ, as determined on a diffractometer using Cu-Kα radiation at a wavelength of 1.5406 Å.

8. Compound I Form IV according to claim 7, wherein the diffractogram further comprises peaks at 4.8, 14.2, and 19.7°2θ±0.2°2θ.

9. Crystalline 4-(pyrimidin-2-ylmethyl)-7-(4-(trifluoromethoxy)phenyl)-3,4-dihydrobenzo[f][1,4]oxazepin-5(2H)-one benzene sulfonic acid (Compound I Form V) characterized by an X-ray powder diffractogram comprising the following peaks: 8.0, 8.6, and 13.9°2θ±0.2°2θ, as determined on a diffractometer using Cu-Kα radiation at a wavelength of 1.5406 Å.

10. Compound I Form V according to claim 9, wherein the diffractogram further comprises peaks at 17.1, 18.9, and 20.1°2θ±0.2°2θ.

11. Crystalline 4-(pyrimidin-2-ylmethyl)-7-(4-(trifluoromethoxy)phenyl)-3,4-dihydrobenzo[f][1,4]oxazepin-5(2H)-one benzene sulfonic acid (Compound I Form VI) characterized by an X-ray powder diffractogram comprising the following peaks: 4.0, 14.7, and 17.9°2θ±0.2°2θ, as determined on a diffractometer using Cu-Kα radiation at a wavelength of 1.5406 Å.

12. Compound I Form VI according to claim 11, wherein the diffractogram further comprises peaks at 7.9, 9.3, 9.9°2θ±0.2°2θ.

13. Crystalline 4-(pyrimidin-2-ylmethyl)-7-(4-(trifluoromethoxy)phenyl)-3,4-dihydrobenzo[f][1,4]oxazepin-5(2H)-one p-toluenesulfonic acid (Compound I Form VII), characterized by an X-ray powder diffractogram comprising the following peaks: 5.4, 18.2, and 18.8°2θ±0.2°2θ, as determined on a diffractometer using Cu-Kα radiation at a wavelength of 1.5406 Å.

14. Compound I Form VII according to claim 13, wherein the diffractogram further comprises peaks at 8.1, and 15.5°2θ±0.2°2θ.

15. Crystalline 4-(pyrimidin-2-ylmethyl)-7-(4-(trifluoromethoxy)phenyl)-3,4-dihydrobenzo[f][1,4]oxazepin-5(2H)-one p-toluenesulfonic acid (Compound I Form VIII), characterized by an X-ray powder diffractogram comprising the following peaks: 6.2, 15.3, and 18.4°2θ±0.2°2θ, as determined on a diffractometer using Cu-Kα radiation at a wavelength of 1.5406 Å.

16. Compound I Form VIII according to claim 15, wherein the diffractogram further comprises peaks at 3.1, 5.3, and 9.2°2θ±0.2°2θ.

17. Crystalline 4-(pyrimidin-2-ylmethyl)-7-(4-(trifluoromethoxy)phenyl)-3,4-dihydrobenzo[f][1,4]oxazepin-5(2H)-one p-toluenesulfonic acid (Compound I Form IX), characterized by an X-ray powder diffractogram comprising the following peaks: 5.9, 8.9, and 17.7°2θ±0.2°2θ, as determined on a diffractometer using Cu-Kα radiation at a wavelength of 1.5406 Å.

18. Compound I Form IX according to claim 17, wherein the diffractogram farther comprises peaks at 3.0, 11.8, and 14.8°2θ±0.2°2θ.

19. Crystalline 4-(pyrimidin-2-ylmethyl)-7-(4-(trifluoromethoxy)phenyl)-3,4-dihydrobenzo[f][1,4]oxazepin-5(2H)-one p-toluenesulfonic acid (Compound I Form X), characterized by an X-ray powder diffractogram comprising the following peaks: 5.2, 15.5, 7.8 10.5 and 18.1°2θ±0.2°2θ, as determined on a diffractometer using Cu-Kα radiation at a wavelength of 1.5406 Å.

20. Crystalline 4-(pyrimidin-2-ylmethyl)-7-(4-(trifluoromethoxy)phenyl)-3,4-dihydrobenzo[f][1,4]oxazepin-5(2H)-one HCl (Compound I Form XI), characterized by an X-ray powder diffractogram comprising the following peaks: 14.1, 16.7, and 19.0°2θ±0.2°2θ, as determined on a diffractometer using Cu-Kα radiation at as wavelength of 1.5406 Å.

21. Compound I Form XI according to claim 20, wherein the diffractogram further comprises peaks at 8.2, 18.3, and 20.2°2θ±0.2°2θ.

22. Crystalline 4-(pyrimidin-2-ylmethyl)-7-(4-(trifluoromethoxy)phenyl)-3,4-dihydrobenzo[f][1,4]oxazepin-5(2H)-one HCl (Compound I Form XII), characterized by an X-ray powder diffractogram comprising the following peaks: 16.5, 18.4, and 20.7°2θ±0.2°2θ, as determined on a diffractometer using Cu-Kα radiation at a wavelength of 1.5406 Å.

23. Compound I Form XII according to claim 22, wherein the diffractogram further comprises peaks at 8.2, 13.7, and 15.0°2θ±0.2°2θ.

24. Crystalline 4-(pyrimidin-2-ylmethyl)-7-(4-(trifluoromethoxy)phenyl)-3,4-dihydrobenzo[f][1,4]oxazepin-5(2H)-one HCl (Compound I Form XIII), characterized by an X-ray powder diffractogram comprising the following peaks: 18.8, 20.9, and 22.6°2θ±0.2°2θ, as determined on a diffractometer using Cu-Kα radiation at a wavelength of 1.5406 Å.

25. Compound I Form XIII according to claim 24, wherein the diffractogram further comprises peaks at 12.5 and 16.7°2θ±0.2°2θ.

26. Crystalline 4-(pyrimidin-2-ylmethyl)-7-(4-(trifluoromethoxy)phenyl)-3,4-dihydrobenzo[f][1,4]oxazepin-5(2H)-one mono sulfate (Compound I Form XIV), characterized by an X-ray powder diffractogram comprising the following peaks: 3.7, 16.2, 18.9, 20.0, 20.3, and 23.8°2θ±0.2°2θ, as determined on a diffractometer using Cu-Kα radiation at a wavelength of 1.5406 Å.

27. Crystalline 4-(pyrimidin-2-ylmethyl)-7-(4-(trifluoromethoxy)phenyl)-3,4-dihydrobenzo[f][1,4]oxazepin-5(2H)-one mono sulfate (Compound I Form XV or Compound I Sulfate Form II), characterized by an X-ray powder diffractogram comprising the following peaks: 4.3, 19.1, 19.3, 20.4, 21.4, 21.7, 22.1, and 22.6°2θ±0.2°2θ, as determined on a diffractometer using Cu-Kα radiation at a wavelength of 1.5406 Å.

28. Crystalline 4-(pyrimidin-2-ylmethyl)-7-(4-(trifluoromethoxy)phenyl)-3,4-dihydrobenzo[f][1,4]oxazepin-5 (2H)-one esylate (Compound I Form XVI or Compound I Esylate Form I), characterized by an X-ray powder diffractogram comprising the following peaks: 14.9, 16.4, 18.9, and 27.0°±0.2°2θ, as determined on a diffractometer using Cu-Kα radiation at a wavelength of 1.5406 Å.

29. Crystalline 4-(pyrimidin-2-ylmethyl)-7-(4-(trifluoromethoxy)phenyl)-3,4-dihydrobenzo[f][1,4]oxazepin-5 (2H)-one edisylate (Compound I Form XVII or Compound I Edisylate Form I), characterized by an X-ray powder diffractogram comprising the following peaks: 4.3, 10.2, 19.0, 22.2, and 22.7°±0.2°2θ, as determined on a diffractometer using Cu-Kα radiation at a wavelength of 1.5406 Å.

30. Crystalline 4-(pyrimidin-2-ylmethyl)-7-(4-(trifluoromethoxy)phenyl)-3,4-dihydrobenzo[f][1,4]oxazepin-5 (2H)-one oxalate (Compound I Form XVIII or Compound I Oxalate Form I), characterized by an X-ray powder diffractogram comprising the following peaks: 15.5, 19.5, and 25.7°2θ±0.2°2θ, as determined on a diffractometer using Cu-Kα radiation at a wavelength of 1.5406 Å.

31. A pharmaceutical composition comprising a therapeutically effective amount of a compound according to any one of claims 1, 3, 5, 7, 9, 11, 13, 15, 17, 19, 20, 22, 24, 26, 28, 29 and 30 and a pharmaceutically acceptable excipient.

* * * * *